US011317830B2

(12) United States Patent
Shen et al.

(10) Patent No.: US 11,317,830 B2
(45) Date of Patent: *May 3, 2022

(54) SYSTEMS AND METHODS FOR MANAGING PRESSURIZATION TIMERS FOR MONITORING AND/OR MANAGING A PERSON'S POSITION

(71) Applicant: Leaf Healthcare, Inc., Pleasanton, CA (US)

(72) Inventors: Daniel Shen, Stanford, CA (US); Barrett Larson, Palo Alto, CA (US); Mark Weckwerth, Pleasanton, CA (US)

(73) Assignee: LEAF HEALTHCARE, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/168,816

(22) Filed: Feb. 5, 2021

(65) Prior Publication Data

US 2021/0177305 A1 Jun. 17, 2021

Related U.S. Application Data

(63) Continuation of application No. 16/548,553, filed on Aug. 22, 2019, now Pat. No. 10,912,491, which is a
(Continued)

(51) Int. Cl.
*A61B 5/11* (2006.01)
*G08B 21/04* (2006.01)

(52) U.S. Cl.
CPC .............. *A61B 5/11* (2013.01); *A61B 5/1115* (2013.01); *G08B 21/0446* (2013.01); *G08B 21/0453* (2013.01)

(58) Field of Classification Search
CPC ....... A61B 5/00; A61B 5/0205; A61B 5/1115; A61B 5/1116; A61B 5/1117;
(Continued)

(56) References Cited

U.S. PATENT DOCUMENTS 3,602,215 A 8/1971 Parnell .......................... 600/508
4,055,168 A 10/1977 Miller et al. .................. 600/594
(Continued)

FOREIGN PATENT DOCUMENTS

JP 08238275 A 9/1996 ............... A61B 5/00
JP 11136191 A 5/1999 ............... A61B 5/00
(Continued)

OTHER PUBLICATIONS

NPL_search (Sep. 27, 2021).*
(Continued)

*Primary Examiner* — Van T Trieu
(74) *Attorney, Agent, or Firm* — Slayden Grubert Beard PLLC

(57) ABSTRACT

A system for monitoring a person may include a person-worn sensor device including at least one sensor (e.g., at least one accelerometer, magnetometer, altimeter, etc.) configured to collect sensor data and a processor to process data from the person-worn sensor device. The processor may be configured to determine or access an orientation of a physical support apparatus (e.g., bed, table, wheelchair, chair, sofa, or other structure for supporting the person), receive sensor data collected by the person-worn sensor device, calculate an orientation of the person relative to the physical support apparatus based on (a) the orientation of the physical support apparatus and (b) the sensor data collected by the person-worn sensor device, and identify, based on the determined orientation of the person relative to the physical support apparatus, a physical support apparatus exit condi-
(Continued)

tion indicating an occurrence or anticipated occurrence of the person exiting the physical support apparatus.

28 Claims, 29 Drawing Sheets

Related U.S. Application Data continuation of application No. 15/423,665, filed on Feb. 3, 2017, now Pat. No. 10,758,162, which is a continuation-in-part of application No. 14/543,887, filed on Nov. 17, 2014, now Pat. No. 9,728,061, said application No. 15/423,665 is a continuation-in-part of application No. 13/070,189, filed on Mar. 23, 2011, now Pat. No. 10,729,357.

(60) Provisional application No. 61/905,106, filed on Nov. 15, 2013, provisional application No. 62/047,642, filed on Sep. 8, 2014, provisional application No. 61/438,732, filed on Feb. 2, 2011, provisional application No. 61/326,664, filed on Apr. 22, 2010, provisional application No. 61/411,647, filed on Nov. 9, 2010, provisional application No. 61/393,364, filed on Oct. 15, 2010, provisional application No. 61/373,260, filed on Aug. 12, 2010.

(58) Field of Classification Search
CPC ........... G08B 21/0446; G08B 21/0453; H04W 4/026; H04W 4/027; H04W 4/028
See application file for complete search history.

(56) References Cited

U.S. PATENT DOCUMENTS

| | | | |
|---|---|---|---|
| 5,038,137 A | 8/1991 | Lloyd | 340/573.7 |
| 5,146,206 A | 9/1992 | Callaway | 340/573.7 |
| 5,267,364 A | 12/1993 | Volk | 5/713 |
| 5,300,921 A | 4/1994 | Hoch et al. | 340/573.6 |
| 5,398,019 A | 3/1995 | Barnett et al. | 340/573.7 |
| 5,430,435 A | 7/1995 | Hoch et al. | 340/573.7 |
| 5,519,380 A | 5/1996 | Edwards | 340/573.4 |
| 5,588,437 A | 12/1996 | Byrne et al. | 600/504 |
| 5,623,760 A | 4/1997 | Newham | 29/622 |
| 5,669,377 A | 9/1997 | Fenn | 128/200.24 |
| 5,769,784 A | 6/1998 | Barnett et al. | 600/300 |
| 5,774,055 A | 6/1998 | Pomerantz | 340/573.7 |
| 5,906,016 A | 5/1999 | Ferrand et al. | 5/600 |
| 6,014,346 A | 1/2000 | Malone | 368/10 |
| 6,030,351 A | 2/2000 | Schmidt et al. | 600/592 |
| 6,049,281 A | 4/2000 | Osterweil | 340/573.4 |
| 6,129,686 A | 10/2000 | Friedman | 600/595 |
| 6,287,253 B1 | 9/2001 | Ortega et al. | 600/300 |
| 6,305,221 B1 | 10/2001 | Hutchings | 73/488 |
| 6,397,190 B1 | 5/2002 | Goetz | 705/3 |
| 6,447,460 B1 | 9/2002 | Zheng et al. | 600/549 |
| 7,007,327 B2 | 3/2006 | Ogawa et al. | 5/609 |
| 7,090,647 B2 | 8/2006 | Mimura et al. | 600/587 |
| 7,184,963 B1 | 2/2007 | Shannon | 705/2 |
| 7,251,845 B2 | 8/2007 | Schaller et al. | 5/613 |
| 7,325,453 B2 | 2/2008 | Bremer et al. | 73/510 |
| 7,378,975 B1 | 5/2008 | Smith et al. | 340/573.1 |
| 7,600,409 B2 | 10/2009 | Ukai | 73/1.39 |
| 7,634,379 B2 | 12/2009 | Noble | 702/141 |
| 7,698,830 B2 | 4/2010 | Townsend et al. | 33/512 |
| 7,753,861 B1 | 7/2010 | Kahn et al. | 600/595 |
| 8,237,551 B2 | 8/2012 | Sweeney et al. | 340/286.07 |
| 8,284,070 B2 | 10/2012 | Chaudhari et al. | 340/686.1 |
| 8,306,666 B2 | 11/2012 | Huber et al. | 700/275 |
| 8,410,826 B2 | 4/2013 | Koto et al. | 327/108 |
| 8,410,926 B1 | 4/2013 | Gary, Jr. et al. | 340/539.12 |
| 8,436,737 B1 | 5/2013 | Trout | 340/573.7 |
| 8,475,368 B2 | 7/2013 | Tran et al. | 600/300 |
| 8,533,879 B1 | 9/2013 | Taylor | 5/713 |
| 8,594,776 B2 | 11/2013 | Mccombie et al. | 600/513 |
| 8,604,916 B2 | 12/2013 | Mcneely et al. | 340/286.07 |
| 8,606,344 B2 | 12/2013 | Dimaio et al. | 600/407 |
| 8,674,826 B2 | 3/2014 | Becker et al. | 340/539.12 |
| 8,684,900 B2 | 4/2014 | Tran | 600/3 |
| 8,781,504 B1 | 7/2014 | Liu | 455/456.5 |
| 8,909,330 B2 | 12/2014 | Mccombie et al. | 600/513 |
| 8,956,293 B2 | 2/2015 | Mccombie et al. | 600/301 |
| 8,956,294 B2 | 2/2015 | Mccombie et al. | 600/301 |
| 9,005,141 B1 | 4/2015 | Najafi et al. | 600/595 |
| 9,055,928 B2 | 6/2015 | Mccombie et al. | |
| 9,141,974 B2 | 9/2015 | Jones et al. | |
| 9,492,092 B2 | 11/2016 | Mccombie et al. | |
| 9,545,342 B2 * | 1/2017 | Cretu-Petra | A61B 5/6808 |
| 9,566,007 B2 | 2/2017 | Mccombie et al. | |
| 9,655,546 B2 | 5/2017 | Shen et al. | |
| 9,901,261 B2 | 2/2018 | Mccombie et al. | |
| 10,004,447 B2 | 6/2018 | Shen et al. | |
| 10,020,075 B2 | 7/2018 | Perlman et al. | |
| 10,631,732 B2 | 4/2020 | Larson et al. | |
| 2001/0049609 A1 | 12/2001 | Girouard et al. | 705/3 |
| 2001/0050613 A1 | 12/2001 | Clark | 340/539.32 |
| 2003/0171954 A1 | 9/2003 | Guerin et al. | 705/2 |
| 2004/0015058 A1 | 1/2004 | Besson et al. | 600/301 |
| 2004/0046668 A1 | 3/2004 | Smith et al. | 340/573.7 |
| 2005/0033200 A1 | 2/2005 | Soehren et al. | 600/595 |
| 2005/0172398 A1 | 8/2005 | Smith et al. | 5/81.1 R |
| 2005/0251914 A1 | 11/2005 | Schaller et al. | 5/601 |
| 2005/0256435 A1 | 11/2005 | Hess | 602/2 |
| 2006/0001545 A1 | 1/2006 | Wolf | 340/573.1 |
| 2006/0021240 A1 | 2/2006 | Horgan | 33/366.11 |
| 2006/0031102 A1 | 2/2006 | Teller et al. | 705/3 |
| 2006/0089538 A1 | 4/2006 | Cuddihy et al. | 600/300 |
| 2006/0097983 A1 | 5/2006 | Haggman et al. | 345/156 |
| 2006/0116904 A1 | 6/2006 | Brem | 705/2 |
| 2006/0270949 A1 | 11/2006 | Mathie et al. | 600/595 |
| 2006/0279426 A1 | 12/2006 | Bonnet et al. | 340/573.1 |
| 2007/0000154 A1 | 1/2007 | Dibenedetto et al. | 36/132 |
| 2007/0038155 A1 | 2/2007 | Kelly, Jr. et al. | 600/595 |
| 2007/0115277 A1 | 5/2007 | Wang et al. | 345/419 |
| 2007/0118056 A1 | 5/2007 | Wang et al. | 600/595 |
| 2007/0130893 A1 | 6/2007 | Davies | 54/1 |
| 2007/0132597 A1 | 6/2007 | Rodgers | 340/573.1 |
| 2007/0159332 A1 | 7/2007 | Koblasz | 340/572.1 |
| 2007/0175949 A1 | 8/2007 | Shelton, IV et al. | 227/176.1 |
| 2007/0241261 A1 | 10/2007 | Wendt | 250/221 |
| 2008/0001735 A1 | 1/2008 | Tran | 340/539.22 |
| 2008/0031102 A1 | 2/2008 | Oettinger et al. | 369/44.28 |
| 2008/0103447 A1 | 5/2008 | Reggiardo et al. | 604/131 |
| 2008/0129518 A1 | 6/2008 | Carlton-foss | 340/573.1 |
| 2008/0272918 A1 | 11/2008 | Ingersoll | 340/573.1 |
| 2008/0275349 A1 | 11/2008 | Halperin et al. | 600/484 |
| 2009/0010178 A1 | 1/2009 | Tekippe | 370/254 |
| 2009/0024065 A1 | 1/2009 | Einarsson | 602/26 |
| 2009/0069642 A1 | 3/2009 | Gao et al. | 600/300 |
| 2009/0071249 A1 | 3/2009 | Kitazaki et al. | 73/514.33 |
| 2009/0099480 A1 | 4/2009 | Salgo et al. | 600/595 |
| 2009/0119843 A1 | 5/2009 | Rodgers et al. | 5/611 |
| 2009/0164250 A1 | 6/2009 | Hamilton et al. | 705/3 |
| 2009/0174565 A1 | 7/2009 | Chan et al. | 340/669 |
| 2009/0185763 A1 | 7/2009 | Park et al. | 382/311 |
| 2009/0237264 A1 | 9/2009 | Bobey et al. | 340/815.69 |
| 2009/0254003 A1 | 10/2009 | Buckman | 600/595 |
| 2009/0318908 A1 | 12/2009 | Van Pieterson et al. | 606/9 |
| 2009/0322763 A1 | 12/2009 | Bang et al. | 345/474 |
| 2010/0010385 A1 | 1/2010 | Skelton et al. | 600/595 |
| 2010/0049096 A1 | 2/2010 | Ten Kate | 600/595 |
| 2010/0081385 A1 | 4/2010 | Lin et al. | 455/41.3 |
| 2010/0121226 A1 | 5/2010 | Ten Kate et al. | 600/595 |
| 2010/0121227 A1 | 5/2010 | Stirling et al. | 600/595 |
| 2010/0156653 A1 | 6/2010 | Chaudhari et al. | 340/686.1 |
| 2010/0162832 A1 | 7/2010 | Brauers | 73/862.626 |
| 2010/0231376 A1 | 9/2010 | Hirose | 340/517 |
| 2010/0268122 A1 | 10/2010 | Drennan et al. | 600/587 |
| 2010/0298656 A1 | 11/2010 | Mccombie et al. | 600/301 |
| 2010/0298661 A1 | 11/2010 | Mccombie et al. | 600/301 |
| 2010/0298742 A1 | 11/2010 | Perlman et al. | 600/595 |
| 2011/0025493 A1 | 2/2011 | Papadopoulos et al. | 340/539.12 |

(56) References Cited

U.S. PATENT DOCUMENTS

| | | |
|---|---|---|
| 2011/0046498 A1 | 2/2011 | Klap et al. ............... 600/534 |
| 2011/0046499 A1 | 2/2011 | Klewer et al. ............ 600/534 |
| 2011/0050411 A1 | 3/2011 | Schuman et al. ...... 340/539.13 |
| 2011/0066007 A1 | 3/2011 | Banet et al. .............. 600/301 |
| 2011/0066009 A1 | 3/2011 | Moon et al. .............. 600/301 |
| 2011/0082672 A1 | 4/2011 | Hardigan ..................... 703/2 |
| 2011/0084806 A1 | 4/2011 | Perkins ..................... 340/10.1 |
| 2011/0112442 A1 | 5/2011 | Meger et al. .............. 600/595 |
| 2011/0156915 A1 | 6/2011 | Brauers et al. .......... 340/573.4 |
| 2011/0201972 A1 | 8/2011 | Ten Kate .................. 600/595 |
| 2011/0234395 A1 | 9/2011 | Johnson et al. ....... 340/539.12 |
| 2011/0245732 A1 | 10/2011 | Mravyan et al. .......... 600/587 |
| 2011/0263950 A1 | 10/2011 | Larson et al. ............. 600/301 |
| 2012/0029392 A1 | 2/2012 | Jin et al. ................... 600/595 |
| 2012/0057433 A1 | 3/2012 | Diduch et al. ............... 368/10 |
| 2012/0101770 A1 | 4/2012 | Grabiner et al. ........... 702/141 |
| 2012/0139722 A1 | 6/2012 | Wong et al. ........... 340/539.12 |
| 2012/0172685 A1 | 7/2012 | Gilbert ........................ 600/306 |
| 2012/0253142 A1 | 10/2012 | Meger et al. .............. 600/301 |
| 2012/0253485 A1 | 10/2012 | Weast et al. ................. 700/91 |
| 2012/0259577 A1 | 10/2012 | Ganyi ......................... 702/139 |
| 2012/0271654 A1 | 10/2012 | Croghan et al. ............... 705/3 |
| 2012/0277637 A1 | 11/2012 | Vahdatpour et al. ....... 600/595 |
| 2013/0006151 A1 | 1/2013 | Main et al. ................. 600/587 |
| 2013/0090571 A1 | 4/2013 | Nourani et al. ............ 600/587 |
| 2013/0096390 A1 | 4/2013 | Weller-brophy et al. .... 600/300 |
| 2013/0141233 A1 | 6/2013 | Jacobs et al. .............. 340/521 |
| 2014/0118138 A1 | 5/2014 | Cobelli et al. ........... 340/539.12 |
| 2014/0188638 A1 | 7/2014 | Jones et al. ................... 705/16 |
| 2014/0257057 A1 | 9/2014 | Reis Cunha et al. ....... 600/301 |
| 2014/0259414 A1 | 9/2014 | Hayes et al. ................... 5/611 |
| 2014/0313030 A1 | 10/2014 | Ten Kate et al. ........ 340/539.12 |
| 2015/0011263 A1 | 1/2015 | Itamoto et al. ............. 455/566 |
| 2015/0082542 A1 | 3/2015 | Hayes et al. ................... 5/600 |
| 2015/0094618 A1 | 4/2015 | Russell et al. .............. 600/587 |
| 2015/0121261 A1 | 4/2015 | Collado et al. ............. 715/764 |
| 2015/0136146 A1 | 5/2015 | Hood et al. ................. 128/845 |
| 2015/0164437 A1 | 6/2015 | Mccombie et al. ........ 600/301 |
| 2015/0302539 A1 | 10/2015 | Mazar et al. ................... 705/3 |
| 2015/0351981 A1 | 12/2015 | Sazonov .................. 297/217.2 |
| 2016/0157798 A1 | 6/2016 | Anderson et al. .......... 600/427 |
| 2016/0256080 A1 | 9/2016 | Shen et al. .................. 600/595 |
| 2017/0027498 A1 | 2/2017 | Larson et al. ............... 600/595 |
| 2017/0055896 A1 | 3/2017 | Al-ali et al. ................ 600/301 |

FOREIGN PATENT DOCUMENTS

| | | | |
|---|---|---|---|
| JP | 2003070768 A | 3/2003 | ............ A61B 5/107 |
| JP | 2003116858 A | 4/2003 | ............ A61B 10/00 |
| JP | 2004121837 A | 4/2004 | ............ A47C 19/04 |
| JP | 2004194709 A | 7/2004 | ............ A61G 7/00 |
| JP | 2004201758 A | 7/2004 | ............ A61B 5/00 |
| JP | 2006122376 A | 5/2006 | ............ A61B 5/22 |
| JP | 2006175206 A | 7/2006 | ............ A61B 5/107 |
| JP | 2006325683 A | 12/2006 | ............ A61B 5/00 |
| JP | 2007040848 A | 2/2007 | ............ A61B 5/11 |
| JP | 2008027030 A | 2/2008 | ............ A61B 5/00 |
| JP | 2008295644 A | 12/2008 | ............ A47C 21/00 |
| JP | 2010022723 A | 2/2010 | ............ A61B 5/028 |
| JP | 2010035579 A | 2/2010 | ............ A61G 12/00 |
| JP | 2011183121 A | 9/2011 | ............ A61B 5/11 |
| WO | 03/079898 A1 | 10/2003 | ............ A61B 5/11 |
| WO | WO 03/079898 A1 | 10/2003 | |
| WO | 2007/106040 A1 | 9/2007 | ............ A61G 7/057 |
| WO | 2007/119570 A1 | 10/2007 | ............ A01K 11/00 |
| WO | 2008/113556 A1 | 9/2008 | ............ A61B 5/11 |
| WO | 2010/105045 A2 | 9/2010 | ............ A61B 5/02 |
| WO | 2010/105203 A2 | 9/2010 | ............ A61B 5/02 |
| WO | 2010/111363 A2 | 9/2010 | ............ A61B 5/103 |
| WO | 2011/087807 A2 | 7/2011 | ............ A61B 5/0059 |
| WO | 2011/113070 A1 | 9/2011 | ............ A61B 5/002 |
| WO | 2012/037470 A1 | 3/2012 | ............ G01C 21/00 |
| WO | 2012/114298 A2 | 8/2012 | ............ A61B 5/03 |
| WO | 2013/042097 A1 | 3/2013 | ............ A61B 5/11 |
| WO | 2013/052123 A1 | 4/2013 | ............ A61B 5/103 |
| WO | 2013/109410 A1 | 7/2013 | ............ H04W 24/00 |
| WO | 2014/024094 A2 | 2/2014 | ............ A61G 7/057 |
| WO | 2015/054423 A1 | 4/2015 | ............ A61B 5/11 |
| WO | 2015/074007 A1 | 5/2015 | ............ A61B 5/00 |
| WO | 2016/077310 A1 | 5/2016 | ............ G06Q 50/22 |

OTHER PUBLICATIONS

Seiler, Walter O. et al., "Decubitus Ulcers: Preventive Techniques for the Elderly Patient," Geriatrics, vol. 40, No. 7, pp. 53-60, Jul. 1985.

Seiler, Walter O. et al., "Influence of the 30° Laterally Inclined Position and the 'Super Soft' 3-Piece Mattress on Skin Oxygen Tension on Areas of Maximum Pressure—Implications for Pressure Sore Prevention," Gerontology, vol. 32, pp. 158-166, 1986.

Braden, Barbara et al., "Braden Scale—for Predicting Pressure Sore Risk," Form 3166P, 1 page, © 1988.

Lord, M. et al., "Rehabilitation Engineering: Method for In-Shoe Shear Stress Measurement," Journal of Biomedical Engineering, vol. 14, pp. 181-186, May 1992.

Knox, Dorothy M. et al., "Effects of Different Turn Intervals on Skin of Healthy Older Adults," Advances in Wound Care, vol. 7, No. 1, pp. 48-56, Jan. 1994.

Colin, Denis et al., "Comparison of 90° and 30° Laterally Inclined Positions in the Prevention of Pressure Ulcers Using Transcutaneous Oxygen and Carbon Dioxide Pressures," Advances in Wound Care, vol. 9, No. 3, pp. 35-38, 1996.

DeFloor, Tom, "The Risk of Pressure Sores: A Conceptual Scheme," Journal of Clinical Nursing, vol. 8, pp. 206-216, May 10, 1998.

Lalonde, N. M. et al., "Effect of Different Tilt and Seat-To-Back Angles on Trunk, Pelvic, and Hip Orientations," Proceedings of the 22nd Annual RESNA Conference, 9 pages, Jun. 25, 1999.

Halfens, R.J.G. et al., "Validity and Reliability of the Braden Scale and the Influence of other Risk Factors: A Multi-Centre Prospective Study," International Journal of Nursing Studies, vol. 37, pp. 313-319, Aug. 30, 1999.

Wang, Jue et al., "A Compound Sensor for Biomechanical Analyses of Buttock Soft Tissue in Vivo," Journal of Rehabilitation Research and Development, vol. 37, No. 4, pp. 433-443, Dec. 14, 1999.

DeFloor, Tom, "The Effect of Position and Mattress on Interface Pressure," Applied Nursing Research, vol. 13, No. 1, pp. 2-11, Feb. 2000.

Keller, B.J. et al., "Pressure Ulcers in Intensive Care Patients: A Review of Risks and Prevention," Intensive Care Med, vol. 28, pp. 1379-1388, Sep. 7, 2002.

Anonymous, "By the Numbers: Braden Score Interventions," Advances in Skin & Wound Care, vol. 17, No1. 3, p. 150, Apr. 2004.

Lowne, D.R., "Designing a Low-Cost Mattress Sensor for Automated Body Position Classification," IEEE Engineering in Medicine and Biology 27th Annual Conference, pp. 6437-6440, 2005.

DeFloor, Tom et al., "The Effect of Various Combinations of Turning and Pressure Reducing Devices on the Incidence of Pressure Ulcers," International Journal of Nursing Studies, vol. 42, No. 1, pp. 37-46, Jan. 2005.

Okuwa, Mayumi et al., "Measuring the Pressure Applied to the Skin Surrounding Pressure Ulcers while Patients are Nursed in the 30° Position," Journal of Tissue Viability, vol. 15, No. 1, pp. 3-8, Jan. 2005.

DeFloor, Tom et al., "Pressure Ulcer Prevention and Repositioning," Science and Practice of Pressure Ulser Management, Chapter 8, pp. 67-73, 2006.

Papanikolaou, Panos et al., "Risk Assessment Scales for Pressure Ulcers: A Methodological Review," International Journal of Nursing Studies, vol. 44, pp. 285-296, Jan. 10, 2006.

Scanaill, Cliodhna Ní et al., "A Review of Approaches to Mobility Telemonitoring of the Elderly in Their Living Environment," Annals of Biomedical Engineering, vol. 34, No. 4, pp. 547-563, Mar. 21, 2006.

Vanderwee, K. et al., "Effectiveness of Turning with Unequal Time Intervals on the Incidence of Pressure Ulcer Lesions," Journal of Advanced Nursing, vol. 57, No. 1, pp. 59-68, Jul. 10, 2006.

(56) References Cited

OTHER PUBLICATIONS

Zijlstra, Wiebren et al., "Mobility Assessment in Older People: New Possibilities and Challenges," European Journal of Aging, vol. 4, pp. 3-12, Feb. 6, 2007.
Lyder, Courtney H. et al., "Chapter 12. Pressure Ulcers: A Patient Safety Issue," In *Patient Safety and Quality: An Evidence-Based Handbook for Nurses*, Agency for Research and Quality, 33 Pages, Apr. 2008.
Peterson, M. et al., "Effects of Elevating the Head of Bed on Interface Pressure in Volunteers," Critical Care Medicine, vol. 36, No. 11, pp. 3038-3042, Nov. 2008.
Wai, A.A. et al., "Sleeping Patterns Observation for Bedsores and Bed-Side Falls Prevention," Annual International Conference of the IEEE Engineering in Medicine and Biology Society, pp. 6087-6090, 2009.
Mimura, Maki et al., "Mechanism Leading to the Development of Pressure Ulcers Based on Shear Force and Pressures During a Bed Operation: Influence of Body Types, Body Positions, and Knee Positions," Wound Repair and Regeneration, vol. 17, pp. 789-796, Jul. 27, 2009.
Hsia, C.C. et al., "Analysis and Comparison of Sleeping Posture Classification Methods using Pressure Sensitive Bed System," Annual International Conference of the IEEE Engineering in Medicine and Biology Society, pp. 6131-6134, Sep. 2009.
Yip, Marcus et al., "A Flexible Pressure Monitoring System for Pressure Ulcer Prevention," 31st Annual International Conference of the IEEE EMBS, Minneapolis, Minnesota, pp. 1212-1215, Sep. 2, 2009.
Kraft, Peter et al., "Christmas 2009: Young and Old: Lying Obliquely—A Clinical Sign of Cognitive Impairment: Cross Sectional Obersvational Study," BMJ, vol. 339, 5 pages, Nov. 17, 2009.
Shabshin, Nogah et al., "Evaluation of the Effect of Trunk Tilt on Compressive Soft Tissue Deformations Under the Ischial Tuberosities Using Weight-Bearing MRI," Clinical Biometrics, vol. 25, Issue 5, pp. 402-408, Jan. 28, 2010.
Ostadabbas, Sarah et al., "Pressure Ulcer Prevention: An Efficient Turning Schedule for Bed-Bound Patients," IEEE/NIH Life Science Systems and Applications Workshop, pp. 159-162, 2011.
Cox, Jill, "Predictors of Pressure Ulcers in Adult Critical Care Patients," American Journal of Critical Care, vol. 20, No. 5, pp. 364-374, Sep. 2011.
Dhillon, Marshal et al., "Towards the Prevention of Pressure Ulcers with a Wearable Patient Posture Monitor Based on Adaptive Accelerometer Alignment," 34th Annual International Conference of the IEEE EMBS San Diego, CA, pp. 4513-4516, Aug. 28, 2012.
International Search Report and Written Opinion, Application No. PCT/US2012/00488, 6 pages, dated Jan. 23, 2013.
International Search Report and Written Opinion, Application No. PCT/US2014/066016, 6 pages, dated Feb. 11, 2015.
U.S. Non-Final Office Action, U.S. Appl. No. 15/028,018, 22 pages, dated Nov. 14, 2016.
U.S. Final Office Action, U.S. Appl. No. 14/244,720, 39 pages, dated Dec. 1, 2016.
Japanese Office Action, Application No. 2012557312, 9 pages, dated Jan. 10, 2017.
U.S. Non-Final Office Action, U.S. Appl. No. 15/036,782, 28 pages, dated Mar. 29, 2017.
U.S. Non-Final Office Action, U.S. Appl. No. 14/244,720, 39 pages, dated Apr. 19, 2017.
U.S. Non-Final Office Action, U.S. Appl. No. 15/187,516, 42 pages, dated May 11, 2017.
U.S. Non-Final Office Action, U.S. Appl. No. 15/173,612, 38 pages, dated May 12, 2017.
European Invitation to Pay Additional Fees, Application No. 14862053.7, 13 pages, dated May 23, 2017.
European Partial Supplementary Search Report, Application No. 14851948.1, 17 pages, dated Jun. 8, 2017.
International Search Report and Written Opinion, Application No. PCT/US2017/025832, 11 pages, dated Jun. 21, 2017.
U.S. Non-Final Office Action, U.S. Appl. No. 15/601,593, 31 pages, dated Aug. 15, 2017.
Invitation to Pay Additional Fees and Partial International Search Report, Application No. PCT/US2017/037589, 15 pages, dated Aug. 23, 2017.
European Extended Search Report, Application No. 14862053.7, 11 pages, dated Sep. 7, 2017.
U.S. Non-Final Office Action, U.S. Appl. No. 15/487,663, 26 pages, dated Sep. 14, 2017.
European Extended Search Report, Application No. 14851948.1, 13 pages, dated Sep. 19, 2017.
International Search Report and Written Opinion, Application No. PCT/US2017/038511, 12 pages, dated Oct. 5, 2017.
International Search Report and Written Opinion, Application No. PCT/US2017/037589, 19 pages, dated Oct. 16, 2017.
U.S. Final Office Action, U.S. Appl. No. 15/173,612, 51 pages, dated Nov. 14, 2017.
Japanese Office Action, Application No. 2016530839, 6 pages, dated Dec. 12, 2017.
U.S. Non-Final Office Action, U.S. Appl. No. 15/696,908, 28 pages, dated Dec. 22, 2017.
U.S. Non-Final Office Action, U.S. Appl. No. 15/654,928, 47 pages, dated Jan. 25, 2018.
U.S. Final Office Action, U.S. Appl. No. 15/487,663, 22 pages, dated Jan. 30, 2018.
European Extended Search Report, Application No. 17204228.5, 6 pages, dated Mar. 28, 2018.
U.S. Non-Final Office Action, U.S. Appl. No. 15/186,344, 23 pages, dated Apr. 6, 2018.
U.S. Final Office Action, U.S. Appl. No. 15/036,782, 57 pages, dated May 11, 2018.
Japanese Office Action, Application No. 2016530839, 4 pages, dated Jun. 12, 2018.
U.S. Non-Final Office Action, U.S. Appl. No. 15/173,595, 26 pages, dated Jul. 10, 2018.
U.S. Final Office Action, U.S. Appl. No. 15/654,928, 46 pages, dated Jul. 11, 2018.
U.S. Non-Final Office Action, U.S. Appl. No. 15/183,739, 25 pages, dated Aug. 9, 2018.
U.S. Final Office Action, U.S. Appl. No. 14/244,720, 80 pages, dated Aug. 13, 2018.
U.S. Non-Final Office Action, U.S. Appl. No. 13/070,189, 5 pages, dated Sep. 10, 2018.
U.S. Final Office Action, U.S. Appl. No. 15/696,908, 34 pages, dated Sep. 21, 2018.
International Search Report and Written Opinion, Application No. PCT/US2018/041552, 12 pages, dated Oct. 4, 2018.
U.S. Non-Final Office Action, U.S. Appl. No. 15/654,928, 29 pages, dated Nov. 6, 2018.
U.S. Non-Final Office Action, U.S. Appl. No. 15/173,595, 14 pages, dated Dec. 4, 2018.
U.S. Final Office Action, U.S. Appl. No. 15/186,344, 20 pages, dated Jan. 3, 2019.
U.S. Non-Final Office Action, U.S. Appl. No. 14/244,720, 21 pages, dated Jan. 15, 2019.
U.S. Non-Final Office Action, U.S. Appl. No. 15/173,612, 54 pages, dated Jan. 17, 2019.
European Office Action, Application No. 17204228.5, 5 pages, dated Jan. 29, 2019.
U.S. Notice of Allowance, U.S. Appl. No. 15/186,344, 20 pages, dated Feb. 13, 2019.
U.S. Final Office Action, U.S. Appl. No. 15/183,739, 30 pages, dated Feb. 19, 2019.
U.S. Notice of Allowance, U.S. Appl. No. 15/173,595, 11 pages, dated Feb. 27, 2019.
U.S. Non-Final Office Action, U.S. Appl. No. 15/189,086, 47 pages, dated Mar. 30, 2019.
U.S. Non-Final Office Action, U.S. Appl. No. 15/186,542, 32 pages, dated Mar. 22, 2019.
U.S. Final Office Action, U.S. Appl. No. 15/654,928, 19 pages, dated May 10, 2019.
U.S. Non-Final Office Action, U.S. Appl. No. 13/070,189, 50 pages, dated May 15, 2019.

(56) References Cited

OTHER PUBLICATIONS

U.S. Non-Final Office Action, U.S. Appl. No. 15/183,739, 18 pages, dated Jun. 28, 2019.
European Office Action, Application No. 17204228.5, 5 pages, dated Jul. 8, 2019.
U.S. Final Office Action, U.S. Appl. No. 14/244,720, 26 pages, dated Jul. 30, 2019.
U.S. Final Office Action, U.S. Appl. No. 15/173,612, 32 pages, dated Aug. 22, 2019.
U.S. Final Office Action, U.S. Appl. No. 15/189,086, 19 pages, dated Aug. 28, 2019.
Japanese Office Action, Application No. 2018169327, 12 pages, dated Sep. 9, 2019.
U.S. Non-Final Office Action, U.S. Appl. No. 15/696,908, 43 pages, dated Oct. 2, 2019.
U.S. Final Office Action, U.S. Appl. No. 15/186,542, 22 pages, dated Oct. 7, 2019.
U.S. Final Office Action, U.S. Appl. No. 13/070,189, 27 pages, dated Nov. 29, 2019.
European Office Action, Application No. 17204228.5, 4 pages, dated Dec. 20, 2019.
U.S. Non-Final Office Action, U.S. Appl. No. 15/423,665, 13 pages, dated Jan. 10, 2020.
U.S. Non-Final Office Action, U.S. Appl. No. 15/173,612, 23 pages, dated Jan. 15, 2020.
U.S. Final Office Action, U.S. Appl. No. 15/696,908, 23 pages, dated Mar. 5, 2020.
U.S. Non-Final Office Action, U.S. Appl. No. 14/244,720, 24 pages, dated Mar. 19, 2020.
U.S. Non-Final Office Action, U.S. Appl. No. 15/186,542, 28 pages, dated Apr. 8, 2020.
U.S. Non-Final Office Action, U.S. Appl. No. 16/380,811, 27 pages, dated Jun. 23, 2020.
U.S. Non-Final Office Action, U.S. Appl. No. 15/935,385, 26 pages, dated Jul. 15, 2020.
Japanese Office Action, Application No. 2019159408, 7 pages, dated Jul. 20, 2020.
U.S. Final Office Action, U.S. Appl. No. 15/189,086, 23 pages, dated Aug. 10, 2020.
U.S. Final Office Action, U.S. Appl. No. 14/244,720, 17 pages, dated Aug. 10, 2020.
U.S. Final Office Action, U.S. Appl. No. 15/186,542, 24 pages, dated Aug. 24, 2020.
U.S. Non-Final Office Action, U.S. Appl. No. 16/548,553, 22 pages, dated Aug. 28, 2020.
"Progressively," Merriam-Webster.com, https://www.merriam-webster.com/dictionary/progressively, 8 pages, Retrieved on Nov. 9, 2020.
U.S. Non-Final Office Action, U.S. Appl. No. 15/186,542, 18 pages, dated Nov. 17, 2020.
U.S. Non-Final Office Action, U.S. Appl. No. 15/189,086, 40 pages, dated Dec. 16, 2020.
U.S. Non-Final Office Action, U.S. Appl. No. 16/820,403, 27 pages, dated Dec. 24, 2020.
U.S. Final Office Action, U.S. Appl. No. 15/935,385, 28 pages, dated Feb. 8, 2021.
Young, Trudie, "The 30° Tilt Position Vs. The 90° Lateral and Supine Positions in Reducing the Incidence of Non-Blanching Erythema in a Hospital Inpatient Population: A Randomized Controlled Trial," Journal of Tissue Viability, vol. 14, No. 3, pp. 88-96, Jul. 3, 2004.
DeFloor, Tom et al., "Science and Practice of Pressure Ulcer Medicine," Springs, 214 pages, May 26, 2014.
Moore, Zena et al., "A Randomized Controlled Clinical Trial of Repositioning, Using the 30° Tilt, for the Prevention of Pressure Ulcers," Journal of Clinical Nursing, vol. 20, pp. 2633-2644, Jan. 19, 2011.
European Extended Search Report, Application No. 20206825.0, 7 pages, dated Jan. 14, 2021.
U.S. Final Office Action, U.S. Appl. No. 15/189,086, 29 pages, dated May 3, 2021.
U.S. Non-Final Office Action, U.S. Appl. No. 15/935,385, 33 pages, dated Jun. 28, 2021.
U.S. Final Office Action, U.S. Appl. No. 16/820,403, 22 pages, dated Jul. 2, 2021.
Japanese Office Action, Application No. 2018565819, 6 pages, dated Jul. 5, 2021.
U.S. Non-Final Office Action, U.S. Appl. No. 15/189,086, 23 pages, dated Jul. 30, 2021.
U.S. Non-Final Office Action, U.S. Appl. No. 15/696,908, 54 pages, dated Sep. 2, 2021.
Canadian Office Action, Application No. 2926709, 4 pages, dated Sep. 16, 2021.

* cited by examiner

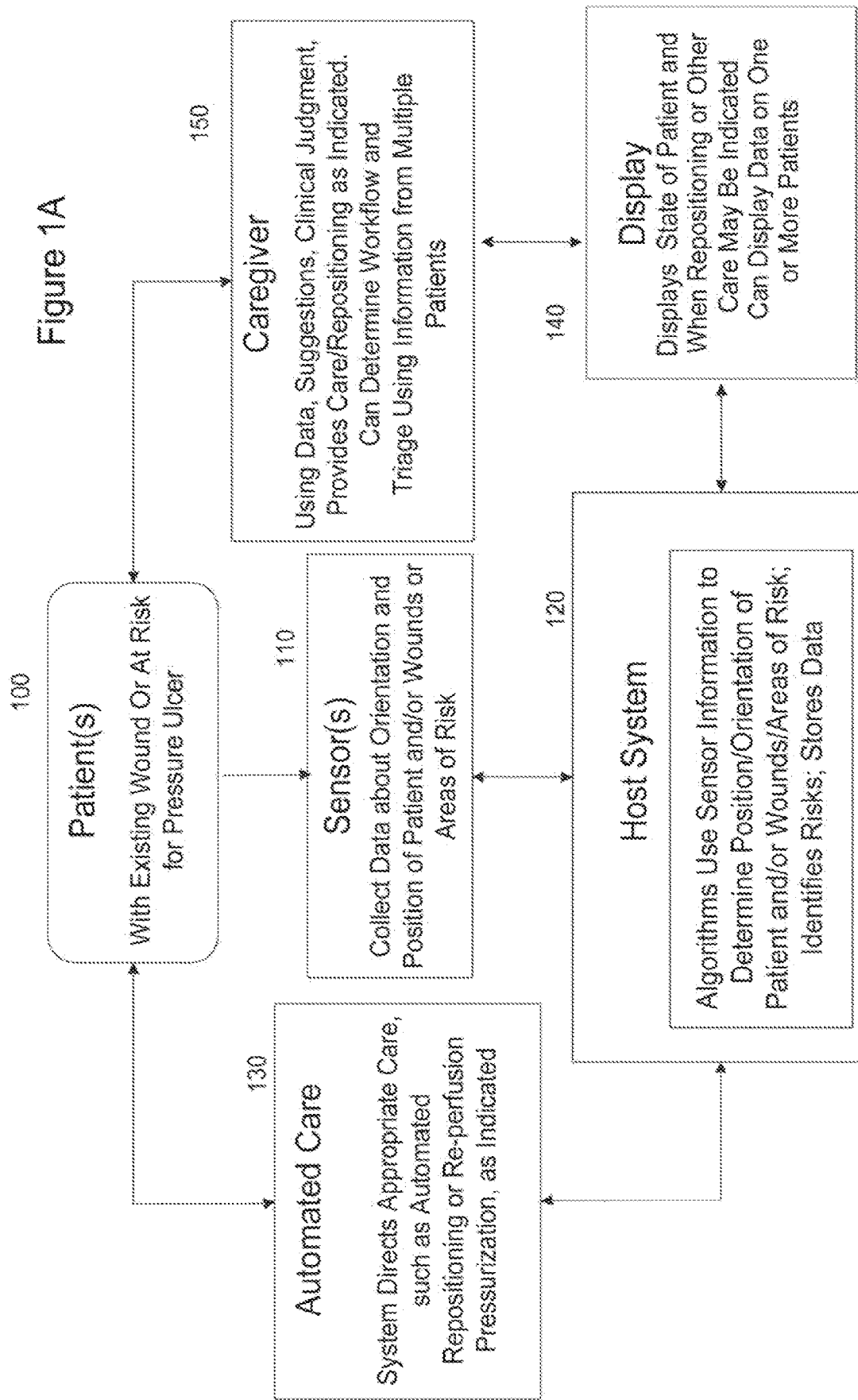

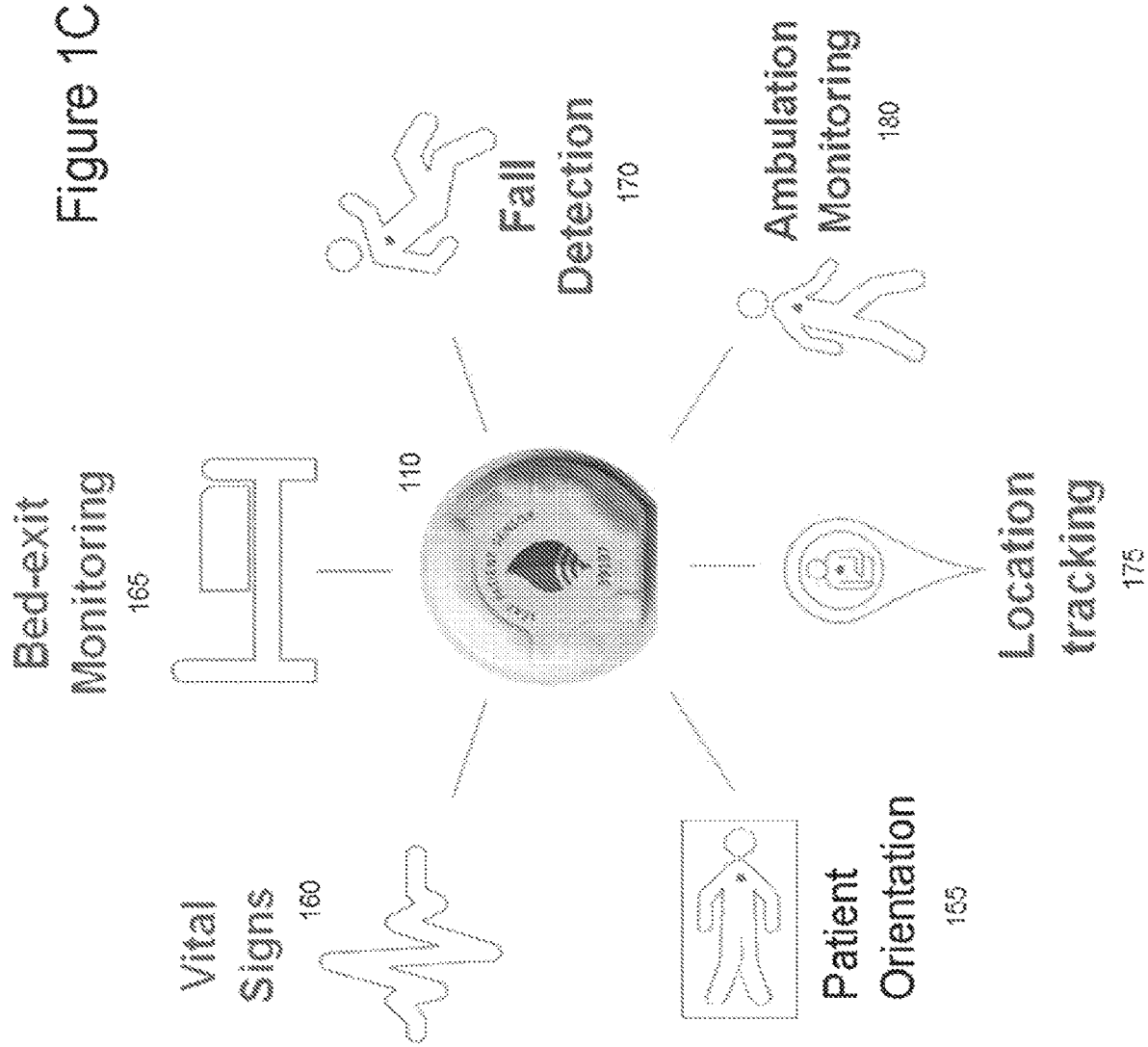

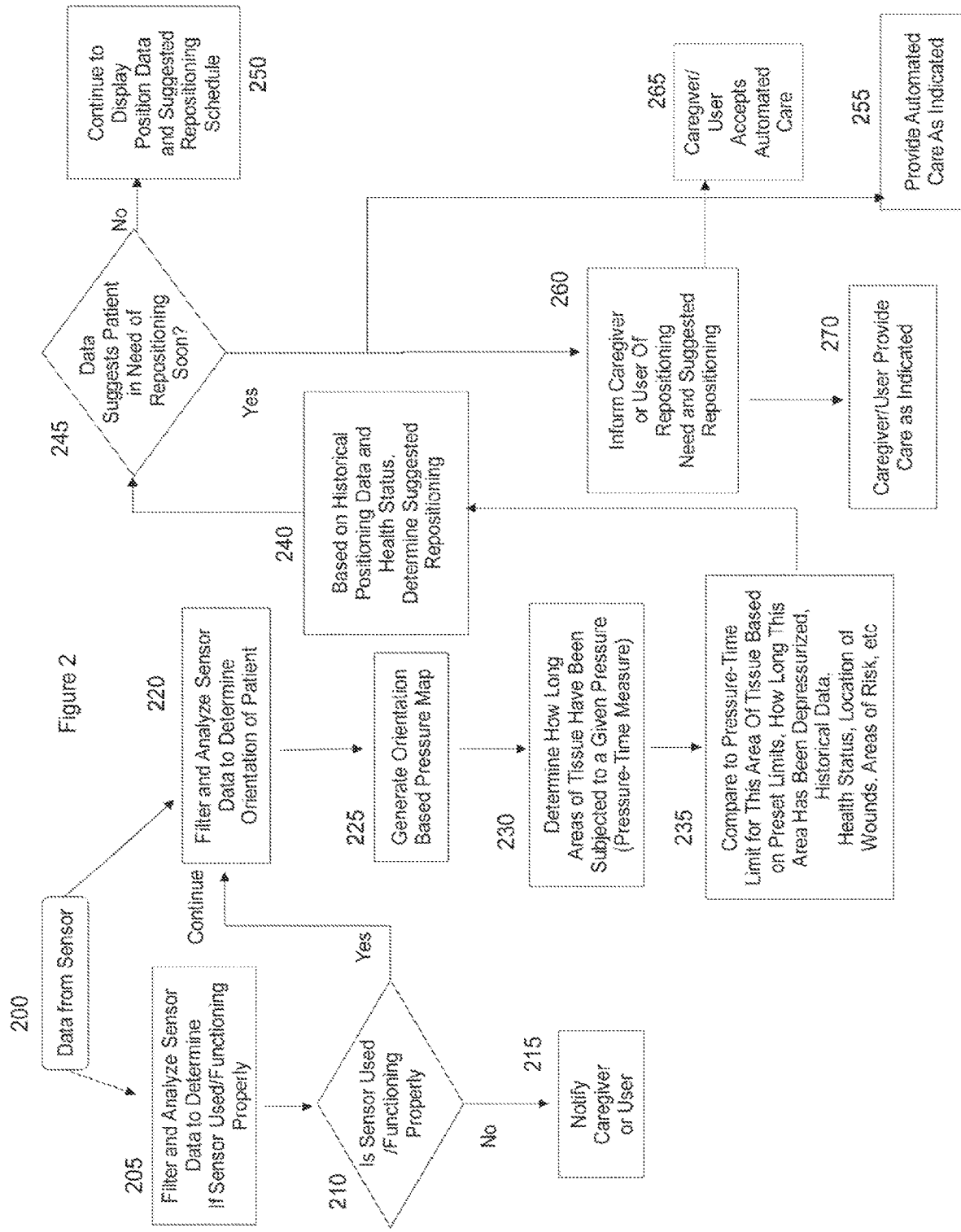

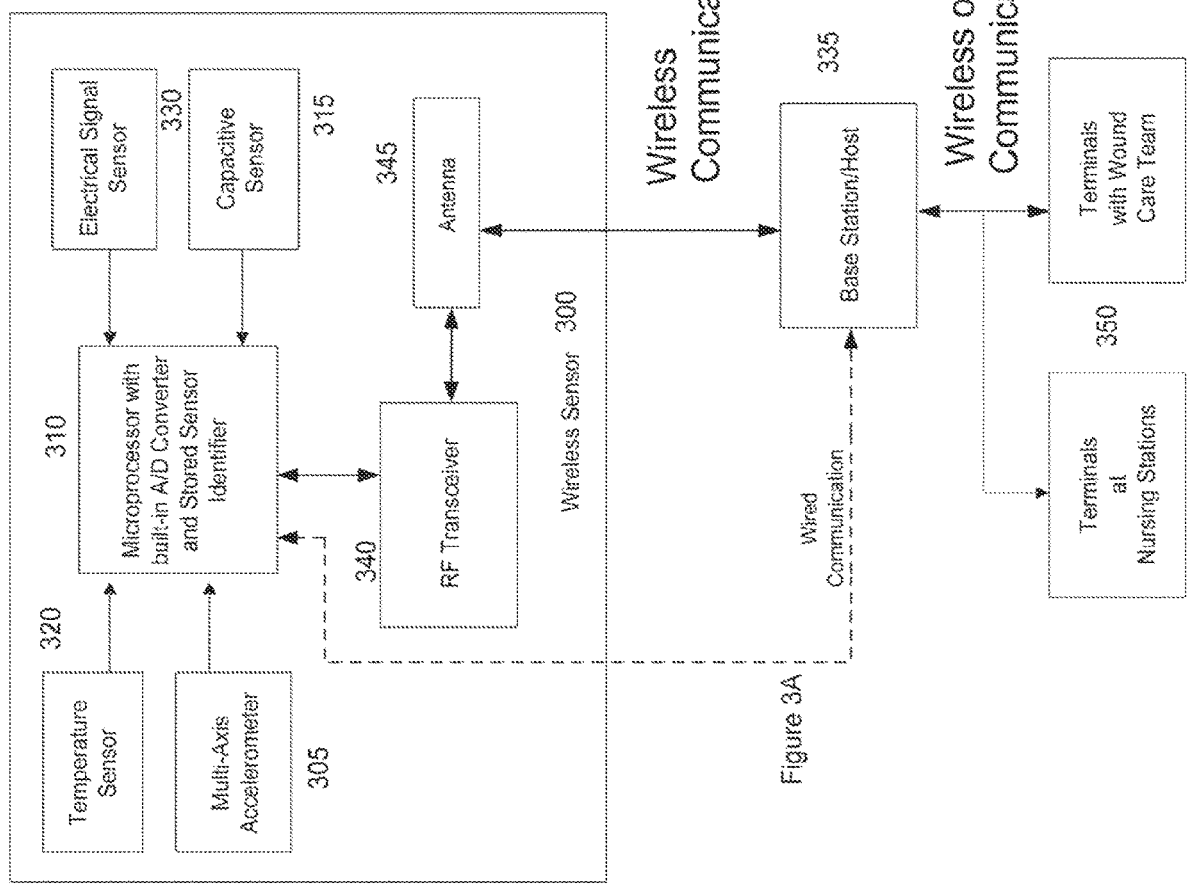

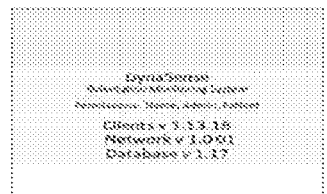
Figure 18
Figure 19
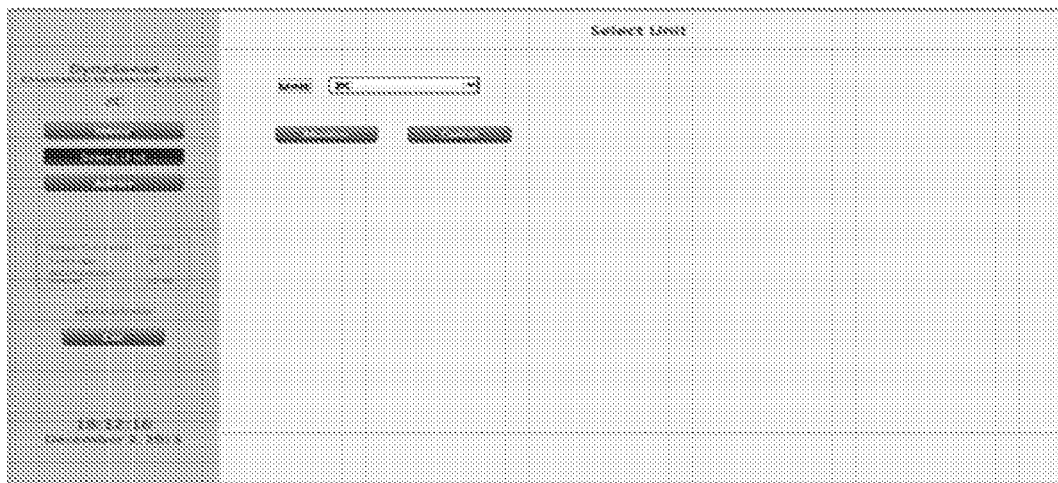

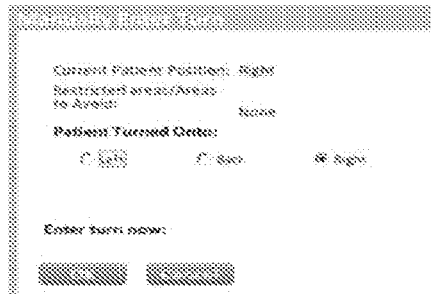
Figure 26
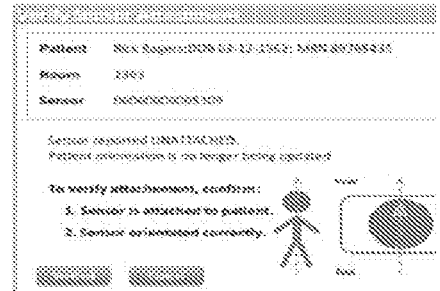
Figure 27
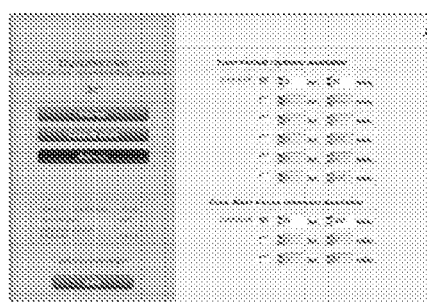
Figure 28B
Figure 28A
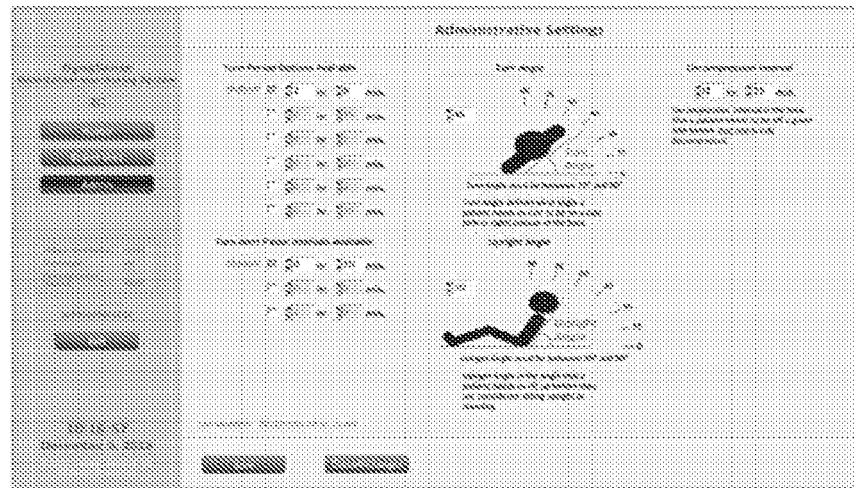

SYSTEMS AND METHODS FOR MANAGING PRESSURIZATION TIMERS FOR MONITORING AND/OR MANAGING A PERSON'S POSITION

RELATED APPLICATIONS

This application is a Continuation of U.S. patent application Ser. No. 16/548,553 filed Aug. 22, 2019, now U.S. Pat. No. 10,912,491, which is a Continuation of U.S. patent application Ser. No. 15/423,665 filed Feb. 3, 2017, which is a Continuation-in-Part (CIP) of (a) U.S. patent application Ser. No. 14/543,887 filed Nov. 17, 2014, now U.S. Pat. No. 9,728,061, which claims the benefit of (i) U.S. Provisional Patent Application Ser. No. 61/905,106, filed Nov. 15, 2013; and (ii) U.S. Provisional Patent Application Ser. No. 62/047,642, filed Sep. 8, 2014; and (b) U.S. patent application Ser. No. 13/070,189, filed Mar. 23, 2011, now U.S. Pat. No. 10,729,357, which claims the benefit of (i) U.S. Provisional Patent Application Ser. No. 61/438,732, filed Feb. 2, 2011; (ii) U.S. Provisional Patent Application Ser. No. 61/326,664, filed Apr. 22, 2010; (iii) U.S. Provisional Patent Application Ser. No. 61/411,647, filed Nov. 9, 2010; (iv) U.S. Provisional Patent Application Ser. No. 61/393,364, filed Oct. 15, 2010; and (v) U.S. Provisional Patent Application Ser. No. 61/373,260, filed Aug. 12, 2010. All of the applications listed above are incorporated herein by reference for all purposes.

TECHNICAL FIELD

Aspects of the present invention relate generally to systems, devices and methods for the detection, prevention and treatment of pressure-induced ischemia and other issues affecting the health of a patient including bed exits and falls, and more particularly relates to systems, devices and methods for such detection, prevention, and treatment, communicating of relevant information to a host, and providing either appropriate information to a caregiver to facilitate proper management of the patient or device instructions for providing automated care.

BACKGROUND

Pressure ulcers are a vast and growing problem in the United States and account for ~$10 billion dollars in annual health care spending. In 2008, the Centers for Medicare & Medicaid Services discontinued reimbursement for hospital-acquired pressure ulcers (HAPUs), thus increasing the demand for early-stage prevention. Each year, over 1 million patients will suffer from a hospital-acquired pressure ulcer. Pressure ulcers occur most commonly in the elderly, which is the fastest-growing segment of the population. As a result, the number of patients at risk for developing pressure ulcers is expected to increase dramatically in the coming decades. Given the tremendous burden that pressure ulcers place on the healthcare system, there is a substantial need for improved prevention methods.

Pressure ulcers, also known as bedsores, can form when there is sustained pressure on a given area of the body. This unrelieved pressure causes compression of tissues and impairs blood flow to affected areas. If the surface pressure is not relieved, the resulting shortage of blood flow can lead to localized tissue damage and cell death. Pressure ulcers initially appear as areas of reddened skin, but can quickly develop into large open wounds if left untreated.

Pressure ulcers are a source of significant morbidity and mortality for patients. Pressure ulcer treatment begins with a comprehensive review of a patient's general health and an assessment of their wound. General treatment principles include positioning patients such that little or no pressure is placed on the ulcer, using pressure-relieving physical support apparatuses, optimizing nutritional status, and utilizing a myriad of advanced wound care modalities and wound dressing technologies. More specific treatment goals depend on the stage of the pressure ulcer, and range from applying skin protective dressings to surgical closure of the wound and skin grafting. The development of a hospital-acquired pressure ulcer may highlight the need to review, refine and intensify an institution's pressure ulcer prevention procedures.

To prevent pressure ulcers, the currently accepted standard of care is to turn high-risk patients at least every 2 hours, day and night. In many healthcare facilities, such a turning schedule can be difficult to maintain. Studies have shown that caregiver compliance with patient turning protocols is low and a high percentage of patients are not being turned appropriately.

Some explanations for this low compliance include difficulty monitoring patient position, ineffective turn reminders/alerts, and sub-optimal caregiver staffing ratios—all of which hinder efforts to prevent pressure ulcers. To further exacerbate the problem, as the population ages, the percent of patients requiring turning is increasing, and yet there is a growing shortage of nursing staff, making it increasingly difficult to maintain compliance with prescribed turning schedules.

In addition, for patients with ambulatory challenges, bed exits and falls can present a serious risk of injury. Such bed exits and falls can present significant care and liability issues for hospitals, assisted living institutions, hospices, and regular homes where a patient is being cared for. Elderly patients, or patients who are disoriented, or patients who have overestimated their condition, all too frequently seek to exit their beds when their physical abilities are not at the level necessary to either stand up or walk.

Bed exits and falls have in the past proven particularly challenging to manage, because prompt detection has been difficult. Monitoring systems for bed exits have proven unreliable, at least in part because such systems typically do not detect the preliminary movements that indicate a forthcoming exit by a patient who is likely to fall upon exiting the bed. Likewise, systems for detecting falls have not had great success, in part because falls can occur slowly, and involve relatively short distances between the bed and either the floor or some intermediate object.

The costs associated with a fall can be enormous, including loss of life or serious injury for the patient. From an economic standpoint, hospitals incur greatly increased costs in caring for patients injured due to a fall. Moreover, such costs are typically not reimbursed by insurance, as these hospital-acquired injuries are considered preventable. For some patients, particularly those who are easily disoriented, such as Alzheimers or dementia patients, an unexpected bed exit by even an ambulatory patient can result in that patient going missing, leading to significant consequences to both the patient and the caregiver There is a long-felt, definite and even urgent need for a system, method and device that helps to prevent, detect, and/or treat pressure-induced ischemia and pressure ulcers by optimizing surface pressure at areas of compromised tissue perfusion. Various aspects of the present invention accomplish these objectives and substantially depart from the conventional concepts and designs of the prior art.

SUMMARY

To address the need for improved pressure ulcer prevention and treatment methods, some embodiments disclosed herein provide systems, methods and devices for monitoring and coordinating patient turning efforts that enable more efficient and effective patient care. Broadly, the systems, methods and devices disclosed herein provide caregivers with information regarding a patient's position over time, thus enabling them to easily identify which patients are turning adequately on their own and which patients are in need of a caregiver assisted turn. In such a manner, the present invention allows caregivers to focus their attention on those who need it most, while at the same time ensuring that no patient is neglected. Furthermore, the present invention can intelligently optimize and coordinate turning schedules for a large group of patients and help prioritize patient turning needs.

In addition, other embodiments disclosed herein provide systems, methods and devices for monitoring for a patient fall or a patient exit from a physical support apparatus, e.g., a bed, chair, or other apparatus or structure designed to physically support a patient.

For example, one embodiment provides a system for monitoring a person, including a person-worn sensor device comprising at least one sensor and configured to collect sensor data, the at least one sensor comprising an accelerometer; and a processor in communication with the person-worn sensor device and configured to determine or access an orientation of a physical support apparatus comprising a bed, table, chair, or other structure configured to support the person at least partially off a floor or ground; receive sensor data collected by the person-worn sensor device; calculate an orientation of the person relative to the physical support apparatus based on (a) the orientation of the physical support structure and (b) the sensor data collected by the person-worn sensor device; and identify a physical support structure exit condition based at least on the determined orientation of the person relative to the physical support structure, wherein the physical support structure exit condition comprises an occurrence or anticipated occurrence of the person exiting the physical support structure.

In one embodiment, the person-worn sensor device comprises a plurality of accelerometers.

In one embodiment, the person-worn sensor device comprises the accelerometer and at least one of a magnetometer or an altimeter.

In one embodiment, the person-worn sensor device comprises at least two sensors selected from the group consisting of an accelerometer, a magnetometer, and an altimeter.

In one embodiment, calculating an orientation of the person relative to the physical support apparatus comprises at least one of calculating a physical orientation, an angular orientation, or a compass orientation of the person relative to the physical support apparatus.

In one embodiment, the processor is configured to determine or access at least one of a physical orientation, an angular orientation, or a compass orientation of the physical support structure, and calculate the orientation of the person relative to the physical support structure based on (a) the physical orientation, angular orientation, or compass orientation of the physical support structure and (b) the sensor data collected by the person-worn sensor.

In one embodiment, the processor is configured to determine or access an angular orientation of the physical support structure, and calculate the orientation of the person relative to the physical support structure based on the angular orientation of the physical support structure and the sensor data collected by the person-worn sensor.

In one embodiment, the processor is configured to determine or access a compass orientation of the physical support structure, and calculate the orientation of the person relative to the physical support structure based on the compass orientation of the physical support structure and the sensor data collected by the person-worn sensor.

In one embodiment, determining or accessing an orientation of the physical support structure comprises determining at least one of a physical orientation, an angular orientation, or a compass orientation of the physical support structure using an accelerometer, magnetometer, or other sensor associated with the physical support structure.

In one embodiment, determining or accessing an orientation of the physical support structure comprises monitoring a reference orientation of the person over time based on sensor data collected by the person-worn sensor device, and determining a physical orientation of the physical support structure based on the monitored reference orientation of the person.

In one embodiment, identifying the physical support structure exit condition comprises determining an anticipated imminent physical support structure exit by the person.

In one embodiment, identifying the physical support structure exit condition comprises determining a probability of a physical support structure exit by the person.

In one embodiment, the person-worn sensor device is affixed directly to the person or secured to or embedded in an article worn by the person.

In one embodiment, the processor is provided in the person-worn sensor device.

In another embodiment, the processor is provided in a processing device distinct from the person-worn sensor device, and wherein receiving, at the processor, sensor data collected by the person-worn sensor device comprises receiving the sensor data at the processor directly or indirectly via a wireless transmission from the person-worn sensor device.

In one embodiment, the system further includes at least one relay antenna device distinct from the person-worn sensor device and the processing device, and configured to communicate sensor data collected by the person-worn sensor device from the person-worn sensor device to the processing device.

In one embodiment, at least one of such relay antenna device is embodied in a smartphone, smart watch, laptop computer, tablet computer, or other handheld mobile device.

Another embodiment provides a system for monitoring a person, including a processor and computer instructions stored in non-transitory computer readable media and executable by the processor to: receive sensor data from a person-worn sensor device comprising at least one sensor, the at least one sensor comprising an accelerometer; determine or access an orientation of a physical support apparatus comprising a bed, table, chair, or other structure configured to support the person at least partially off a floor or ground; calculate an orientation of the person relative to the physical support apparatus based on (a) the orientation of the physical support structure and (b) the sensor data received from the person-worn sensor device; and identify a physical support structure exit condition based at least on the determined orientation of the person relative to the physical support structure, wherein the physical support structure exit condition comprises an occurrence or anticipated occurrence of the person exiting the physical support structure.

Another embodiment provides a method for monitoring a person, the method including receiving, by a processor, sensor data from a person-worn sensor device comprising at least one sensor, the at least one sensor comprising an accelerometer; determining or accessing, by the processor, an orientation of a physical support apparatus comprising a bed, table, chair, or other structure configured to support the person at least partially off a floor or ground; calculating, by the processor, an orientation of the person relative to the physical support apparatus based on (a) the orientation of the physical support structure and (b) the sensor data received from the person-worn sensor device; and identifying, by the processor, a physical support structure exit condition based at least on the determined orientation of the person relative to the physical support structure, wherein the physical support structure exit condition comprises an occurrence or anticipated occurrence of the person exiting the physical support structure.

Another embodiment provides a method for monitoring a person, including collecting sensor data regarding the person by a person-worn sensor device affixed directly to the person or secured to or embedded in an article worn by the person, the sensor data comprising at least acceleration data collected by an accelerometer of the person-worn sensor device; calculating an angular orientation of the person relative to a physical support apparatus based at least on the sensor data collected by the person-worn sensor device, wherein the physical support apparatus comprising a bed, table, chair, or other structure configured to support the person at least partially off a floor or ground; and identifying a physical support structure exit condition based at least on the determined angular orientation of the person relative to the physical support structure, wherein the physical support structure exit condition comprises an occurrence or anticipated occurrence of the person exiting the physical support structure.

Another embodiment provides a method for monitoring a person, including receiving, by a processor, sensor data from a person-worn sensor device comprising at least one sensor, the at least one sensor comprising an accelerometer; determining or accessing, by the processor, an orientation of a physical support apparatus comprising a bed, table, chair, or other structure configured to support the person at least partially off a floor or ground; calculating, by the processor, an orientation of the person relative to the physical support apparatus based on (a) the orientation of the physical support structure and (b) the sensor data received from the person-worn sensor device; comparing (a) the calculated orientation of the person relative to the physical support apparatus to (b) an orientation threshold value; and generating an alert in response to determining that the calculated orientation of the person relative to the physical support apparatus exceeds the orientation threshold value.

Another embodiment provides a system for monitoring a person, including a person-worn sensor device worn by or otherwise secured to the person, the person-worn sensor device comprising at least one sensor configured to collect person altitude data indicating an altitude or changes in altitude of the person, and collect person acceleration data including at least one of a static acceleration or a dynamic acceleration of the person; and a processor configured to receive person altitude data and person acceleration data collected by the person-worn sensor device; determine a relative altitude of the person based on (a) the collected person altitude data and (b) a reference altitude; and identify an alert condition based at least on (a) the determined relative altitude of the person, as determined based on the collected person altitude data and the reference altitude, and (b) the collected person acceleration data, wherein the alert condition indicates at least one of a fall by the person or an occurrence or anticipated occurrence of the person exiting a physical support structure configured to physically support the person.

Some embodiments of the present invention provide a lightweight multi-function sensor that can be easily affixed to a patient. In an embodiment, the sensor includes a multi-axis accelerometer, together with other logic for monitoring patient turns and related physical characteristics of the patient. In another embodiment, the sensor further includes a magnetometer and an altimeter. Further, the sensor communicates with a network of receivers, which may in an embodiment be relay antennas forming a mesh network. The sensor can, in at least some embodiment, be a lightweight, single use, disposable sensor affixed to the patient by means of a medical adhesive.

As discussed in greater detail hereinafter, patient orientation can be determined by the proper placement of the sensor on the torso of a patient. In one embodiment, the sensor comprises in part a three-axis accelerometer which, together with the algorithms disclosed herein, determines the orientation of the patient. Indicia on the sensor is used in some embodiments to simplify determining the orientation of the sensor on the patient.

In an embodiment, a system of the present invention comprises a host system for receiving data from a wireless sensor, together with storage for maintaining historical information about the patient. The historical patient data is used in connection with the algorithms processed in a processing unit to make recommendations to a caregiver, or, in the case of automated care systems, to enable the effectuation of the automated care. Patient-specific data can be provided to the system by any or all of being developed algorithmically, heuristically, or through manual entry.

In an aspect of the invention, some embodiments employ a mesh network for monitoring of various patient activities including patient orientation, location, potential or actual bed exits, and falls. In at least some embodiments, the addition of a sensor to the network, and the self-enabling structure of the network elements, can be achieved automatically, although manual configuration is also possible in some embodiments.

In the present invention, an embodiment of the sensor also includes a magnetometer and an altimeter. Small, low-power versions of such devices are available from a plurality of sources. The magnetometer permits determination of the direction a patient is facing, particularly when sitting up. A sudden change in magnetometer reading can indicate a patient attempting a bed exit. For many patients with limited mobility, the process of exiting the bed proceeds slowly, such that an alarm triggered by virtue of the change in magnetometer reading (which can in some embodiments be combined with accelerometer and altimeter data) allows a caregiver time to reach the patient before a bed exit actually occurs.

The altimeter provides an indication of the relative height of the patient-worn sensor. While low cost altimeters are often inaccurate in an absolute sense, such inaccuracy can be compensated for by providing at least a plurality of the relay antennae with an altimeter. In an embodiment, the relay antennae are powered by being plugged directly into a wall socket. Wall sockets are typically at a very standard height, such that the altimeters in the relay antennae form a horizontal reference plane. Data from the altimeter in the patient-worn sensor can thus be compared to the data from the reference plane altimeters to determine whether the height of the patient-worn sensor should be cause for alarm, such as the relatively low height of the sensor as the result of a fall, or the relatively higher height in the event the patient stands up.

Various user interfaces are disclosed which provide caregivers the information necessary to provide improved care.

These and other features, aspects and embodiments of the invention can be better appreciated from the following detailed description and appended figures, by which it will be apparent that the present invention meets a number of long-felt needs in the area of patient care.

DRAWINGS

Various aspects, features and alternatives of the invention can be better appreciated from the following detailed description when taken in conjunction with the appended Figures, in which:

FIG. 1A illustrates in block diagram form an embodiment of a system in accordance with one aspect of the invention in which one or more sensors provide to a host data representative of a patient's position, orientation, and movement, and the host uses that information, together with other patient information, to identify risks with respect to either avoidance or treatment of pressure ulcers on the patient, among other things.

FIG. 1C illustrates in block diagram form an embodiment of a system wherein the sensor forms a key part of a system for detecting and monitoring bed exits, falls, ambulation, location, orientation, and vital signs.

FIG. 2 illustrates in flow diagram form an embodiment of the process flow for comparing new sensor data from a patient with historical patient information for the purpose of preventing or treating pressure ulcers on the patient, and capable of running on the system of FIG. 1B.

FIG. 3A illustrates an accelerometer-based sensor in accordance with one aspect of the invention, for detecting turns and other medical conditions.

Figure 13:
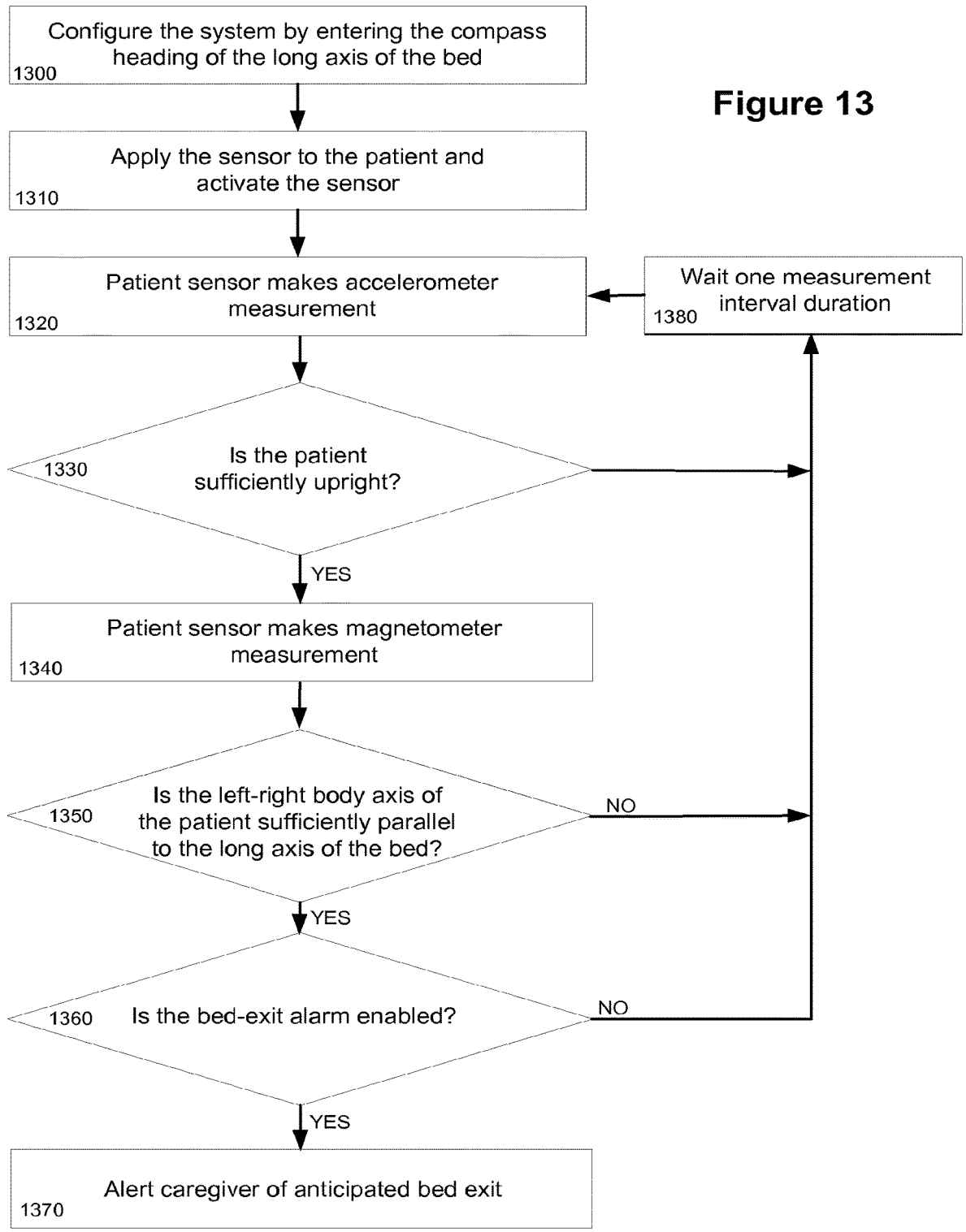

FIG. 13 further illustrates in flow diagram form an embodiment of the process flow for determining if a patient bed-exit is likely to occur.

Figure 14:
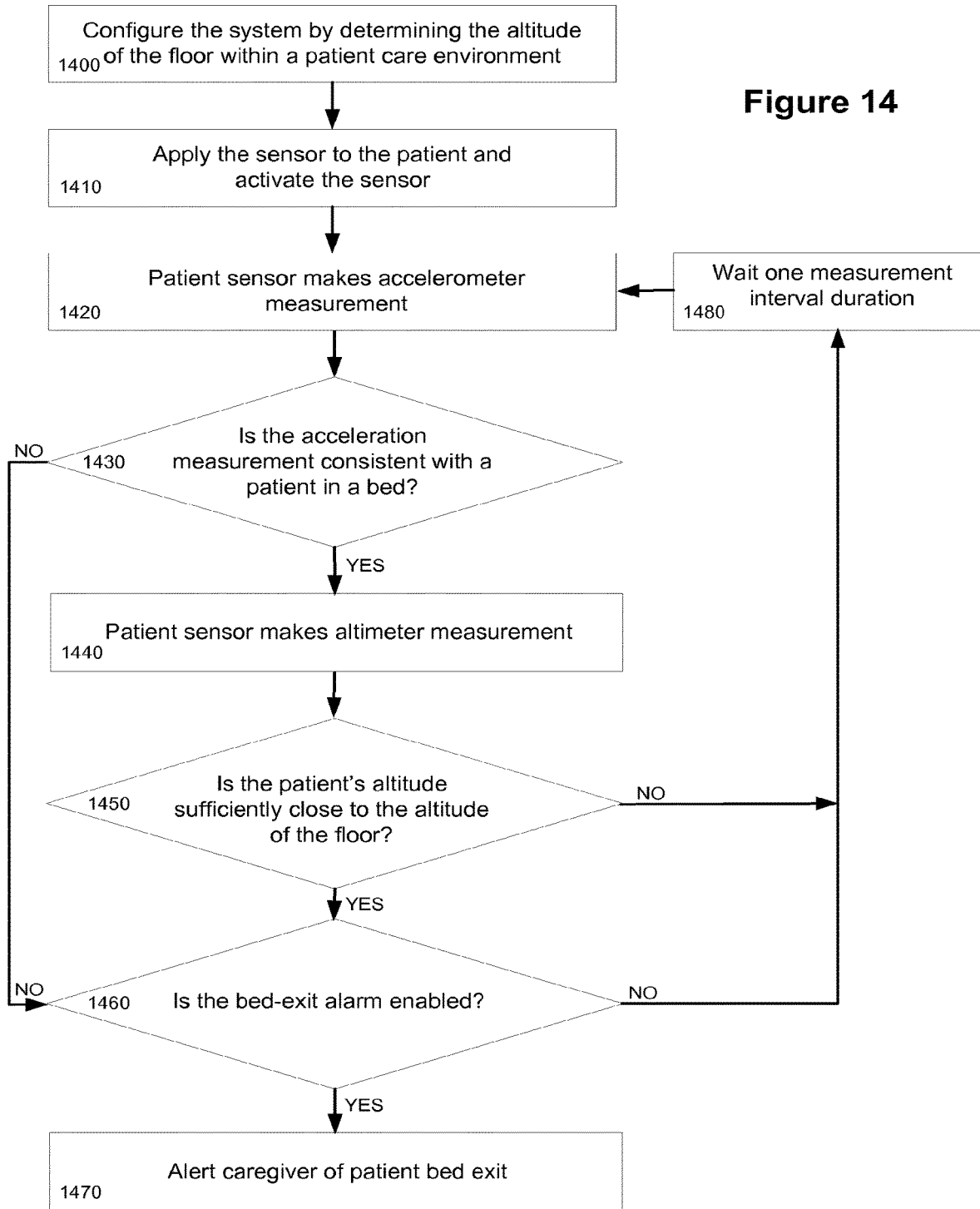

FIG. 14 illustrates in flow diagram form an embodiment of the process flow for determining if a patient bed-exit has occurred using accelerometer and altimeter information.

Figure 15:
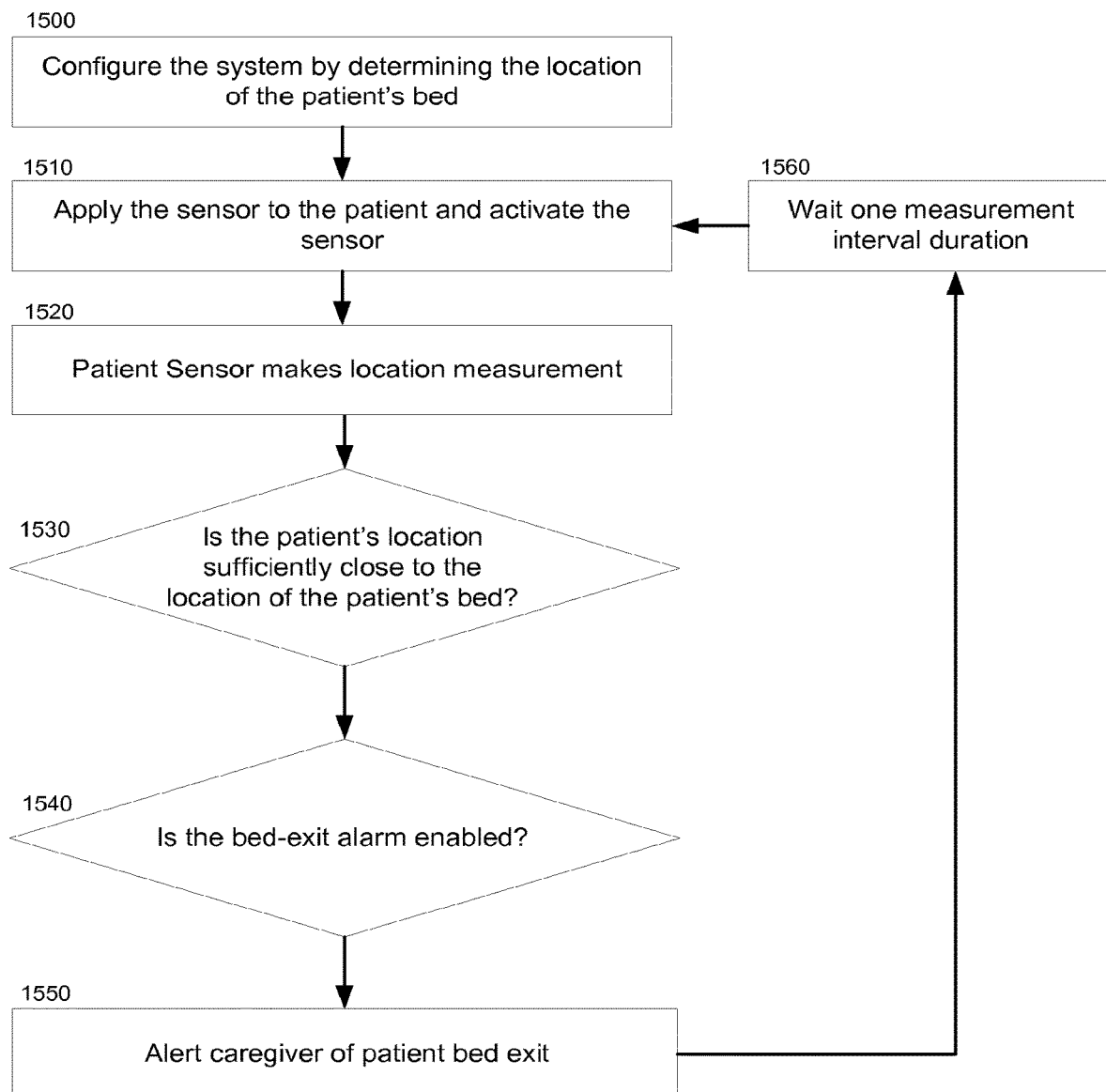

FIG. 15 illustrates in flow diagram form an embodiment of the process flow for determining if a patient bed-exit has occurred using location information.

Figure 16:
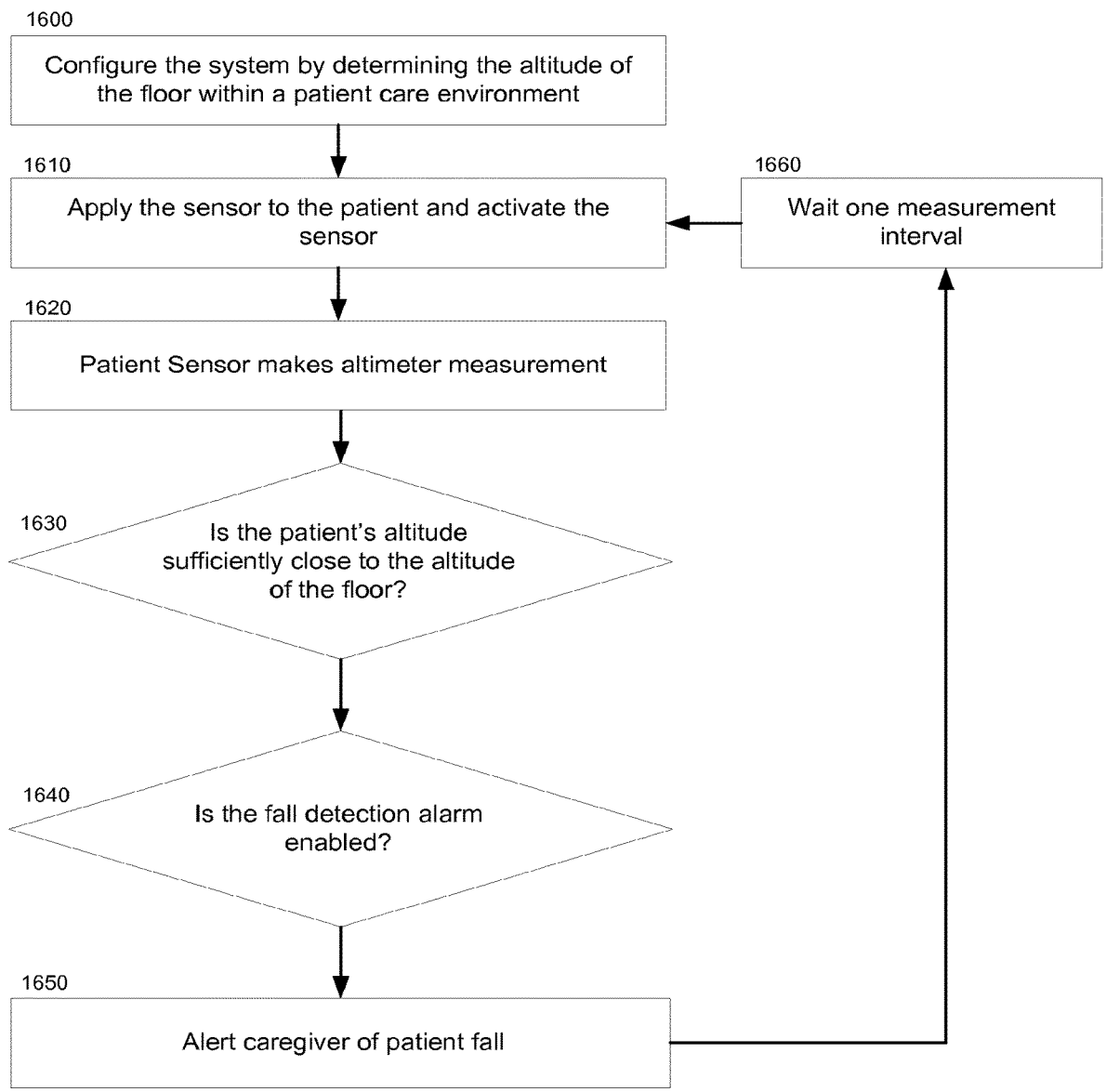

FIG. 16 illustrates in flow diagram form an embodiment of the process flow for determining if a patient fall has occurred using altimeter information.

Figure 17:
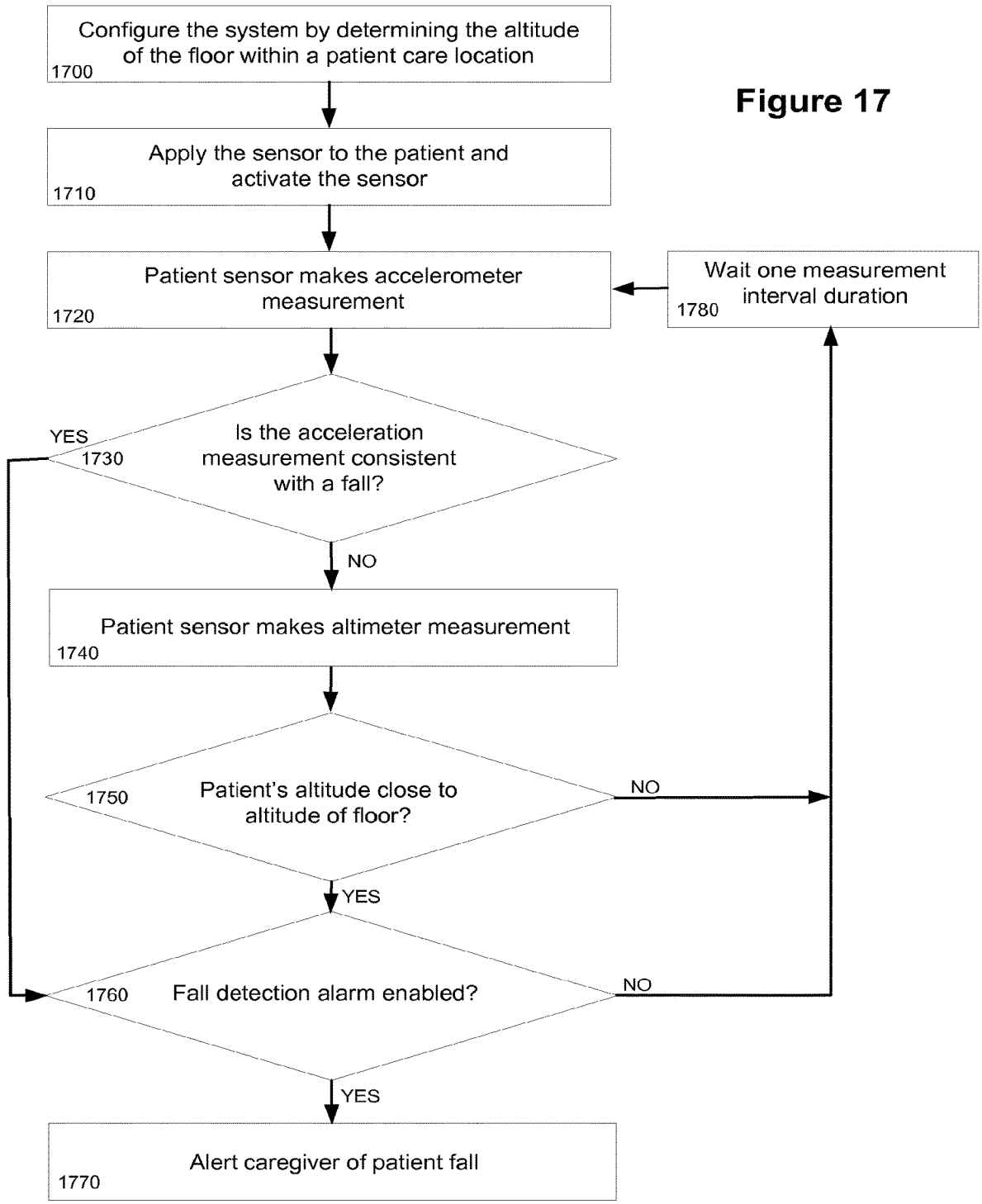

FIG. 17 illustrates in flow diagram form an embodiment of the process flow for determining if a patient fall has occurred using altimeter and accelerometer information.

FIG. 18 is a splash screen for the user interface of the system.

FIG. 19 is a user interface screen for assigning a sensor to a unit within a hospital.

Figure 20:
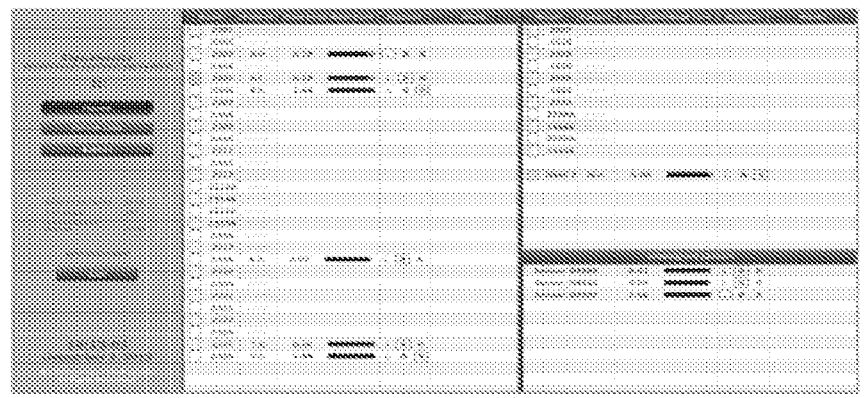

FIG. 20 is a table for recording sensor assignments to patients.

Figure 21:
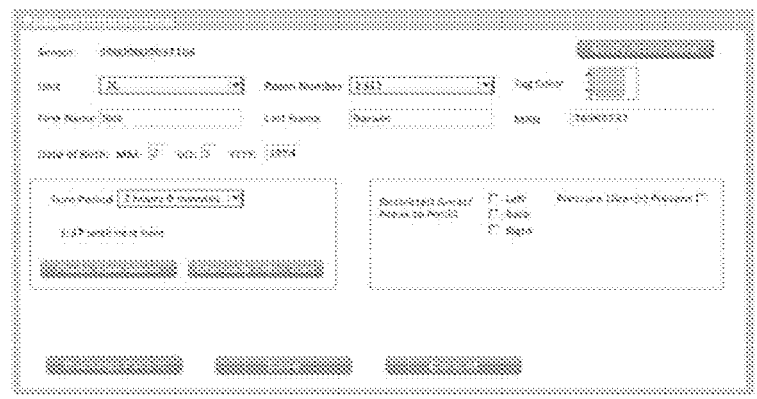

FIG. 21 illustrates a user interface screen for a particular patient being monitored by the system of the invention.

Figure 22:
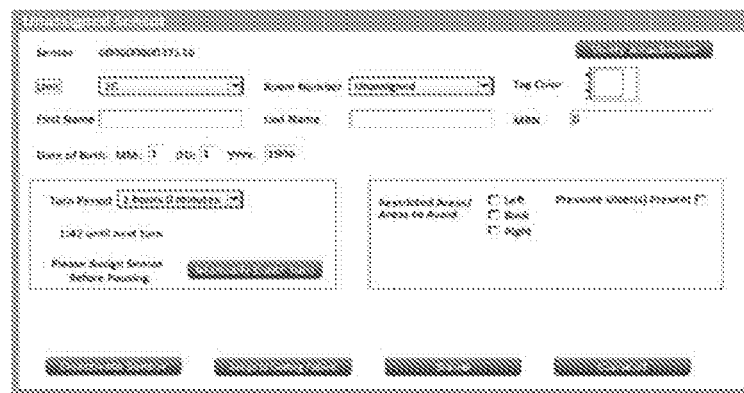

FIG. 22 is a user interface screen for an unassigned sensor.

Figure 23:
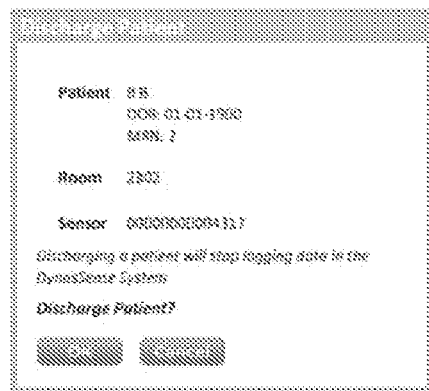

FIG. 23 is a user interface screen for stopping patient logging upon discharge.

Figure 24:

FIG. 24 is a user interface screen for pausing turn alerts.

Figure 25A:
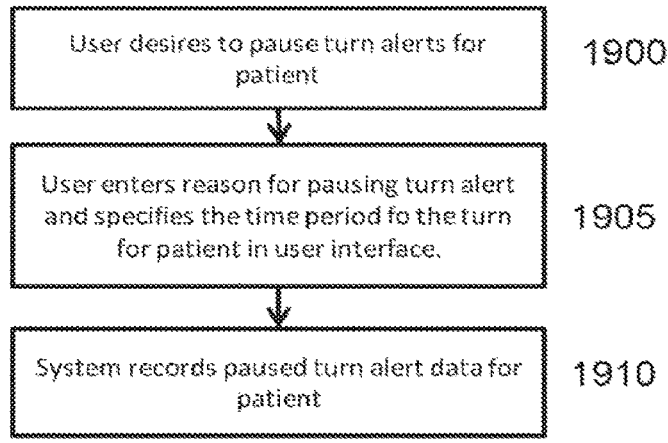
Figure 25B:
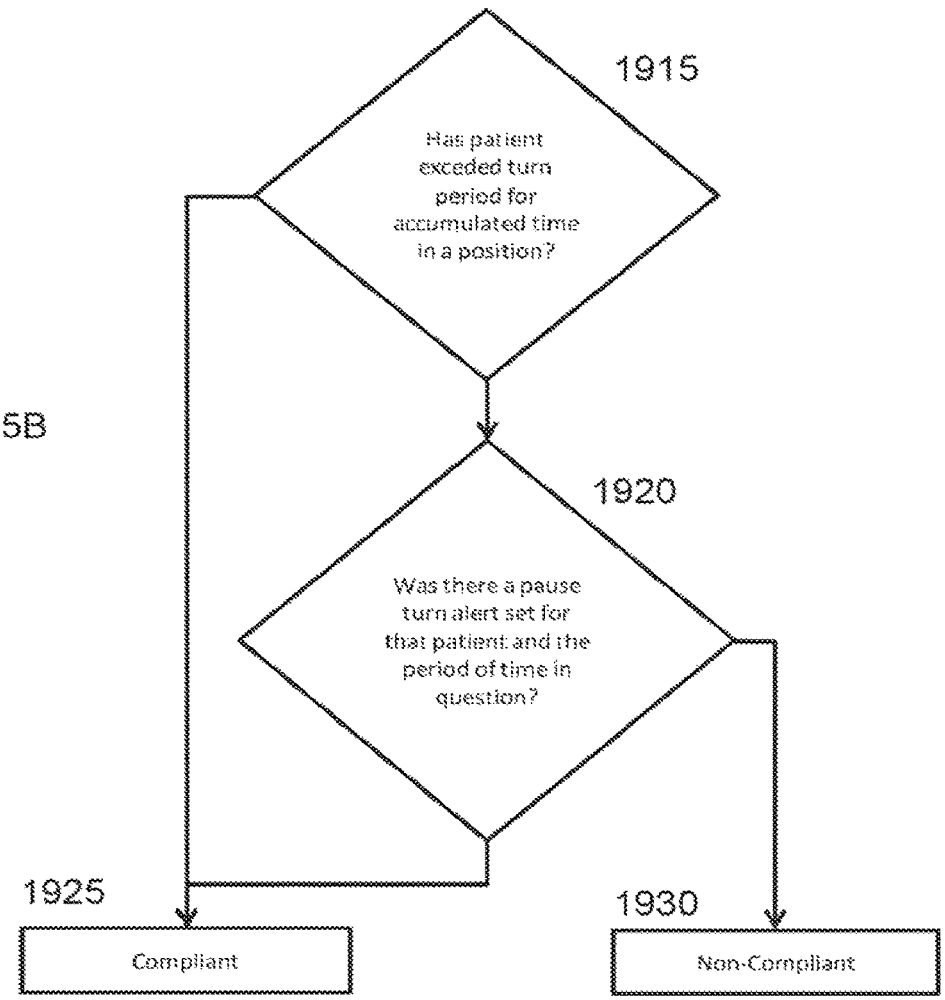

FIGS. 25A-25B illustrate one embodiment of a system flow for entering and recording pauses of turn alerts.

FIG. 26 is a user interface screen for logging, manual, a patient turn.

FIG. 27 is a user interface screen illustrating an embodiment for verifying sensor attachment.

FIGS. 28A-B are user interface screens showing various administrative settings.

DETAILED DESCRIPTION

Figure 1B:
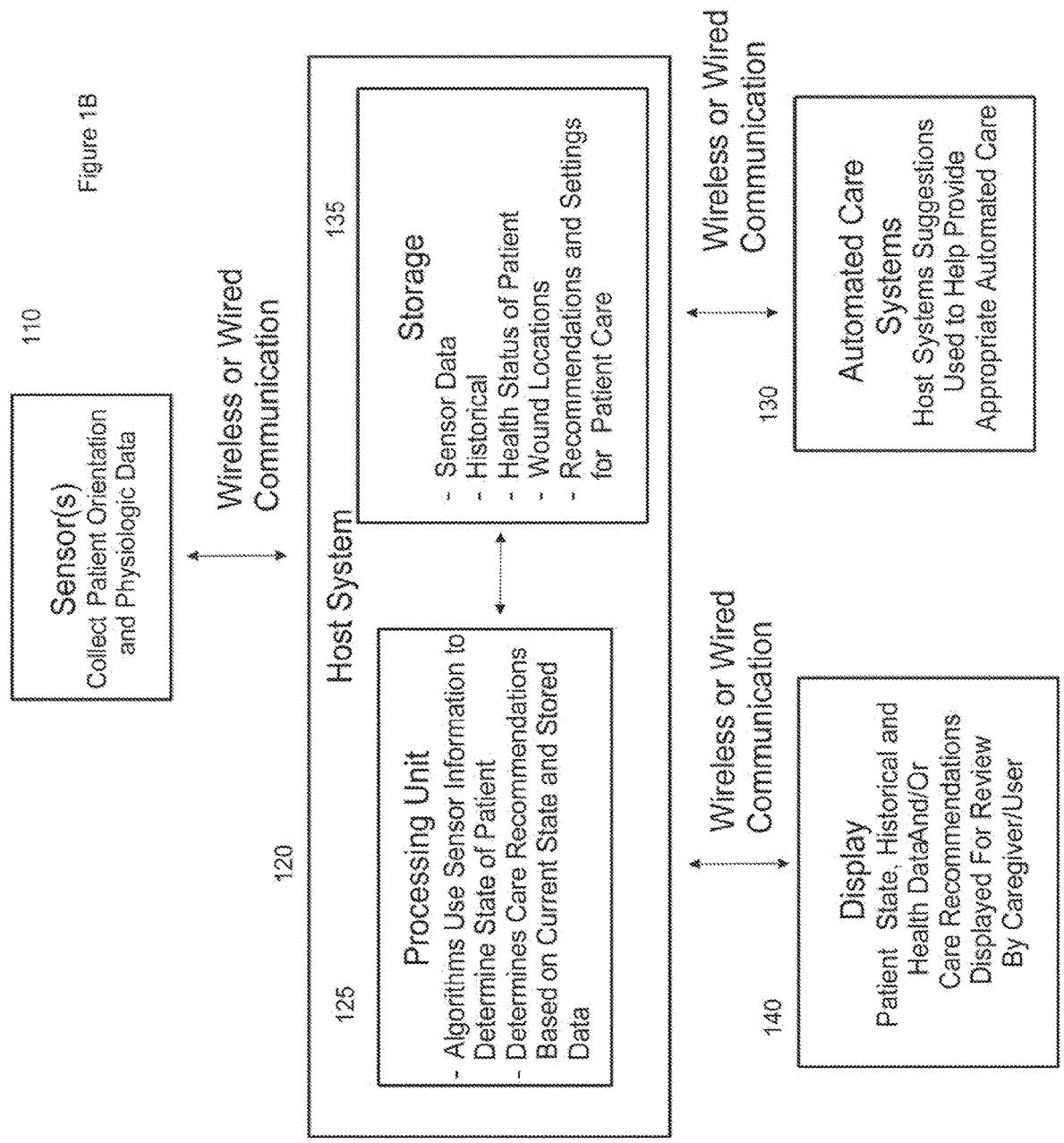
FIG. 1B illustrates in block diagram form an embodiment of the hardware of a system in accordance with one aspect of the invention.

In an aspect of the present invention, an improved means for managing and coordinating patient turning protocols is provided. Referring first to FIGS. 1A-1B, an embodiment of a system in accordance with an aspect of the invention is illustrated in flow diagram form. A patient 100 requiring monitoring, and in at least some instances having an existing wound or being at risk for developing a pressure ulcer, is associated with one or more sensors 110. As used herein, the term "patient" refers to any person or animal that may be monitored using any of the systems, methods, or devices disclosed herein, regardless of whether the person is admitted in a hospital, clinic, or other medical care facility, regardless of the location of the person (e.g., in a medical care facility, at home, or in any other location), and regardless of whether the person is receiving professional medical care or supervision. The sensors collect data about the orientation, position, and movement of the patient and/or wounds and/or areas of compromised tissue perfusion and/or areas of risk. The sensors communicate with a host system 120, typically a computer running at least one program for processing the incoming sensor information to determine the position or orientation or movements of a patient, wounds or areas of compromised tissue perfusion, or areas of risk on the patient. The program also uses historical and other data to analyze the sensor data and identify risks. In at least some embodiments, the data, including both the sensor data and the analytical data, is stored for future use.

Depending upon the embodiment, the output of the host system can provide direction to an automated care system, as shown at 130, or can display messages for the attention of a caregiver as shown at 140. In the latter instance, the caregiver uses the suggestions from the system together with training and judgment and makes a determination regarding management of a patient's care, as shown at 150.

Referring more specifically to FIG. 1B, an embodiment of the hardware components of the system of FIG. 1A can be better appreciated. More specifically, the sensors 110, a variety of which are described in greater detail hereinafter, collect patient orientation and physiologic data. In some instances, this can include heart rate, respiratory rate, and other data in addition to patient orientation, position, and movement. The host system 120 typically comprises a processing unit 125 together with at least one data storage device. The processing unit executes one or more software programs to analyze the sensor information and determine the state of the patient, to determine care recommendations based on the current state of the patient and relevant stored data, and, in some instances directs the operation of an automated care system 130. The data store 135 typically comprises a hard disk, RAM, EEPROM, solid state disk, or other memory device, and stores current and historical sensor data, health status of the patient, wound locations if any, at risk locations if any, as well as recommendations and settings for patient care. In some systems, the data store can be integrated with or linked to one or more of the hospital's databases, such that data in the data store 135 is updated whenever the hospital records are updated. The host system 120 communicates by either wired or wireless links with the display 140 and/or one or more automated care systems 130.

Figure 1D:
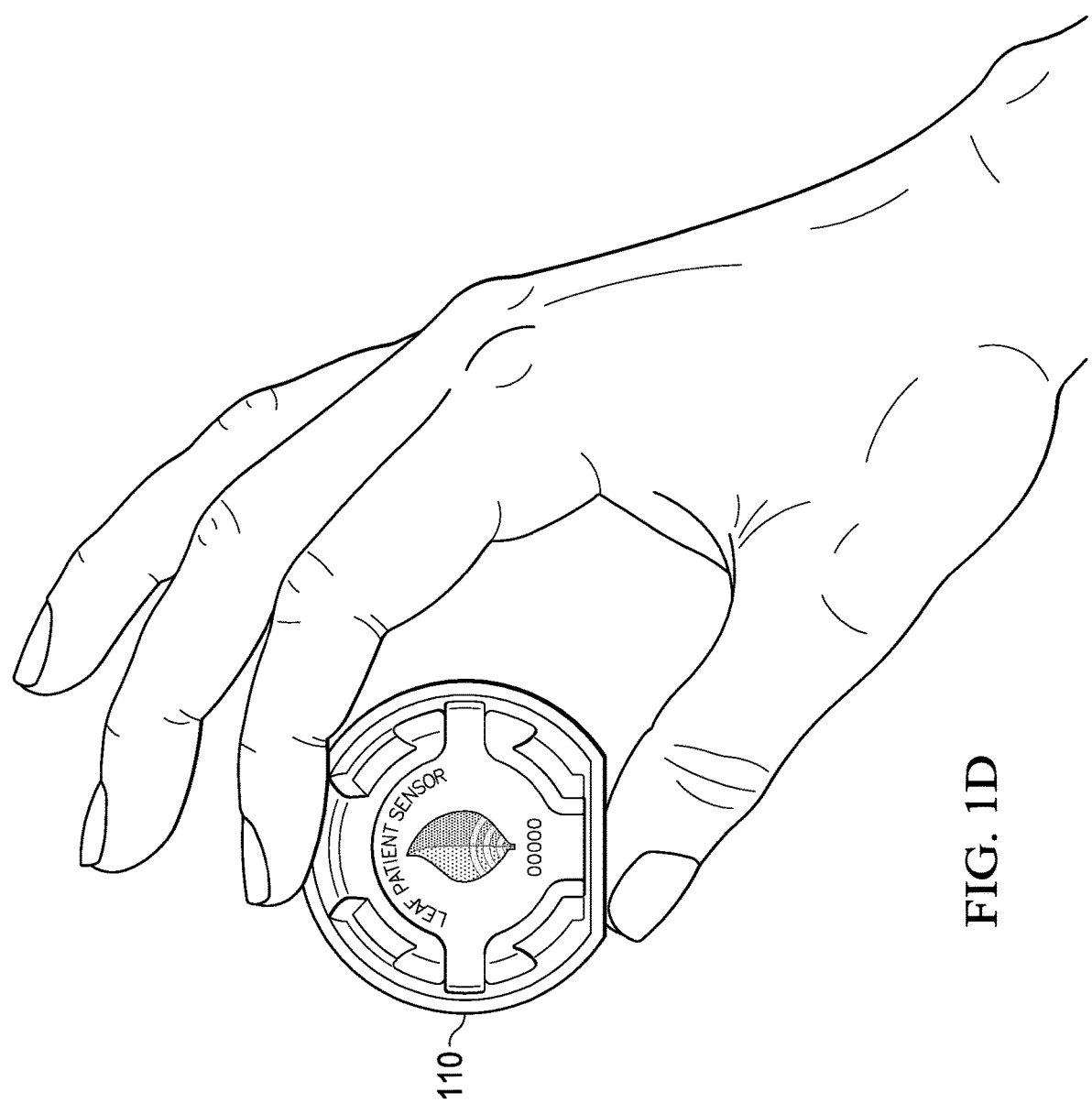
FIG. 1D illustrates the relative size of a wireless sensor in accordance with an embodiment of the invention.

With reference to FIGS. 1C and 1D, in an embodiment, a sensor 110 comprises a multi-axis accelerometer, for example a three-axis accelerometer, a magnetometer and an altimeter. Such a combination, typically in combination with a host network comprising a mesh network of relay antennae and at least one server/host, enables the detection and monitoring of patient orientation 155 while in bed, to permit the use of a personalized turn protocol. The combination can further detect patient orientation 155, vital signs 160, bed exits 165, falls 170, patient location 175 and patient ambulation 180.

As used herein, the term "bed" means any physical support apparatus designed or configured to physically support a person at least partially off (above) the floor or ground, e.g., a bed, chair, medical table, gurney, or other support apparatus designed or configured to physically support a person at least partially off the floor or ground. Thus, any reference herein to a "bed exit" refers to a person exiting (e.g., leaving) a bed, chair, medical table, gurney, or other support apparatus physically supporting the person at least partially off the floor or ground.

As shown in FIG. 1D, a sensor 110 in accordance with an embodiment of the invention comprises a small, lightweight, single use, disposable device having enclosed within a housing that is affixed to a patient. The sensor is typically affixed by means of a medical adhesive to the upper torso of the patient, such as at the sternum or below a clavicle. The sensor can, in some embodiments include indicia for orienting the sensor relative to body, e.g., with the top of the indicia pointing toward the head of the patient.

Referring next to FIG. 2, the operation of the software component of the system of FIGS. 1A-1B can be better appreciated. Data 200 from the sensor is initially filtered and analyzed, as shown at step 205, to determine if the sensor is both used and functioning properly. That determination is made at step 210; if the sensor is not functioning properly, a notice about the deficiency is sent at step 215. However, if the sensor is functioning properly, the process continues at step 220, where the raw sensor data is filtered and analyzed to determine the orientation of the patient. Then, at step 225, an orientation-based pressure map is generated, followed at step 230 by a pressure-time determination to assess how long areas of tissue have been subjected to a given pressure. A time input can be derived from the host 120, or a separate time base can be used to make the pressure-time measurement. Then, at step 235, the pressure-time measurement is compared to a preset limit, and, together with historical data, how long the area has been depressurized, when the most recent depressurization of the area occurred, health conditions of patient, location of wounds, areas of risk, and other factors, together with historical positioning data as shown at step 240, a determination is made regarding suggested repositioning.

Then, at step 245, a determination is made as to whether the data suggests that the patient should be repositioned soon. If no, the process ends at step 250, with, in some embodiments, the display of orientation, position, and movement data and a suggested repositioning schedule. If yes, and an automated care function exists, the decision at step 245 results in a directive to provide automated care at step 255. Alternatively, or in the event that automated care is not successful, a message is sent to a caregiver at step 260 advising of the need for repositioning, as well as a suggested new position. The caregiver either accepts the suggestion, indicated at 265, or provides alternate care at step 270 based on judgment and training.

In at least some embodiments, the sensor itself is important to the operation of the system of the present invention. Acceptable sensors for the system of the present invention can vary widely, and include sensors both in continuity with the patient's body and affixed thereto, or remote to the patient's body. Possible sensors include accelerometers, RFID sensing, resistive, capacitive, inductive and magnetic sensors, reflective sensors, infrared sensors, video monitoring, pressure and stress sensors, transcutaneous oxygen pressure sensors, transcutaneous $CO_2$ sensors, hydration sensors, pH sensors, ultrasound sensors, remote optical spectroscopy sensors, and laser Doppler flow sensors, among others.

For some embodiments, the sensor can be as shown in FIG. 3. The sensor of FIG. 3 comprises a multi-axial accelerometer 305 with associated processor 310 and related electronics, generally indicated by 300. One acceptable accelerometer is the type LIS344ALH three axis accelerometer available from ST Microelectronics, although sensing on three axes is not required in all embodiments. In addition to the accelerometer, the sensor 300 can also comprise a capacitive sensor 315, a temperature sensor 320, a moisture sensor 325, and an electrical signal sensor 330. The microprocessor 310 can comprise a built-in A/D converter and stored sensor identifier, and communicates with a base station/host 335 which can include a transceiver for wireless communications, located near enough to reliably receive wired or wireless signals, through an RF transceiver 340 and antenna 345, which may be integrated into a network such as those shown in FIG. 4, discussed in greater detail hereinafter. In some embodiments, the transceiver/base station 335 communicates with a remote host. In either case, the host may ultimately link to viewing terminals 350 that can be, for example, integrated into the patient sensor or support system, in the patient room, at the nursing station, or at other locations. It will be appreciated that, while not shown, a battery or other power source is provided in the sensor 300. It will be appreciated by those skilled in the art that the functions of the host can reside in several different locations in a system in accordance with the present invention. For example, the host functionality can largely reside in the sensor itself, or that functionality can coexist within the base station, or it can be external to both, or the functions can be split across multiple devices.

In an embodiment of the sensor, the device is stored such that battery life is preserved until the unit is put into use. Alternatively, the sensor is designed with a rechargeable battery or other energy storage device such as a capacitor. A rechargeable sensor can be recharged by connecting with a cable to some other energy source such as a power converter or can be recharged wirelessly through the use of an inductive charger. A non-rechargeable system may have lower cost and be more suitable for one-time disposable use in a hospital or other short-term care environments while a rechargeable sensor may have greater initial cost but may be more economical in a long term-care facility, such as a nursing home. As discussed in greater detail in connection with FIGS. 5-7, and more specifically FIG. 6, the sensor can be activated by, for example, removing the adhesive backing on the unit. Alternatively, the sensor can be activated by a conventional switch, or by exposure to ambient light in the patient's room, or activated upon exposure to a patient. In some embodiments, the sensor can be activated by passive RFID, which can be built into the unit itself or embedded in the adhesive backing of the unit. The sensor can also be activated by RF or inductive loops, or any other suitable application of power. Precautions are also typically taken to protect the sensor's accelerometers. Precautions can be taken, for instance, to prevent damaging accelerative forces from acting on the accelerometer. In an embodiment, the casing of the sensor unit can be compressible so as to decrease the accelerative force of a fall or impact. Alternatively, or additionally, the accelerometer can show when an acceleration large enough to cause damage or a need for recalibration is experienced and the senor unit can then signal that it is damaged or in need of calibration. In other embodiments, the sensor can also include an additional accelerometer capable of sensing accelerations greater than the acceptable range for a primary accelerometer, to be used to measure accelerations that can damage or cause a requirement for recalibration in a more sensitive accelerometer. In an accelerometer with more than 2 axes, all 3 axes can be used to determine orientation, providing more than one calculation of orientation that can be compared and used as an indicator that an accelerometer is damage or in need of recalibration.

The sensor, together with other system components as shown in, for example, FIG. 1, can provide real-time monitoring of a patient's orientation and surface pressure distribution over time, whereby patients requiring intervention can easily be identified. As discussed briefly above, an embodiment utilizes small, thin, inexpensive, wireless and disposable sensors that safely monitor the 3-dimensional orientation of a patient over time. In an embodiment, the sensors have an adhesive backing, such that they can be affixed to the patient's body. In an embodiment, one or more sensors can be placed on the body at known anatomic locations, although the anatomical location of the sensor(s) is not required to be known in all embodiments. The sensors can be placed on the body in a location that does not increase the risk for tissue damage. In one instantiation of this embodiment, a small sensor is affixed to the sternum or the anterior superior iliac spine (ASIS) of the patient. The sensors can also be embedded in articles worn by the patient, such as shirts or underwear, bracelets, belts, or collars, as long as the sensor does not move significantly relative to the patient.

In at least some embodiments, the sensors used in the present embodiment contain one or more accelerometers, gyroscopes, magnetometers, or other devices such as described in connection with FIG. 3B hereinafter, which are capable of measuring one or more conditions or characteristics of the patient. The accelerometer can reliably and accurately measure patient tilt, patient orientation, patient movement, and vibration, and shock, as would occur with a fall. The accelerometer can be coupled to a wireless transmitting device, such that there are no wires extending from the patients to whom the sensors are attached. Wireless communication can be achieved via radio frequency transmission. Monitoring the wireless communication from the body sensors enables real-time tracking of the condition of the patient, including patient orientation and orientation-based pressure distribution over time. Alternatively, wireless communication can be implemented using an infrared or other optical link.

The present embodiment can be used to accurately monitor the static angle and acceleration of patients relative to the support surface. By continuously measuring the patient's orientation relative to the physical support apparatus the invention can determine to what extent the patient needs to be repositioned and/or the extent to which a next-scheduled turn can be skipped or delayed. Warnings can be given in response to a predefined condition, such as prolonged patient position at a specific angle relative to the physical support apparatus. The sensor data can be transferred to a central location that manages a network of monitored patients to ensure that all patients are being repositioned adequately. The network can be used to provide warnings to caregivers and to coordinate patient repositioning schedules amongst caregivers.

As discussed in greater detail hereinafter, embodiments of the sensors and monitoring system described herein are able to track the cumulative amount of time that a patient has been in a specific orientation relative to a physical support apparatus. The system can also estimate the surface pressure exerted on different regions of the body based on the direction of the gravitational force vector (as determined by the accelerometer), the orientation of the physical support apparatus, and the estimated magnitude of that force vector (as defined by physical attributes of the patient, such as height, weight, BMI, mass distribution, etc.). A computer can analyze the patient orientation/surface pressure data over time for each patient, and recommend optimal repositioning maneuvers based on this data. Furthermore, the cumulative surface pressure distribution for each patient can be seamlessly tracked and recorded as the patient moves to and from different physical support apparatuses (e.g., bed, chair, wheelchair, couch, etc.). Information regarding each patient's pressure ulcer history, Braden score, and other conditions of the patient can be entered into the monitoring system. In some embodiments, the system can recommend an optimal repositioning schedule based on patient-specific data.

In one embodiment, the sensing system is properly secured to the patient in order to accurately determine the patient's orientation and surface pressure distribution. In an embodiment, the system of the present invention comprises means for automatically determining if the sensor system is properly attached to the patient. A system that can detect and notify the caregiver when the sensor is not attached, not attached properly, not oriented on the patient properly, not located on the patient properly, or is otherwise not working properly is desirable. Such a condition, if not detected, can result in the patient being in an orientation sufficiently long to develop a pressure ulcer or experience some other adverse medical condition. Depending upon the embodiment, the present invention can use any of several methods to verify proper location, orientation, and operation of the sensor. One set of embodiments comprises means and method for detecting biometric parameters that indicate if the orientation sensor is properly secured to the patient. In this approach, the orientation sensor is considered properly attached to the patient only when detected biometric parameters fall within predefined values based on known physiological behavior. If the detected biometric parameters fall outside of predefined limits, then the patient orientation sensor is considered to be improperly secured to the patient, or not attached to the patient, and caregivers can be alerted. The detected biometric parameters can include, but are not limited to, skin capacitance, respiratory rate, heart rate, and temperature. In the event of any error condition, where the measured parameters are out of range, the system notifies the caregiver that the system or more specifically, the sensor or base station is not working properly.

Figure 3B:
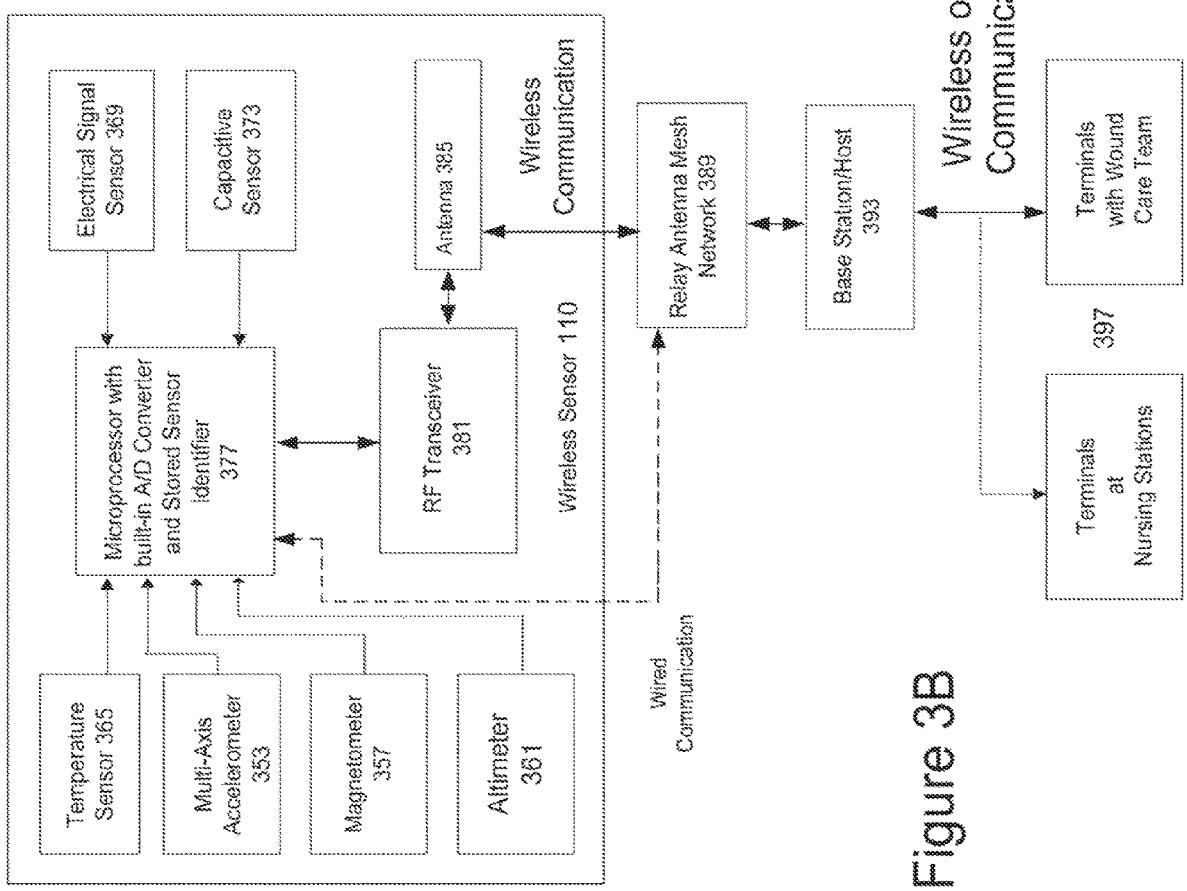
FIG. 3B illustrates in block diagram form the functional hardware architecture of an embodiment of a sensor in accordance with the invention, and its communication to a caregiver through a mesh network and a host.

With reference next to FIG. 3B, the hardware architecture of a sensor in accordance with another embodiment of the invention can be better appreciated. In such an embodiment, the sensor 325 comprises a multi-axis accelerometer 353, a magnetometer 357, an altimeter 361, a temperature sensor 365, an electrical signal sensor 369, and a capacitive sensor 373, all of which provide data to a microprocessor 377. The processor 377 includes an indicia which uniquely identifies the particular sensor. The processor at least collects, and in some instances processes at least some, data from the sensors and sends that unprocessed and/or processed data to an RF transceiver 381 which then transmits the data via antenna 385. Not shown in FIG. 2 is a battery for providing power for the various sensors and circuits. It will be appreciated by those skilled in the art that, for some patients, it may be desirable to affix multiple sensors at different locations.

The sensor data transmitted via the antenna 385 is received on one or more relay antennae forming a mesh network 389 as described greater detail in connection with FIGS. 4A-4D. In an embodiment, the data is received on a plurality of the antennae, permitting the location of the patient-worn sensor to be determined with reasonable accuracy. The various antennae communicate their information to a base station host/server 393, which then processes the data in the manner discussed hereinafter. Depending upon the particular data, the host may then generate status updates, warnings, alarms and/or care recommendations to one or more caregivers as illustrated at 397.

Figure 4A:
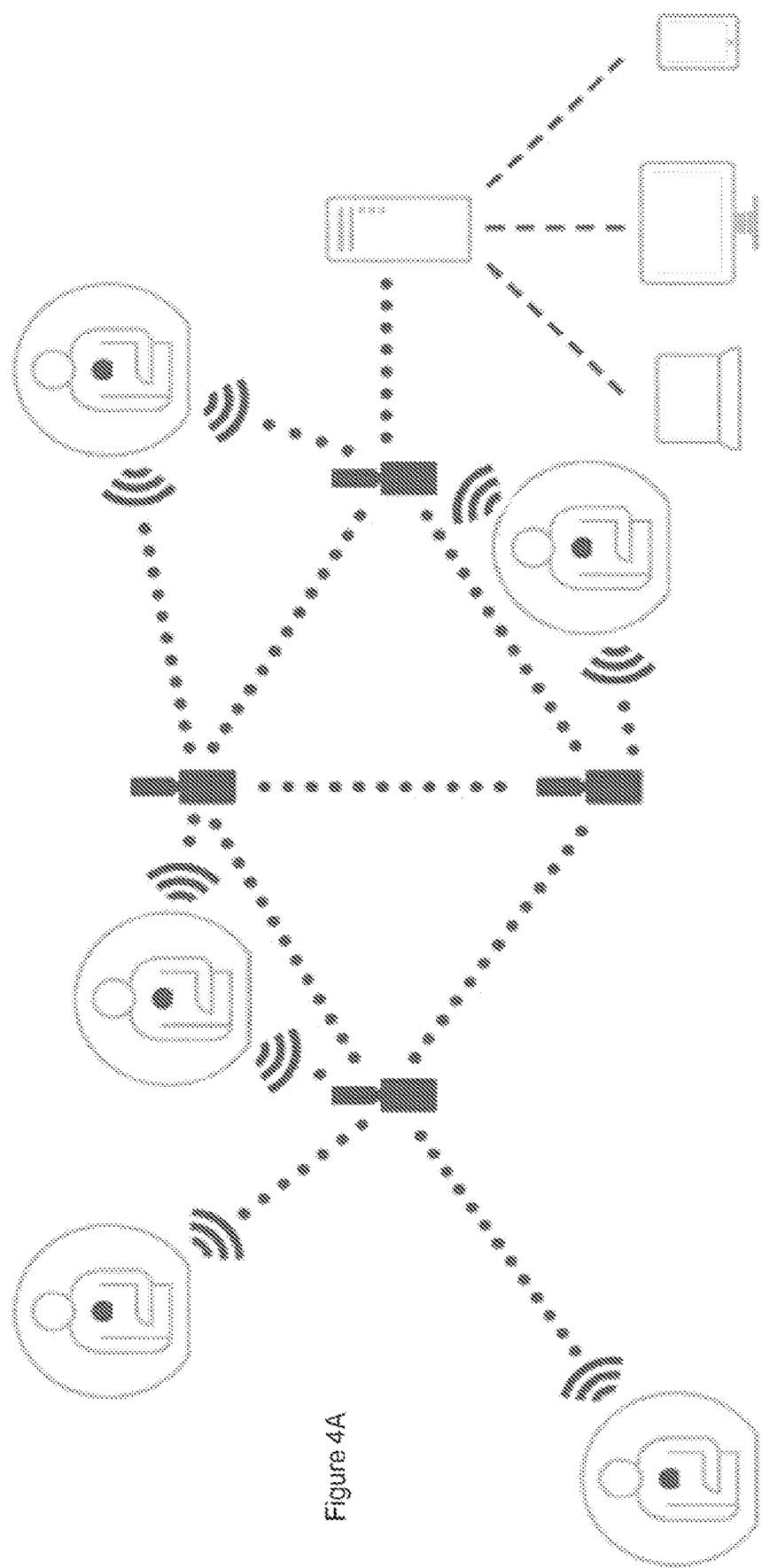
FIG. 4A shows various network configurations for monitoring patient orientation in accordance with some embodiments of the invention.
Figure 4B:
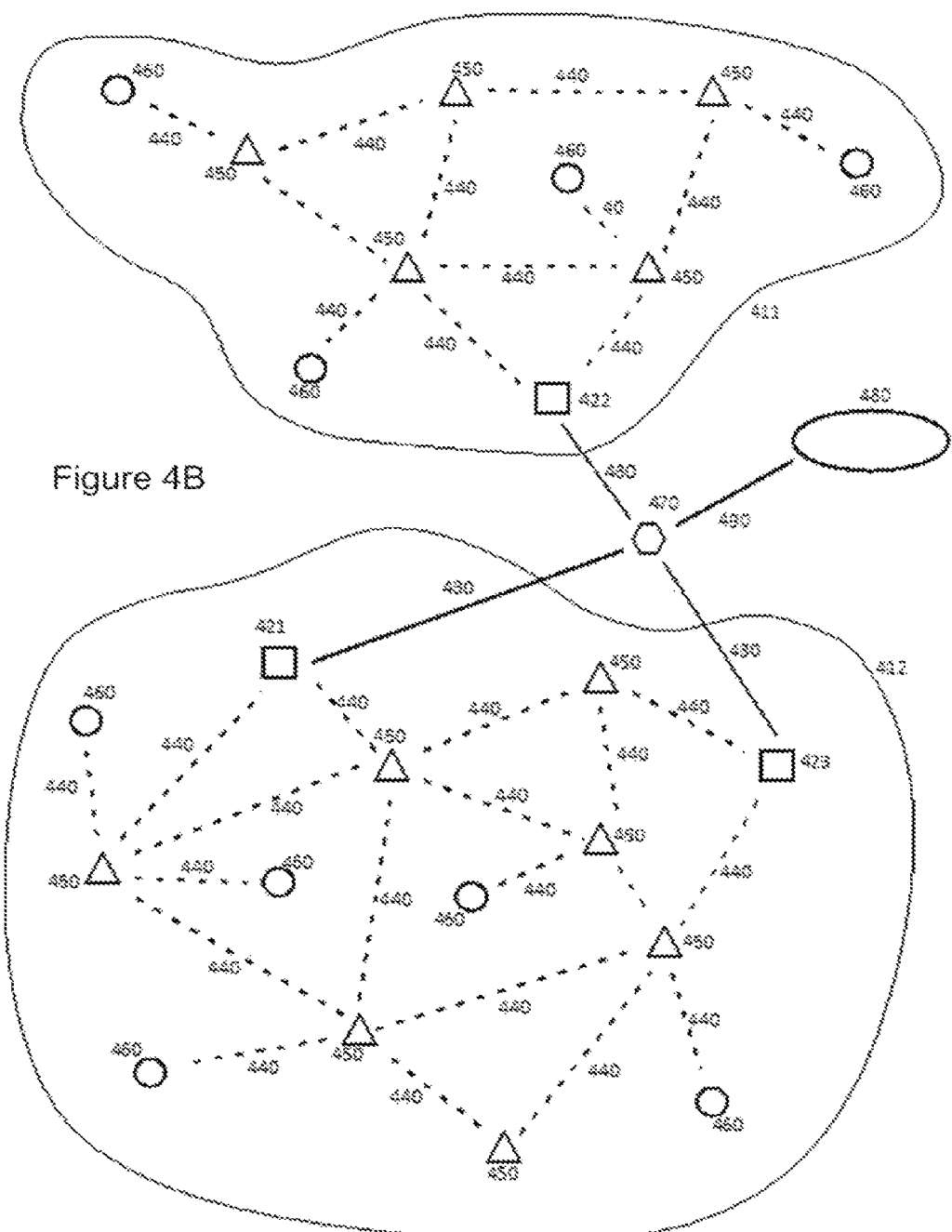
FIG. 4B illustrates in block diagram form the data acquired and processed in the various functional blocks in accordance with an embodiment of the invention.

With reference to FIGS. 4A-4B, a mesh network in accordance with an embodiment of the present invention can be better appreciated. In particular, FIG. 4A illustrates generally a plurality of patients each wearing a sensor in accordance with the invention, while FIG. 4B illustrates the network in greater detail. The sensors communicate with one or more proximate relay antennae, and the various relay antennae forward that data to the host. As shown in FIG. 4B, network 411 is comprised of an array of relay antennas 450 that can communicate via wireless links 440 with each other to form a mesh network. Patient Sensors 460 communicate via wireless links 440 with relay antennas 450 in order to send messages and receive messages from back end server 422. The backend server 422 of network 411 stores and retrieves data from a database 470 over a link 430.

Communication links 440 can be any suitable means for communicating between two relay antennas 450, between a relay antenna 450 and one or more patient sensors 460, or between a relay antenna 450 and back end server 422. Communication links 440 can be wired or wireless. The link 430 can also be any suitable communication link between the back end server 422 and database 470. The links 430 can be different in nature than the links 40 within the mesh network 11. For example, links 440 can be wireless links and link 430 may be a hard-wired link. Alternatively, the database 470 may reside within server 422, or distributed across a plurality of servers or other host computers.

Network 412 shows a more complicated mesh architecture with multiple back end servers 421 and 423. Although only two are shown, any number of backend servers can be interconnected within a single mesh network. Both of the back end servers 421 and 423 of network 412 communicate with the same database 470, although, as noted above, the database 470 can also be distributed across a plurality of machines.

In some embodiments, networks 411 and 412 are substantially isolated from one another as depicted in FIG. 4. The isolation may be because the networks are geographically separated and the antennas in the different networks do not have sufficient power to communicate with each other. Alternatively, the networks may be co-located but isolated through software or hardware protocols that prevent the antennas of the different networks from communicating with each other. Although networks 411 and 412 are isolated, the back end servers of each network may use the same database 470. In this way, the networks may be logically treated as the same network by hardware or software systems that process data from the database.

Other devices 480 can access the database to read, write, or modify data within the database. Other devices 480 that can communicate with the database 470 can be, for example, front end components of the system that interface with hospital staff, other facility computing or data systems such as electronic medical record systems or other patient monitoring systems, or nurse call systems. The communications link 490 that other systems use to access the database may be similar to or different from data links 430 and 440. For example, communication link 490, can use an HL7 interface or other protocol commonly used for interfacing hospital data systems.

In one implementation of the present invention, caregivers are able to view patient data on a display device. The patient data enables caregivers to provide more efficient and effective care, particularly as it relates to pressure ulcer prevention. From the display device, caregivers are able to view the turning status and other care parameters for one or more patients.

Figure 4C:
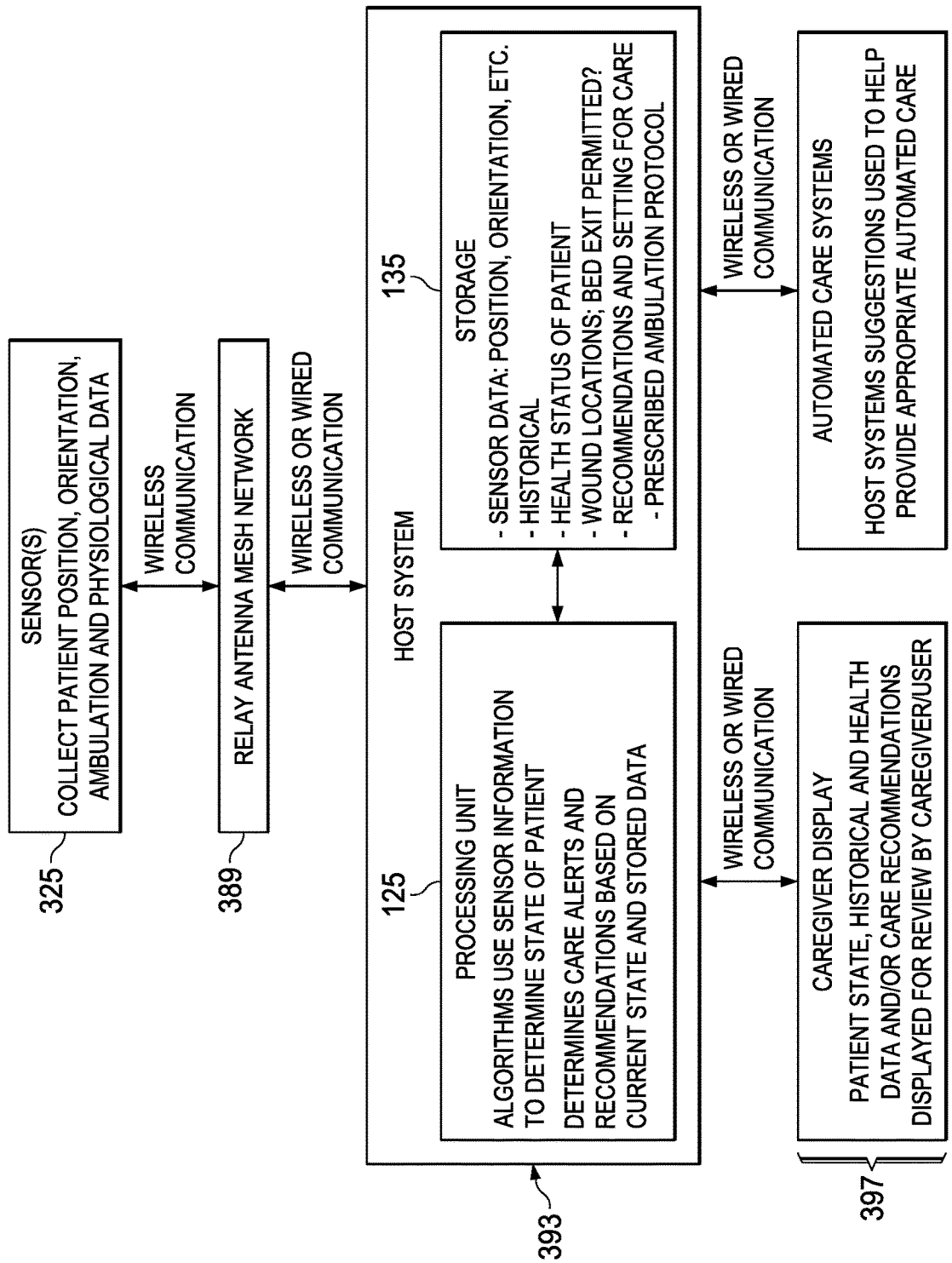
FIGS. 4C and 4D show an embodiment of the interaction of the patient-worn sensor with a host through a mesh network formed by a plurality of relay antennae, with the resulting data being ultimately provided to a caregiver through a display such as a computer, a tablet, or a smartphone.
Figure 4D:
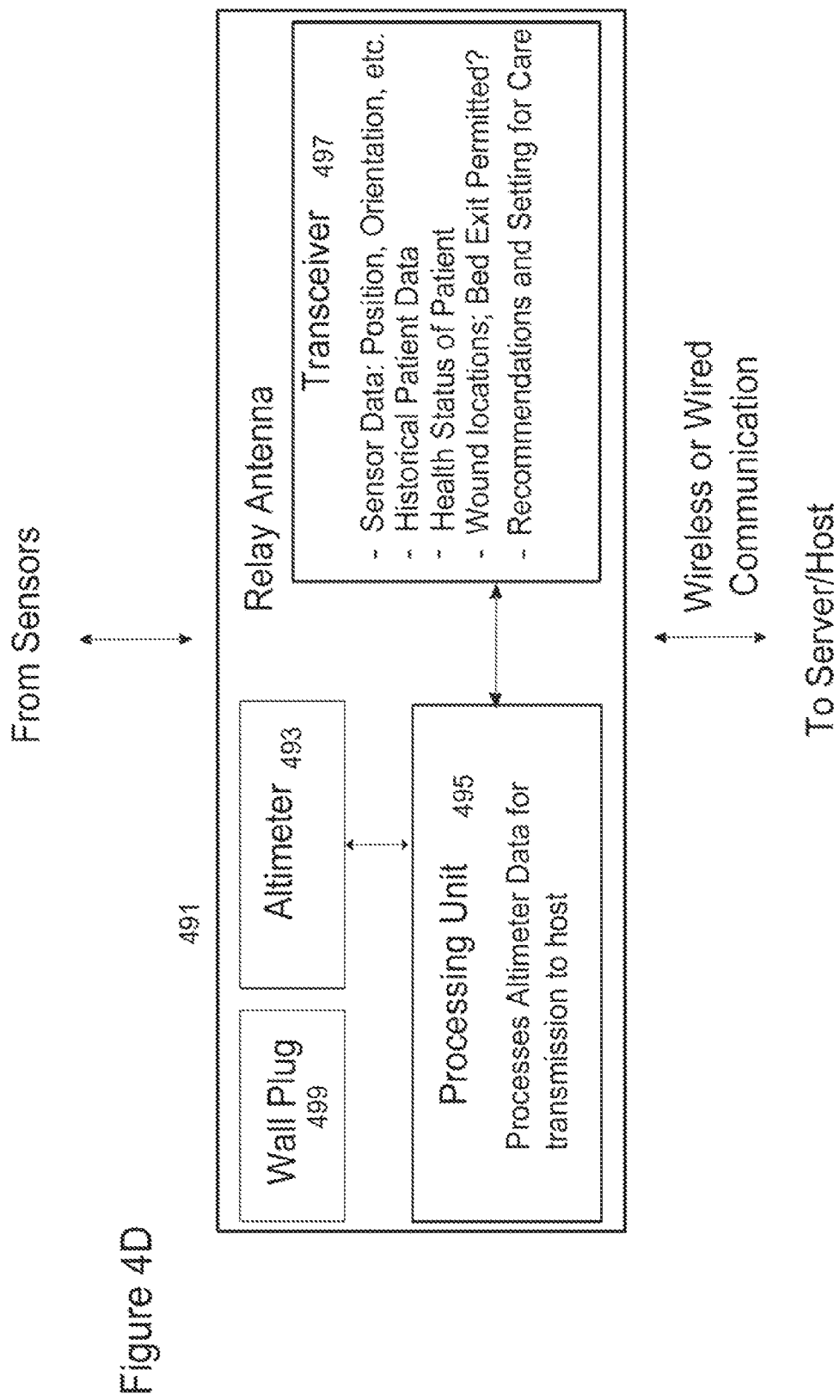

Referring next to FIG. 4C, the interaction of the sensor, mesh network and host can be better appreciated, while FIG. 4D illustrates the structure of the relay antenna module. In particular, one or more sensors 325 collect patient position (including height as appropriate), orientation, ambulation and physiological data and communicates that data to a mesh network 389. The mesh network then communicates that data, either wirelessly or via wire, to the host system 393. The host system 393 typically comprises at least a processor 125 and storage 135. The host processor manipulates the received data in accordance with various algorithms as well as the stored sensor, historical and other data to determine the state of the patient. Using that information, the host processor can generate care alerts and make recommendations for patient care specific to the particular patient. The alerts and recommendations are then provided to the caregivers or automated systems, generally indicated at 397 and as described above. In at least some embodiments, the data, including both the sensor data and the analytical data, is stored for future use.

It will be appreciated that a typical use of an embodiment of the invention as shown in FIGS. 4A-4C involves the caregiver using the patient management software of the present invention to define individualized turn, bed exit, ambulation and other protocols for one or more patients that require monitoring. The individual protocol parameters are stored in the Database for future reference. The Patient Sensor, which is disposable and wireless in some embodiments, is associated (for example, adhesively affixed) to the body of the patient being monitored. The sensor makes measurements of the patient's orientation and communicates this data, wirelessly or by other suitable means, over the data collection network previously set up in the facility. The network relays data from the Patient Sensors to a server computer connected to the data collection network. Software running on the server computer collects the patient data and stores the data into a database for subsequent analysis. The patient's orientation and other patient related metrics can then be determined by analyzing the data stored in the database. The Patient Management Software displays each patient's turn history and current status. The Patient Management Software also alerts staff if any patient requires a caregiver-assisted turn. The system also has the ability to automatically document each patient's turn history (including caregiver-assisted turns and patient self-turns).

In addition to the features discussed above, an embodiment of the system of FIG. 4C can include monitoring for bed exits and falls among its functions. In such an embodiment, the sensor includes an altimeter and a magnetometer in addition to the accelerometer, and optionally other detectors. Depending upon the patient characteristic being monitored, the sensor provides data from one or more of the detectors, such as the accelerometer, magnetometer and altimeter, and provides it to the host system. The host system processes that data, for example using one or more of the algorithms described hereinafter in connection with FIGS. 12-17, by which the system uses current and historical data to determine the probability that a bed exit is likely to occur soon, or that a fall has or is about to occur. The historical data for such a determination comprises, in at least some embodiments, prior sensor data, the health status of the patient, the location of the bed and a compass heading for a reference axis of the bed, the altitude of the floor, and, optionally, recommendations and settings specific to the care of the monitored patient.

Referring next to FIG. 4D, the architecture of an embodiment of the relay antenna 491 can be better appreciated. In particular, the relay antenna 491 includes, in at least some instances, an altimeter 493 which provides elevation data to a processing unit 495. In addition, the relay antenna comprises a transceiver 497, which both receives data from the sensors proximate to it, and transmits to the host/server that data as well as the altimeter data received from the processor 510.

In addition, in at least some embodiments the relay antenna includes a wall plug 499 for providing power to the unit while also permitting extremely easy installation within a monitored facility. Further, because wall plugs in facilities such as hospitals are typically at a uniform height, the altimeters in the various relay antennae form a horizontal reference plane against which relatively small variations in the height of patient-worn sensors can be reliably detected. This assists in the detection and monitoring of bed exits, falls, and ambulation.

It will be appreciated that, while some embodiments described above include all of an accelerometer, a magnetometer and an altimeter, not all embodiments necessarily require having the entirety of these sensors.

As described previously, traditional pressure ulcer prevention protocols involve turning high-risk patients on a regular basis, such as every two hours. In an embodiment of the present invention, a patient turning protocol can be managed and coordinated with the aid of patient sensors. The system, methods, and devices of the present invention provide a means for continuously monitoring the position, orientation, and activity of one or more patients and help caregivers carry out a prescribed patient turning protocol. The system can display the real-time turn history of patients and indicate to caregivers if a required turn is approaching or past due.

Figure 5:
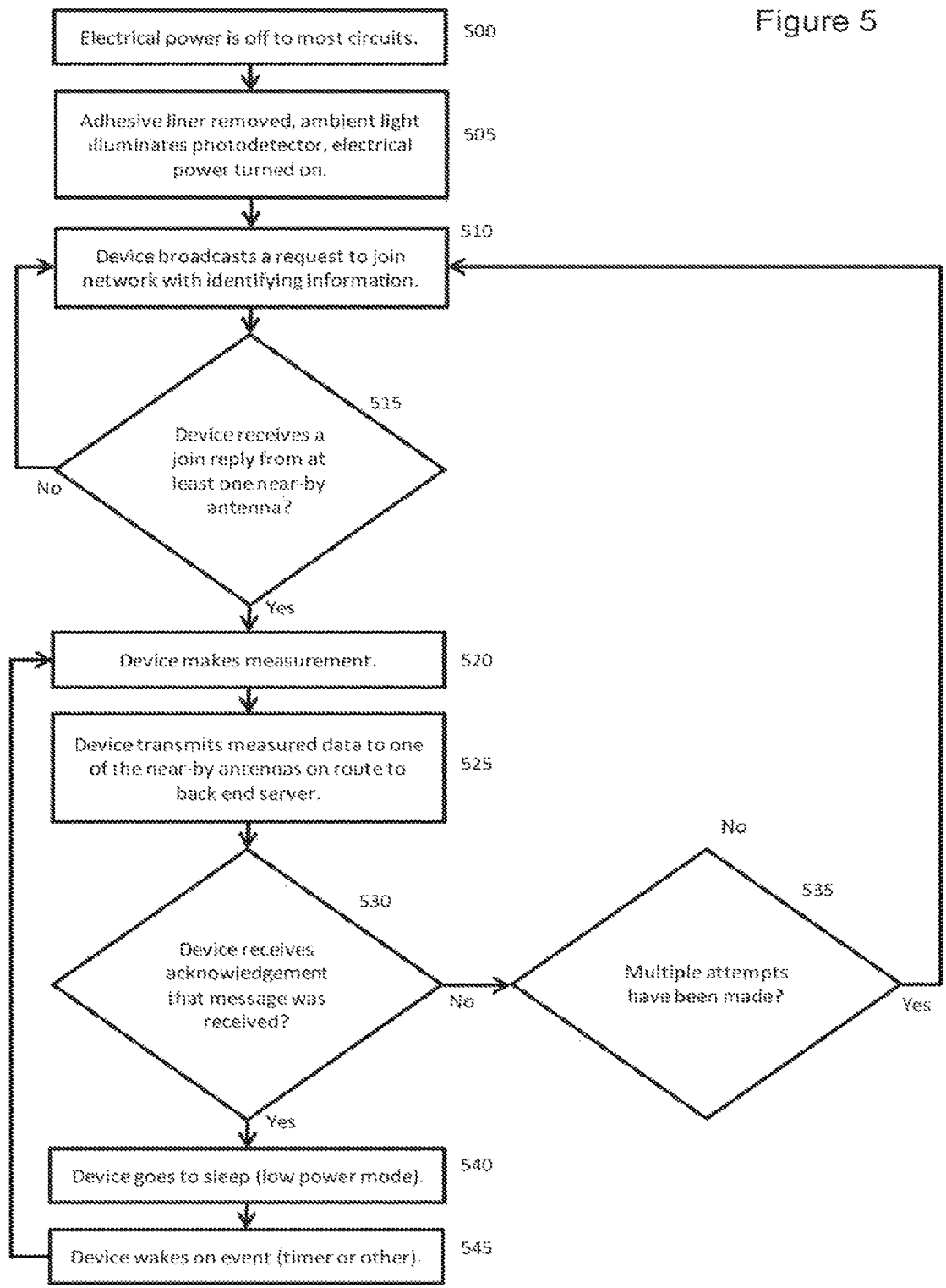
FIG. 5 illustrates a process for powering up devices not connected to a power grid, such as patient sensors, and then integrating them into the network of FIG. 4 as appropriate in some embodiments of the invention.

As discussed above, the sensor itself is a key element in some embodiments of the system, but the sensor is typically powered down prior to association with a patient and, potentially, being affixed thereto. The initialization of components, including a sensor, and their integration into the network of FIGS. 3 and 4 can be better understood in connection with FIG. 5. In particular, FIG. 5 illustrates the power-on initialization and network integration of a device that is not connected to the power grid can be better appreciated. For the sake of clarity, the following discussion will assume a battery-powered device, although such devices can be powered by any suitable means capable of providing sufficient power and portability, for example photo-voltaic cells. An example of such devices are the sensors described above configured to be affixed directly to a patient. For such devices, the process starts at 500, where the state of the device is that power is off except, for example, for a "power-on" circuit such as a phototransistor and related circuitry that responds to ambient light. At 505, upon the removal of an adhesive liner, ambient light illuminates the phototransistor or other photodetector and power is connected to the rest of the sensor. Thereafter, at 510, the newly-powered-on device broadcasts a request to join a network, typically with identifying information as discussed above. If a join response is received from a network at step 515, the process advances to step 520. If no join response is received, the process loops back to step 510 and repeats the broadcast.

At step 520, the device such as a sensor makes a measurement and, at step 525, that measurement data is transmitted to a server for further processing. The transmission need not be near-real time relative to the taking of the measurement, although in many embodiments it will be. The transmission is typically, although not necessarily, made wirelessly, and is thus received at, for example, one of the antennas shown in FIG. 4 and thence to a server.

At step 530, the device checks to see if an acknowledgement has been received, indicating that the server received the data transmitted by the device. If not, the process branches to step 535, where a check is made concerning how many unsuccessful transmission attempts have been made. If a threshold number of attempts have not been made, the process loops back to step 525 and the data is re-transmitted. If a threshold number of repeat transmissions has been reached, the assumption is made that the device has lost communication with the network, for example by the patient walking into a different area of the hospital, and the process loops back to step 510 to enable the device to join whatever network is available for that location.

If the data transmission was successful, as indicated by an acknowledgement at step 530, the device will, for at least some embodiments where power conservation is important, enter a sleep mode as shown at step 540. The device remains in sleep mode until a predetermined event occurs and causes the device to return to full operation. Such events can be elapsed time, a fall, a signal having unusual characteristics, or what may be thought of as an "out-of-bounds" signal indicating some unusual activity by the patient.

Figure 6:
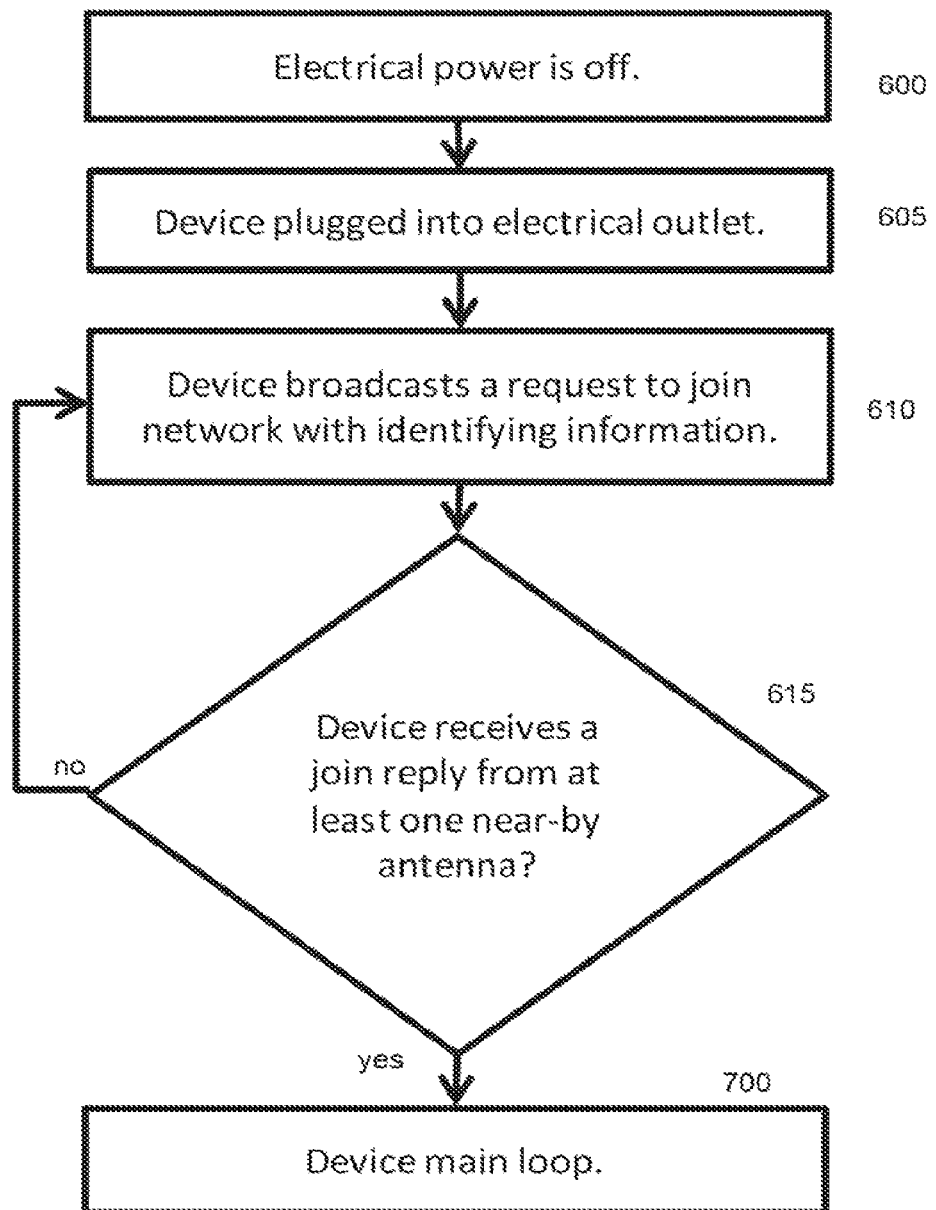
FIG. 6 illustrates a process for powering up network devices such as mesh network transceivers/antennas connected to a power grid and integrating them into the network of FIG. 4 in a manner appropriate to some embodiments of the invention.

Referring next to FIG. 6, the power-on initialization of a network device that is not plugged into the power grid. Such a device may be, for example, the antenna/transceiver combinations that comprise part of the mesh network of FIG. 4. The device starts with power off at 600. Reasonably promptly upon application of power at 605, the device initializes and broadcasts a request to join a network, shown at 610. While in some embodiments the device may be pre-configured for the type of network, in at least some embodiments the device does not know in advance what network is available, and looks for a "join" response from any network. The device typically provides, as part of the broadcast, information that identifies it for at least network purposes. Upon receipt of a join response at 615, the device advances to the device main loop, referenced as 700 and described in connection with FIG. 7. If no join response is received at 615, the process loops back to 610 and the broadcast step is repeated until a join response is received, or the process is otherwise terminated.

Figure 7:
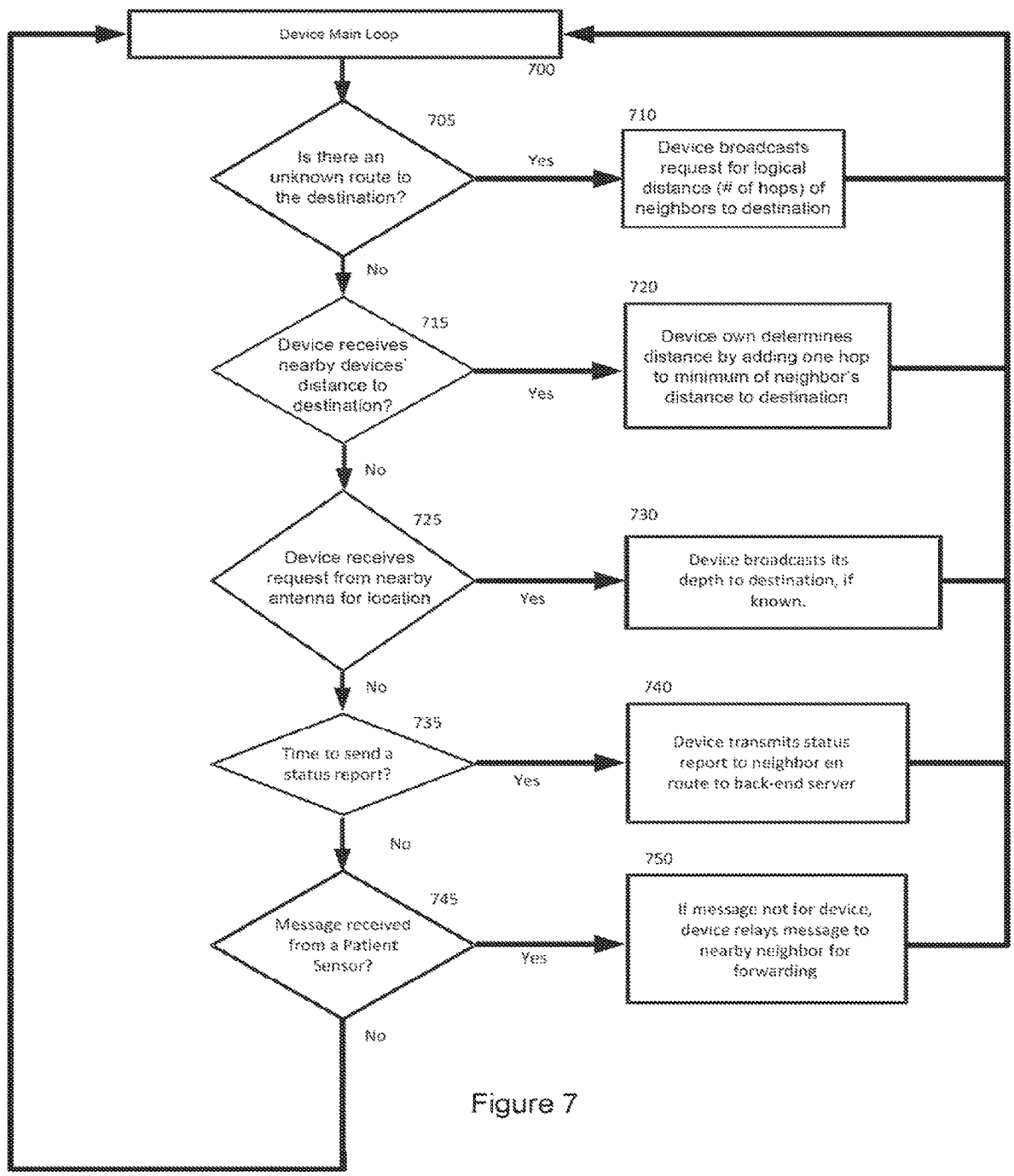
FIG. 7 illustrates a device main loop, such as used by a sensor in accordance with some embodiments of the invention, and by which status updates including, for example, patient position, are provided to the system.

Referring next to FIG. 7, the device main loop referred to above in connection with FIG. 6 can be better appreciated. The process starts at step 700 and advances to step 705, where a query is generated asking if there is an unknown route to a destination. In this context, "route" refers to network topology, where each retransmission represents a "hop" and the most direct route is indicated by the lowest number of hops. Typically, the destination is the location of a sensor or other device capable of providing relevant data to the system, and may be affixed to a patient moving about a hospital or other monitored area. If there is a route that is not known, such that there is a new route to a destination, the process advances to 710 and the device broadcasts a request to neighbors of the destination for information about the logical distance to that destination. The process then loops back to 700 so that the neighbors can supply the necessary information concerning logical distance.

If all routes are known, such that there is no new route or the new route data has now been entered as a consequence of the loop back to step 700, the process advances to step 715, and the device receives information regarding distance to a destination. If the device receives such distance information, the device determines distance on its own at step 720 by adding a value representative of one additional hop to the minimum distance reported by the neighbors, and then loops back to step 700.

At step 725, if the device receives a request from a nearby antenna for distance information to a destination, the process branches to step 730 and the device broadcasts its depth to a destination, if known, after which the process loops back to step 700. At some point for at least some embodiments, a status report is due to be sent as shown at step 735. If so, at step 740 the device transmits the status report to the network, for example via a nearby neighbor, and the status report is then communicated to the appropriate server as shown at step 740.

In some embodiments, messages will be received by the device from, for example, a patient sensor or a server, or other device such as a query from a hospital system. If the message is for the device, the message is acted upon. However, if the message is not for the device, the device relays the message to neighbors en route to the appropriate destination, as shown at step 745.

System Architecture and System Use

The following description elaborates on the discussion of FIGS. 1-5, above, and further describes the architecture of a monitoring and reporting system for managing and coordinating patient-turning protocols in accordance with an embodiment of the invention.

The present invention provides a system for monitoring patient orientation and for alerting caregivers for the need to turn a patient being monitored which is easy to install, easy to maintain, easy to interact with, and reliable. As shown in FIGS. 1-4, an embodiment of a system in accordance with the present invention can comprise the following components:

Patient Sensors
Data Collection Network
Back-end Server
Database
Turn Management Software It will be appreciated that FIG. 4 illustrates one embodiment of such a system. In typical use of such a system, the caregiver uses the turn management software to define an individualized turn protocol for one or more patients that require monitoring. The turning protocol parameters for these individualized protocols are stored in the Database for future reference. The Patient Sensor 110, which is disposable and wireless in some embodiments, is associated (for example, adhesively affixed) to the body of the patient being monitored. The sensor makes measurements of the patient's orientation and communicates this data, wirelessly or by other suitable means, over the data collection network previously set up in the facility. The network relays data from the Patient Sensors to a server computer connected to the data collection network. Software running on the server computer collects the patient data and stores the data into a database for subsequent analysis. The patient's orientation and other patient related metrics can then be determined by analyzing the data stored in the database. The Turn Management Software displays each patient's turn history and current status. The Turn Management Software also alerts staff if any patient requires a caregiver-assisted turn. The system also has the ability to automatically document each patient's turn history (including caregiver-assisted turns and patient self-turns).

A more complete description of each of the system's components is given in following sections:

Patient Sensor

In an embodiment, the Patient Sensor is a single-use, disposable, wireless device that can be adhesively affixed to a patient's skin. The sensor may be reversibly associated with the patient in any fashion. In an embodiment, the sensor itself is comprised of several components: a 3-axis accelerometer to measure patient orientation and activity; a phototransistor that measures ambient light levels and turns on the device when the packaging and/or adhesive liner is removed; a capacitive contact sensor that enables the device to sense when it is attached to skin and sense when it is removed from skin; LED indicators to visually communicate information to the caregiver; a microcontroller for automated data collection, analysis, and storage; an RF radio for transmitting and receiving messages; and a common CR2032 coin-cell battery for providing electrical power. In an embodiment, the skin-contacting portion of the patient sensor is a commonly used polyurethane dressing having an acrylic adhesive. However, any other suitable adhesive may be used.

In an embodiment, the patient sensor is enclosed in an optically opaque pouch that is easily opened by the caregiver at the time of use. While in the packaging, the majority of the circuitry of the sensor need not be powered in at least some embodiments. In this way the shelf life of the device's non-chargeable or non-rechargeable battery can be as much as several years. After removing the device from the packaging, the caregiver needs only to remove the adhesive backing from the underside of the device, exposing the adhesive surface, and then apply the device to the upper torso of the patient. Indicia on the Patient Sensor indicate the proper orientation of the device with respect to the patient. The device contains a photosensitive electronic circuit that detects ambient light. When the device is removed from opaque packaging the ambient light incident on the photosensor activates the device and power is then supplied to the main electronic circuits of the device. Alternately, the adhesive backing can be opaque and when the opaque adhesive backing is removed it enables ambient light to strike the photosensitive circuit. The photosensitive circuit turns on the device when ambient light is detected.

In an embodiment the device provides a visual indication to users that it has successfully powered-up. One method is to provide one or more LEDs that briefly illuminate when the device has powered up.

In an embodiment the device automatically joins the wireless Mesh Network once power has been provided to the device, as discussed in connection with FIG. 6. In an embodiment the Patient Sensor communicates with a nearby Relay Antenna having the strongest RF signal, although other protocols for managing communication between the sensor and the remainder of the network are acceptable as long as communication is reasonably maintained.

In an embodiment the device indicates to users that the sensor has successfully joined the Mesh Network. A method in an embodiment is by showing a pattern of scrolling LEDs (repeatedly turning each LED on and then off in sequence).

In an embodiment the device conserves battery power. After successfully joining the RF network, the patient sensor spends most of its time in a very low power "sleep" mode. On a regular schedule, for example, every ten seconds, the sensor may briefly "awaken" to make measurements and transmit the measured data to a nearby Relay Antenna. Once affixed to a patient, the sensor continues to make measurements every ten seconds until the battery is depleted over a period of greater than about three weeks.

Since RF communication takes significant power, in some embodiments the sensor can measure and store several patient data readings with the RF radio circuitry off. Only after several measurements have been taken would the device turn on the radio and transmit from memory some or all of the measurements recently stored.

Alternatively, sections of the circuitry could continue to make measurements while most of the circuitry is in a low power "sleep" mode. The device could "awaken" due to events detected by the portion of the circuit that was not put to sleep. Such events could be if the magnitude of acceleration is above or below some threshold, the direction of acceleration changes by some amount, the ambient light measured by the device rises above or below some threshold, the device detects that physical contact with the patient is lost, or a combination of more than one these or other events.

In addition to the phototransistor, two additional sensors reside within the Patient Sensor in at least some embodiments: a three-axis accelerometer and a capacitive contact sensor. The three-axis accelerometer is a semiconductor device that is sensitive to accelerative forces, including gravitational forces, applied to the device. By sensing the direction in which gravity pulls on the device, the orientation of the device and thus the position/orientation of the patient can be determined. In order to accurately determine the position/orientation of the patient, it is necessary for the three-axis accelerometer to be oriented correctly with respect to the patient either at the time of affixing the sensor to the patient, or following measurements by the sensor and processed by the system. To aid in orienting the sensor with respect to the patient, in some embodiments the sensor can have indicia to allow for proper placement on the patient. In particular, the housing unit, which houses the accelerometer, can provide a surface for the desired indicia which can be as a mark, arrow, or icon indicating proper orientation. In such embodiments, the orientation of the accelerometer with respect to the housing unit is known or can be determined.

It should be understood that each accelerometer may detect static acceleration (e.g., due to gravity) and/or dynamic acceleration (e.g., due to movement), which may be used for monitoring the orientation of a patient.

A capacitance sensor can be located just inside the bottom surface of the device in some embodiments, and is used to sense the change in capacitance that occurs when the device is affixed to a patient's skin. The capacitance data may be used to determine if the device is attached to (or has become unattached from) the patient. If the device is not attached to the patient, then orientation measurements made by the sensor cannot be trusted to correspond to the present orientation of the patient. The orientation and contact status of the sensor can be displayed in the User Interface of the Turn Management Software used by the caregivers.

If the sensor is wireless, the patient is unencumbered by an umbilical extending from the device. The patient is free to move about, in-bed, or out-of-bed. The patient's movement, position, orientation, and activity can be continuously and seamlessly tracked, regardless of the physical support apparatus they are on.

In an embodiment the sensor is sealed so that a patient wearing the device may shower or bathe as usual. Both optical sensors and capacitance sensors can operate through a sealed enclosure.

In an embodiment the skin-contacting portion of the device is a polyurethane dressing having an acrylic adhesive. This type of dressing is very commonly used in medical practice. The patient may wear the device continuously for many days. Other types of adhesive systems may be used, including hydrogels and silicone adhesive systems.

The Patient Sensor can communicate wirelessly with any neighboring antenna. In an embodiment the patient sensor can transmit and receive messages greater than about five feet. However, many structures in the environment (walls, cabinets, carts, and even the patient's own body) may reflect and/or attenuate the RF transmissions. Practically, it can be desirable to have antennas positioned about every 25 feet to ensure that at least one Relay Antenna is within range of any patient sensors. If the patient is ambulating, the Patient Sensor may not be able to communicate with the relay antenna with which it was initially communicating. If this occurs, in an embodiment the sensor automatically begins communicating with a different, near-by relay antenna that has the strongest RF signal. In this way, the sensor will always stay connected to the wireless mesh network of antennas, selecting a new antenna with which to communicate, as necessary. The messages and the patient data they contain will automatically find their way to the server computer and be stored in the SQL database, no matter what Relay Antenna is communicating directly with the Patient Sensor.

It is preferable that each Patient Sensor has a unique serial number that is assigned to the device either during the manufacturing process or at any other suitable time. The sensor can be uniquely identified on the RF network by this serial number. Alternatively, when the sensor is turned on and joins the wireless mesh network, it may be assigned a unique network address by the back-end server (or other device on the network), by which it is subsequently addressed. Alternatively, the patient sensor can randomly select a unique identifying number after it powers-up. The patient sensor and back-end server can thereafter confirm that the randomly chosen identifying number has not already been used. If the randomly chosen number has already been used by another device in such an embodiment, then the process of choosing a random number is repeated until a unique, previously unused number is determined. The unique serial number can be provided to users, such that the unique device serial number can be linked to a patient, bed, or other patient identifier. In some implementations, the link between the unique device serial number and the patient can be made automatically. In a preferable approach for automatically linking this information, the physical location of the sensor is automatically determined (i.e. the system can determine what bed the sensor is being used on through signal strength analysis, triangulation, and other means). The system then pulls bed/patient information for an electronic health record or ADT (Admission, Discharge, Transfer) database to determine what patient is associated with the bed.

In some embodiments, the patient sensor transmits no patient-identifying information (for example, name, electronic record number, etc.) over the wireless mesh network, since then it is not necessary to encrypt transmissions in order to protect patient privacy. Alternatively, all transmissions or a subset of transmissions can be encrypted just prior to transmission by a means familiar to those skilled in the art.

Data Collection Network

Data measured by the Patient Sensor is typically communicated to a back-end server (a computer or other device responsible for storing the data in a database) as discussed in connection with FIGS. 1A-4D. The data can be communicated from the sensor to the back-end server over a wired network or over a wireless network. A wireless data collection network is preferable in some embodiments because wires or cables do not need to be routed within the facility. Further, as mentioned previously, it is preferable in at least some embodiments that the patient sensor itself be wireless. A properly designed wireless network could be conveniently installed in a short amount of time. Unfortunately, common wireless networks are often unreliable. Common wireless networks may experience interference from other RF communication equipment, other environmental RF noise sources, and environmental obstructions like walls, cabinets, furniture, equipment, and humans moving through the facility. In an embodiment a wireless network would have features that would make it very reliable in spite of these modes of interference.

In an embodiment, a reliable wireless network is created by having a high level of redundancy in the network. An array of antennas arranged in a one, two, or three dimensions, in which any antenna can communicate with one or more nearby antennas form a mesh-like (or web-like) architecture, such as shown in FIGS. 4A-4B. In some arrangements, the antennas do not need to be positioned precisely on a regular grid, but instead, can be plugged into available power sources approximately every five feet to 200 feet. The relay antennas can be powered by any suitably reliable source, such as facility line voltage, a single use or rechargeable battery, a photovoltaic system, etc. Redundant power sources offer a good solution in at least some embodiments and comprise, for example, the facility's line voltage, plus a single use or rechargeable battery inside the device for back-up in the case that the facility power fails.

In an embodiment, the messages sent to or from Patient Sensors over the mesh network are relayed from the source to the destination through sequential transmissions (hops) from one Relay Antenna to the next. Many possible routes from source to destination may exist within the mesh network of antennas. For simplicity, "antenna" or "Relay Antenna" as used herein will be understood to include the associated transceiver electronics unless indicated otherwise by context. Even in a one-dimensional mesh-network, redundancy can be achieved by allowing transmissions to hop over one or more antennas physically located between a transmitting and receiving antenna. In a mesh network architecture, even if one or more antennas are not working, there may still be one or more alternate routes through the mesh network that can be used to transfer the message from the source to the destination.

The web-like architecture of the mesh network ensures there are redundant pathways between the sensor and server. If a Relay Antenna is broken, is removed, experiences RF interference, or is obscured by equipment, cabinets, walls, or people, then messages may be automatically routed around the non-functioning antenna via one of the other redundant routes. The route used to relay a message between the source and destination is ideally determined cooperatively by the individual antennas that make up the mesh network, so as to select a route having a combination of good RF signal strength and few hops. Alternatively, a router device can communicate possible routes to the antennas that comprise the network. The router device could be one or more of the relay antennas or even software running on the server computer that has been given additional responsibility to determine the possible routes and communicate these routes to the relay antennas.

Possible routes can be determined cooperatively without the need for a router device. As discussed in connection with FIG. 7, each antenna can determine its logical distance from the destination of a message. The logical distance of an antenna to a destination is the number of times a message must hop in order to be relayed from the antenna to the destination. The logical distance of an antenna that can communicate directly with the destination is one. The logical distance of an antenna to a destination with which communication cannot be made directly may be determined by an antenna by adding one to the minimum of the logical distance(s) of neighboring antenna(s) to that same destination. An antenna may determine the logical distance of neighboring antennas by transmitting a request to nearby antennas for their logical distance to a specific destination. When an antenna receives a message for a given destination, then, if possible, the antenna and associated transceiver merely transmits the message directly to the destination. Otherwise the antenna/transceiver transmits the message to the neighboring antenna/transceiver having the minimum logical distance from the destination. Possible routes from an antenna to a destination can be limited to those routes that have sufficient RF signal strength to ensure reliable communication between each of the relay antennas along the route. Additionally, routes may be ranked in order of preference by an algorithm that weighs the number of hops and also weighs the link quality of each hop along the route.

In an embodiment, no intervention by the caregiver or IT staff of the facility is required when individual Relay Antennas are temporarily non-functional. When the antenna again becomes functional, it will automatically rejoin the mesh network and preferred routes between the server and patient sensors will automatically be determined. In this way, the mesh network is "self-assembled" and "self-healing". If an antenna is trying to communicate with another antenna that is no longer responding, the first antenna may re-determine its logical distance from the destination and send the message to an alternate neighboring antenna.

Even in a network that is highly redundant, means for ensuring data integrity during communications over one hop from an antenna to a neighboring antenna is desirable. It is preferred that antennas determine if a message has been corrupted during transmission. A preferred method for determining if a message transmitted from one relay antenna to another has been corrupted it to compute a checksum of the message to be sent and include the checksum with the transmitted message. A numerical value may be assigned to each character that comprises a message. For example, the American Standard Code for Information Interchange (ASCII) assigns a unique value for each alphanumeric symbol common used in communication. The checksum may be a simple sum of the numerical values assigned to each of the characters of the message, a modulo sum of the numerical values assigned to each of characters of the message, or may be a more elaborate cyclical redundancy check (CRC) that is one or more bytes in length. Those skilled in the art of data communication are familiar with various check summing algorithms. The receiving antenna may re-calculate the checksum of the message and compare the re-calculated checksum with the checksum transmitted with the message. If the checksums agree, the receiving antenna can notify the transmitting antenna of the successful receipt of the message by transmitting an acknowledgement to the antenna that sent the message. If the antenna that sent the message does not receive an acknowledgement in some period of time, the antenna that sent the message may try to re-send the message. Further, it is preferable for the antenna that sent the message, after one or more un-acknowledged attempts to send the message, to try to send the message via an alternate route to the destination.

In a mesh network architecture in which there are multiple transmitters and multiple receivers that may be attempting to communicate multiple messages there may be times when collisions occur. Collisions occur when two transmitters attempt to communicate at least a portion of their messages simultaneously. In an embodiment, the sensors and antennas use techniques to reduce the likelihood of collisions. One method for avoiding collisions is to perform a clear channel assessment (CCA), and can be implemented in some embodiments. During a CCA the device checks for RF transmissions already in progress or alternately merely checks for significant RF power before initiating a new transmission. If it is determined that a clear channel is not present, the device waits for a period of time before trying again. Prior to each attempt, the device can again perform a CCA. The time delay between subsequent attempts may be a fraction of the time it takes to send a message up to several times the time it takes to send a message. For messages of about 30 characters in length transmitted at a data rate of 250 kilobits per second, this delay time may be from about 10 µs to 10 ms. The time delay between subsequent attempts may be fixed or may increase in some fashion, such as linearly increase or exponentially increase. The time delay between subsequent attempts may be random or pseudorandom in duration. If the transmission of a message is not acknowledged, it may be because a collision occurred even though a CCA was made prior to transmission. If a message is re-transmitted because it was not acknowledged, similar time delay variations as used after failed CCA may be used between subsequent transmission attempts.

A single mesh network can comprise just a few antennas on up to hundreds of relay antennas. Further, multiple mesh networks can be configured within a single facility. Each mesh network may communicate messages from patient sensors to a different back-end server. The back-end servers may store the data contained within the messages to different databases or alternately may communicate the data to the same data base. By communicating data from physically isolated mesh networks having different back-end servers into the same database, the physically isolated mesh networks can be logically treated as a single network by the system. In this way, wards, hospitals, and even hospital chains can be monitored as if they were a single network, if desired.

In an embodiment the system allows facility staff to administer the system. Patient Sensors and Relay Antennas can generate regular status reports and send them as messages to the back-end server. Status reports can be generated when specific events occur, such as when a device (sensor or antenna) is powered on, when a device joins or rejoins the network, or when new neighboring devices are detected. Status reports may also be generated at regular time intervals and include information like how many messages were received, how many messages where corrupt, how many messages needed multiple attempts to transmit, or how times an antenna needed to recalculate its routes. In an embodiment, software running on the back-end server collects and analyzes the reports made by sensor modules and/or antennas. In an embodiment the back-end server communicates alerts to facility staff based on the analysis of the reports from sensor modules and/or relay antennas. The back-end server alerts the facility staff if some period of time has passed since the last status report from a relay antenna or patient sensor. Such an alert would occur if an antenna was removed, broken, or experiencing some type of interference. The back-end server could provide other alerts based on the information provide in the status reports. The back-end server could assimilate the data from the reports and provide regular summary reports of the status for the system. The back-end server could communicate the alerts and summary reports via text messages, email, a paging system, or website. Alternately, it provides the alerts and reports as files available to users that have access to the back-end server.

It is desirable that, in at least some embodiments, the RF network use low power transmissions so that battery life of the patient sensor and relay antenna be extended. Low power transmissions also limit RF interference induced in other equipment used in the facility. Low power transmission also limits the interference with medical and electronic devices used by the patient; for example, pace makers, defibrillators, cell phones, or personal computing devices. A preferable frequency and power level is about 2.4 GHz and about 1 mW.

Back-End Server Software and Database

In an embodiment messages sent by the Patient Sensors are communicated by the data collection network to a back-end server computer running data collection software. Preferable, the back-end server has a means for connecting to the data collection network. For a wired data collection network, a Network interface card may connect the back-end server to the data collection network. For a wireless data collection network, an RF transceiver may connect the back-end server to the data collection network. The primary purpose of the back-end server is to collect patient orientation data and save the data into a database. Other tasks may be performed by the back-end server such as assigning network addresses to Patient Sensors and Relay Antennas as they join the mesh network, and collecting other miscellaneous data from the Patient Sensors and Relay Antennas such as status reports and other network information.

In an embodiment, the back-end server may send messages to devices comprising the data collection network. Such messages may be commands to perform a self-test, turn off the main circuits of the device, or to modify operating parameters such as radio power, measurement frequency, or other operating parameters.

A system in which more than one back-end server is provided for each physically isolated mesh network is preferable for some embodiments in that it increases reliability through redundancy. In normal operation, messages to and from a patient sensor may be routed through the back-end server that has the shortest logical distance from the patient sensor. This architecture also has the benefit of increasing total bandwidth since message traffic is divided between the multiple back-end servers. In the case that one of the back-end servers stops working, or its connection to the database is lost, the message traffic will may automatically be re-routed through other available back-end servers.

It is also desirable that the database be reliable. If the database is stored on hard disk drives, then the use of mirrored hard drives or other configurations of redundant disk arrays is preferable. In some embodiments, the hard drives or hard drive arrays can have redundant drive controllers and redundant interfaces to the one or more back-end servers, or otherwise provide high availability.

It is desirable that any of the one or more back-end servers have software or other means that monitors the performance of the back-end server. The back-end server monitor can automatically reset or restart the back-end server if the back-end server does not function properly. In an embodiment the back-end server monitor is capable of alerting facility staff via email, text messages, paging systems, or a website if problems are detected.

In an embodiment, the data exchanged between back-end server and the database contains no patient-identifying data such as patient name or patient electronic medical record number which obviates any concern about data security on any data links between the back-end server and the database.

With the operation of the sensor and network in mind from the foregoing, the following discussion of a sensor-assisted turn management system can be better appreciated. It will be appreciated by those skilled in the art that many aspects of the turn management system of the present invention are implemented in software operating to define the functions performed by the servers, database(s), and related hardware previously discussed. When implementing a sensor-assisted turn management system, there are various turning parameters, algorithms, and data analysis techniques that can be incorporated to substantially improve the clinical usability and utility of the turn management system. These items are discussed hereinafter.

In general, turning protocols are based on regularly alternating a patient's surface pressure distribution between two or more body regions, such as their back side, right side, or left side. An embodiment of the present invention enables the pressure distribution across body regions to be monitored and managed in a more sophisticated, accurate, and reliable way.

Turning protocols are generally based on a desired turn period, which is set by caregivers. A turn period reflects the amount of time that a patient can stay on any given body region before a turn is required under the protocol set by the caregiver. As shown at 800A-B in FIG. 8, in at least some embodiments of the present invention, turn periods are a configurable setting. Turn periods can dynamically change based on patient, environment, or institution specific variables. For example, the turn period may change based on the patient's risk of developing a pressure ulcer (which can be a value manually entered into the system, automatically extracted from a medical record, or automatically calculated based on sensor data collected in 800A). Still further, the turn period can dynamically change based on the patient's physical support apparatus, patient's health status, presence of existing pressure ulcers, time of day, caregiver staffing ratios, or virtually any other care-related variable.

Figure 8:
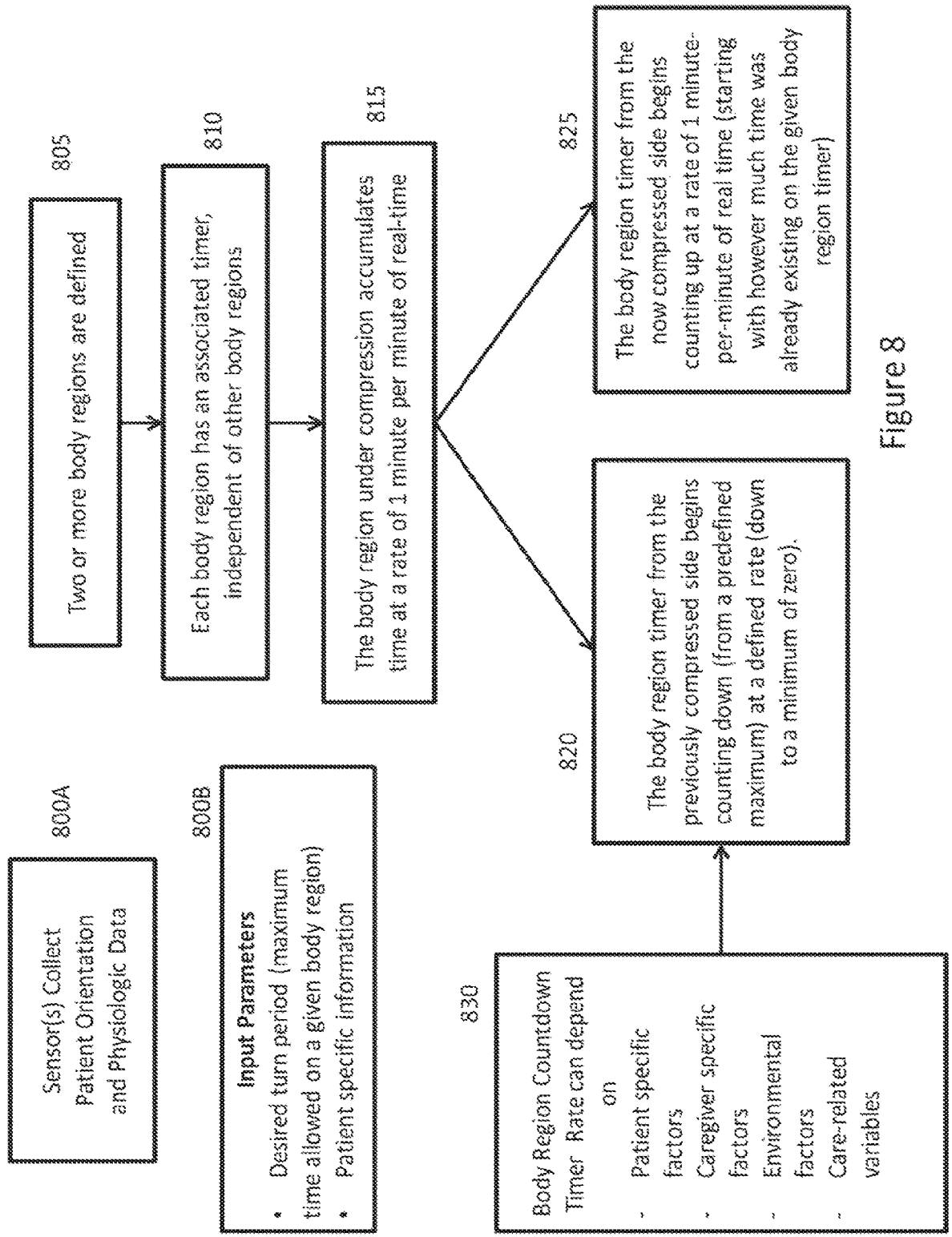
FIG. 8 illustrates a process in accordance with the invention for monitoring body region compression and decompression times.

Still referring to FIG. 8, for each patient, or group of patients, caregivers can define acceptable body regions as shown at 805. In an embodiment of the present invention, angle thresholds can be used to define the body regions. The orientation of the patient (across one or more axes) is determined by one or more sensors that are associated with or affixed to the patient, for example, the sensors that are described in Appendices A and B, the patient sensor(s) communicate patient orientation data to a host, which compares the calculated patient orientation to pre-defined body region threshold angles, so as to determine the body region(s) that are currently pressurized. For example, if it has been defined that the back side angle thresholds are −30 and +30 degrees, the patient will be considered to be lying on their back when they are between those angles.

It should be noted that defining body region threshold angles is not a requirement. It is possible to simply display the angle of a patient (in one or more axes), without defining the patient's position. However, providing a gross assessment of a patient's position may make the system easier to use and may make the system more consistent with traditional turning protocols (which typically define a back side, left side, and right side).

In an embodiment of the present invention, the cumulative amount of time spent in any given body region can be calculated by the monitoring system. As shown at 810, in an embodiment the system assigns a timer to each defined body region. The system then can calculate the amount of uninterrupted or continuous time a given body region spends in either a compressed or decompressed state, as well as the total body region time accumulated, for either compression or decompression, within a specified time period (i.e. total amount of time spent in a given body region over 24 hours). Time thresholds for providing alerts and notifications to staff can be programmed into the monitoring system.

Typically, a turn is defined as moving from one body region to another, such as moving from the back side to the right side. When angle thresholds are used to define body regions, a potential problem arises when low magnitude turns (i.e. "microturns") occur around the defined body region threshold angles. For example, if it has been defined that the back side angle thresholds are −30 and +30 degrees, a patient may get credit for turning if they move from +29 (back side) to +31 degrees (right side). Although the patient may have technically moved between body regions, they moved by only 2 degrees, which probably is not a clinically significant turn. Methods for determining when an adequate turn has been performed, and thus addressing the problem of "microturns", comprise one aspect of the invention and are included in some embodiments.

In an embodiment of the present invention, caregivers can define the minimum patient orientation change that is required in order to conclude that an adequate turn has been performed. Returning to our previous example, if a minimum orientation change had been defined (i.e. >15 degrees required for a turn), the patient would not have received turn credit for moving from +29 to +31.

In implementations where it is desired that minimum orientation changes are required for turns, the system of the present invention can be designed such that the body region threshold angles also dynamically change. Returning again to the prior example, if a patient is at +29 (back side) and a minimum orientation change of 10 degrees has been incorporated into the system, the use of a dynamic body region threshold angle would require that the patient rotate to +39 degrees before they are considered turned onto their right side.

In clinical practice, patients generally don't stay fixed at a specific angle within a body region for an entire turn period. In reality, a patient's orientation typically fluctuates within a body region during any given turn period. In some instances, a patient may also very briefly rotate onto a different body region, before quickly returning back to the original body region. These quick "turns" may, or may not be, clinically significant. In some implementations of the present invention, it may be desirable to compute the average orientation angle that a patient maintains during a given turn period. This orientation averaging may be particularly relevant if dynamic body region threshold angles and minimum orientation angle changes are being used. For example, if a patient is lying on their back (i.e. initially defined as −30 to +30 degrees), and their average orientation over the turn period is +25 degrees, the patient would need to turn to at least +35 degrees in order to get credit for a turn and to be considered on their right side (assuming a 10 degree minimum orientation change).

In some embodiments, it may be desirable to set a minimum amount of time that a patient must spend within a new body region before getting "credit" for a turn. For example, if a patient changes position from +25 degrees (back side) to +35 degrees (right side), but only maintains that new position for a few moments before returning back to +25 degrees (back side), this quick turn may not be a clinically significant in terms of, for example, permitting decompression of the body region In order to ensure that turns are clinically significant, a threshold amount of time may need to elapse before credit is given for a turn. For example, it may be defined that a minimum turn threshold time of 10 minutes is required before a turn is counted. After any given turn, if a patient turns back onto the prior body region before the minimum turn threshold time has elapsed (i.e. 10 minutes), then credit for the turn is not given. Alternatively, a sequence of turns may be accumulated to aggregate either compression time, decompression time, or both, to permit a more complete assessment.

The concept of incorporating minimum turn time thresholds relates to tissue decompression times. The decompression time reflects the amount of time that a given body region needs to be offloaded before it is considered fully decompressed/re-perfused. Full decompression implies that adequate tissue reperfusion of a given body region has occurred, and thus the risk for ischemic injury has been negated. In some implementations of the present invention, a decompression time can be set and may be configurable. For example, a user such as a caregiver may choose a decompression time of 15 minutes, which implies that if a body region is decompressed for at least 15 minutes, this body region will be considered fully decompressed/reperfused. After the decompression threshold has been surpassed, the patient may be allowed to turn back onto the decompressed body region.

In some implementations of the present invention, each body region may have an individual timer that reflects the degree of compression/decompression permissible for that body region, as shown at 810 in FIG. 8. The rate at which the body region timer counts up or down may vary depending on the clinical scenario. In addition, the rate at which a body region timer counts up may be different than the rate at which it counts down. For example, consider a situation where the turn period has been set to 120 minutes, with a decompression time of 15 minutes. If a patient moves onto a specific body region, the body region timer may begin counting up at a rate of 1 minute for every minute of real-time, as shown at 815 in FIG. 8. At 120 minutes, an alert may be provided to caregivers indicating that a turn is due. In addition, various alerts (potentially escalating) may be provided to caregivers as the timer approaches 120 minutes and/or after the timer exceeds 120 minutes. Beyond 120 minutes, the timer may continue to count up at the same rate, a different rate, or may stop counting up altogether. In some implementations, once the turn period has been exceeded, the body region timer may indicate only the past due time or alternatively can indicate the total time elapsed on a given body region.

In some implementations, if a patient were to turn off of a body region, the body region timer from the previously compressed side may begin counting down, while the body region timer from the newly compressed side may begin counting up, shown at 820 and 825 of FIG. 8. The rate at which the timer counts up/down can be configured, and may be related to the desired tissue decompression time. For example, consider a patient on a 120-minute turn period with a desired decompression time of 15 minutes. If this patient accumulated 120 minutes of time on a body region before turning, the previously compressed body region timer would count down at a rate of 8 minutes for every 1 minute of real-time (i.e. the body region timer would be reach 0 minutes after 15 minutes of real-time). If the patient were to turn back onto a previously compressed side before the body region timer had reached 0 minutes, the timer would again starting counting up at a rate of 1 minute per minute of real-time (or any other programmed rate).

In some implementations, the body region timers may have maximum and minimum values. The maximum value may be related to the turn period. For example, if the patient is on a 120-minute turn period, the body region timer may max out at 120 minutes. Therefore, if a patient is on a given body region for more than 120 minutes, once the patient turns, the body region timer will begin counting down from 120 minutes at a given rate (i.e. 8:1 for a 15 minute decompression time). In other implementations, the body region timer has no maximum values, and the countdown that occurs upon turning will begin at whatever the total elapsed time is for the body region timer.

To further illustrate how body region timers work, consider a patient on a 120-minute turn period with a 15-minute decompression time, where the given patient compresses a body region for 30 minutes. If this patient then turns onto a new body region, the previously compressed body region timer will count down from 30 minutes at a rate of 8:1, such that the body region will be considered full decompressed within 15 minutes. If the patient turns back onto the previously compressed side before complete tissue decompression has occurred, the body region timer will begin counting up from the new starting time (i.e. if the turn was only maintained for 2 minutes, the body region timer will begin counting up from 14 minutes, given that the patient was awarded 8×2 minutes=16 minutes of decompression).

In some implementations, the body region timer might not begin counting down until a threshold amount of offloading time has occurred. For example, if a patient performs a turn, the body region timer from the previously compressed side might not start counting down until the turn has been maintained for a threshold amount of time (i.e. 5 minutes). After the threshold has been met, the body region timer may begin counting down at any rate.

It should be noted that the rate at which a body region timer counts up or down does not necessarily need to be linear. The body region timer can progress in a stepwise, exponential, or logarithmic fashion. The rate at which the timer counts up/down can vary depending on virtually any care-related parameter, such as patient risk level, presence of existing pressure ulcers, health status of patient, physical support apparatus type, time-of-day, caregiver staffing ratios, location in the hospital, etc., as shown at 830. The body region timers can also function differently for different body regions, such that each body region timer may operate with a different set of rules. Furthermore, patient, caregiver, or environmental factors can influence each body region timer. The body region timers may also be influenced by the frequency or magnitude of turns. For example, if a patient turns from +31 degrees (right side) to +29 degrees (back side), the body region timer for the previously compressed side may count down at a relatively slow rate, such as 2:1. However, if the patient were to turn from +31 degrees (right side) to −31 degrees (left side), the body region timer for the previously compressed side may count down at a relatively fast rate, such as 16:1. In this scenario, the higher magnitude turn is awarded a faster decompression time because the higher magnitude turn is associated with better pressure relief. There are various alternative implementations of body region timers, which are all possible given the teachings herein.

In an embodiment of the present invention, caregivers are provided with various notifications and alerts (potentially escalating) when a patient turn is approaching or past due. Described herein is a method for pausing alerts and notifications. When an alert/notification is issued, a user may choose to pause or "snooze" the alert/notification for a preset amount of time. This pausing functionality can be useful in situations where a turn is not immediately possible due to patient or caregiver circumstances.

The systems, methods, and devices described herein can be used to help manage, coordinate, and optimize patient turning protocols. In some implementations of the present invention, it may be desirable to analyze the historical turning behaviors for one or more patients, and to determine how closely a given turning protocol is followed. Described herein are novel ways of determining how closely a turning protocol is being followed. These data analysis techniques can be applied to a single patient or a group of patients. There are various ways modifying the formulas outlined below, but the general concepts remain the same.

One method of measuring how closely a turning protocol is being followed is to calculate the compliance, which can be done in several ways. Below are four alternatives for calculating compliance:

1. Compliance (% Time):

Compliance can be calculated as a function of the percent of time that a patient is compliant with a turning protocol. In the equation below, the "total amount of time that a patient is compliant" is calculated based on the total amount of time accrued when the patient is in a state where the turn period has not expired. The denominator reflects the total time amount of time that a patient was monitored (i.e. total time accrued in expired and non-expired turn period states). For example, if a patient was monitored for a total of 24 hours and 16 of those hours occurred in a state where the turn period had not expired, the compliance rate would be 16/24=66%

$$\text{Compliance(\% time)} = (\text{Total time that patient is compliant})/(\text{Total time that patient is monitored})$$

2. Compliance (% Time)+Grace Period:

Compliance can be calculated as a function of the percent of time that a patient is compliant with a turning protocol, with the incorporation of a grace period. A grace period can optionally be incorporated into the compliance calculation, such that the calculated compliance is not negatively impacted until the grace period is surpassed. A grace period provides a small amount of time for nurses to perform a turn after a turn period has expired, whereby if the turn is completed before the grace period expires, the compliance is not negatively effected. In the equation below, the "total amount of time that a patient is compliant" is calculated based on the total amount of time accrued before a grace period is exceeded. The denominator reflects the total time amount of time that a patient was monitored (i.e. total time accrued in expired and non-expired turn period states). For example, if a patient was monitored for a total of 24 hours and 20 of those hours occurred before a grace period expired, the compliance rate would be 20/24=83%. Once the grace period expires, the patient may be considered non-compliant for the total time elapsed since the turn period first expired. For example, if the grace period is set at 15 minutes, and a patient is turned 16 minutes after the turn period expired, the patient may be considered non-compliant for the full 16 minutes. However, if the previous patient is turned 14 minutes after the turn period expired, they will not accumulate any non-compliance time. However, in other implementations, if the grace period expires, the patient may be considered non-compliant for time accrued only after the grace period expired, as opposed to the total time since the turn period expired. In general, the incorporation of the grace period will increase the calculated compliance rate.

Compliance(% time)+GP=(Total time that patient is compliant)/(Total time that patient is monitored)

3. Compliance (% Turn Periods):

Compliance can be calculated as a function of the total number of compliant turn periods divided by the total number of turn periods. The total number of turn periods can be calculated by dividing the total amount of time a patient is monitored by the patient's turn period interval, with the resultant quotient rounded to the nearest integer value. Alternatively, the turn period intervals can be defined based on predefined time intervals (i.e. 2 am-4 am, 4 am-6 am), or by predefined turn schedule times for the institution, or by any other method. To further illustrate, consider an example where the number of turn periods is calculated based on dividing the total amount of time a patient is monitored by the patient's turn period interval. If this patient is monitored for 24 hours and is on a 2 hour turn period, the patient would have a total of 12 turn periods. If a patient exceeds their turn period in any of those 12 turn periods, they would be considered "non-compliant" during each of those turn periods. Therefore, if a patient is non-compliant in 4 of the 12 turn periods, the overall compliance rate would be 8/12=66%. It should be noted that the turn period intervals could also be reset following an adequate turn.

Compliance(% turn periods)=(Total # of compliant turn periods)/(Total # of turn periods)

4. Compliance (% Turn Periods)+Grace Period:

Compliance can be calculated as a function of the total number of compliant turn periods divided by the total number of turn periods, with the incorporation of a grace period. A grace period can optionally be incorporated into the compliance calculation, such that the calculated compliance is not negatively impacted until the grace period is surpassed. A grace period provides a small amount of time for nurses to perform a turn after a turn period has expired, whereby if the turn is completed before the grace period expires, the compliance is not negatively effected. The total number of turn periods can be calculated by dividing the total amount of time a patient is monitored by the patient's turn period interval, with the resultant quotient rounded to the nearest integer value. Alternatively, the turn period intervals can be defined based on predefined time intervals (i.e. 2 am-4 am, 4 am-6 am), or by predefined turn schedule times for the institution, or by any other method. To further illustrate, consider an example where the number of turn periods is calculated based on dividing the total amount of time a patient is monitored by the patient's turn period interval. If this patient is monitored for 24 hours and is on a 2 hour turn period, the patient would have a total of 12 turn periods. In order to get credit for turning during any given turn period, a turn must be completed before the grace period expires.

Compliance(% turn periods)+GP=(Total # of compliant turn periods)/(Total # of turn periods)

In addition to compliance, another metric for assessing how closely a turning protocol is being followed is the "severity of non-compliance". The severity of non-compliance is a measure that reflects the severity or magnitude of non-compliance events. The severity of non-compliance, can be calculated in many ways, but one general method is to compute the median amount of time accrued after a turn period expires. Higher values indicate a more severe the degree of non-compliance. As with the compliance metrics, the severity of non-compliance can be calculated for individual patients or groups of patients, and can be analyzed over a variety of time intervals (i.e. hours, days, weeks, months, quarters, etc.).

Another assessment tool provided by the system described herein allows users to measure how long it takes for a patient to be turned once a turn notification/alert is issued. This assessment tool can be applied to individual patients or nurses, or groups of patients or nurses. The assessment tool can be used to determine workforce needs and serve as a measure to track workforce improvement or identify areas of improvement.

Another assessment tool provided by at least some embodiments of the system described herein allows users to measure the efficiency of patient-turning efforts. The efficiency metric captures the degree to which caregiver-assisted turns are performed when clinically warranted or necessary. An "unnecessary caregiver-assisted turn" is any caregiver-assisted turn that is considered clinically unwarranted given its temporal proximity to an adequate patient self-turn. The degree of temporal proximity required in order for a turn to be considered unnecessary can be configured. For example, if a caregiver turns a patient 20 minutes after an adequate patient self-turn, that caregiver-assisted turn could be considered unnecessary. As the percentage of unnecessary caregiver-assisted turns increases, the institutional turning efficiency decreases. A turning efficiency of 100% means that every caregiver-assisted turn was clinically warranted. A lower turning efficiency indicates that nursing resources are not being used efficiently and could be re-allocated more effectively based on individual patient needs. In order to measure turning efficiency, there needs to be a means for differentiating between patient self-turns and caregiver-assisted turns. In accordance with the present invention, several methods can be used to identify caregiver-assisted turns. In an embodiment of the present invention, caregiver-assisted turns can be manually entered into the system through a user interface, or noted in the system by interacting with the patient sensor (i.e. double tapping the sensor), or by separately documenting caregiver-assisted turns in a logbook or other electronic medical record. Using these methods for documenting caregiver assisted turns, or any other acceptable method, the turning efficiency can be calculated by the following equation:

Turning efficiency(%)=[(Total # of caregiver-assisted turns)−(Total # of unnecessary turns)]/(Total number of caregiver-assisted turns)*100

The system, methods, and devices described herein can be used to measure turning protocol compliance, severity of non-compliance, and other performance metrics. The system can track and issue a number of reports that can be used to aid a facility in workforce management, efficiency improvement, and outcomes improvement. The system can provide reports for any given patient, group of patients, unit, facility, or group of facilities. The system can provide reports over any specified time frame. The system can also take in other data regarding workforce staffing (such as caregiver schedules and shifts), to determine which caregivers or group of caregivers are compliant and where there is need for improvement or more staffing. The system can take into account different staff types and training levels to help determine which level of staff is optimal. This data can be used to help improve the efficiency of the system, by determining necessary staffing levels and identifying where the available staff can be deployed most effectively.

Some embodiments of the system described herein can be used to track the patient census size, and also monitor characteristics of the census, such as the average pressure ulcer risk level, etc. Metrics such as the average pressure ulcer risk level of the census, ambulation level, Braden score, isolation patients, and other patient characteristics can be used to determine required staffing numbers and ratios. These metrics can also be correlated to turning compliance data, severity of non-compliance data, pressure ulcer incidence rates, and other statistics to determine what impact these metrics have on patient outcomes. The system is also able to track events, such as training programs, new hires, audits, conferences, etc. to determine the effect that such events have on compliance and other statistics.

Turn Management Software

A user interface to the system is provided by the Turn Management Software. The Turn Management Software accesses the SQL database, analyzes the data, and displays in near real-time the relevant information. Caregivers using the system can customize a turn protocol for each patient being monitored. The software alerts caregivers when a patient has been in an orientation for a duration longer than was specified by the individualized turn protocol.

After a Patient Sensor has been applied to a patient for whom monitoring is desired, the Turn Management Software can be used to easily assign the sensor to the patient. During the assignment process, the patient's name, electronic medical record number, and bed can be entered. Additionally, the maximum time a patient is permitted to be continuously on a side may be modified if the default value is not desired. If there is a side of the patient's body that the patient should not be on because of an existing wound or other medical issue, the restricted side may be entered. Upon completing the assignment, the Turn Management Software will display whether the patient is on his back, left side, or right side, and when the next turn is required, and additional information including if the patient is prone or upright. If a patient completes an adequate self-turn, credit is given for the turn and the turn period is reset.

There are additional advantages to using the Patient Monitoring System. Since both patient self-turns and caregiver-assisted turns are logged by the system, there is no need to provide assistance to a patient that has recently self-turned, and therefore no alert is issued. This saves the caregiver the time and energy of having to perform a turn that is clinically unnecessary, given that the patient is adequately turning on his or her own. In such a fashion, the system reduces the overall number of unnecessary caregiver-assisted turns. Further, the system makes it financially practical to place a greater fraction of patients on turn protocols. This is because patients that have moderate to good levels of mobility will likely perform unassisted more frequently. Placing patients with greater mobility on a turn protocol administered by the Patient Monitoring System does not burden caregivers to the extent that a manual system would. Using the Patient Monitoring System, caregivers are freed of having to manually monitor patient orientations, and caregiver attention is required only when a patient fails to adequately self-turn. In such a fashion, caregivers are able to focus their attention on those who need it most, while at the same time ensuring that no patient is neglected.

The user interface is designed to show the status of any patient in the facility. The Turn Management Software allows the caregiver to select and change the ward or unit of interest. This makes the system appropriate for single wards/units, complete hospitals, or even hospital chains. Additionally, reports may be generated showing the turn history of patients throughout the facility that is being monitored by the system, or any fraction of the facility. The system can track the turning protocol compliance (and other metrics) for individual wards/units, an entire hospital, or groups of hospitals.

Depending upon the embodiment, different permission levels are assigned to various users, for example by IT staff, to give nursing administrators the ability to change the default turn periods that caregivers are ultimately able to select. In some embodiments, administrators can also change the default decompression time—the time duration any side should be "off loaded" in order to fully reperfuse a region of the body. The threshold angle through which a patient must be turned for the system to recognize the change in orientation as a turn, and the threshold angle that defines if a patient is upright can also be configured by a user with appropriate privileges. The ability to generate and view reports is also enabled or restricted based on configurable user permissions.

In an embodiment, the installation of the Patient Monitoring System uses and application virtualization product, such as Citrix Xenapp, to serve the Turn Management Software to virtually all common desktop or mobile computing devices, including Microsoft Windows and Apple desktop systems, iPads, and android tablets. A "thin client" such as a web browser is all that is necessary on the caregiver's device. In this way, the caregiver experience can be easily controlled through tools provided by Citrix. A dedicated server computer having Citrix Xenapp installed can be configured and provided by Leaf Healthcare, Inc. or the Turn Management Software can be installed on an existing Citrix system already in use at the caregiver's facility. Alternatively, the Turn Management Software is a native Microsoft Windows application, and can be run natively on Microsoft Windows computing devices. Depending on how the system is configured, users are authenticated by either the Citrix logon process or alternatively by logging onto the windows machine on which the application is running. In installations that use Citrix Xenapp, for example, data security is ensured by encryption performed by Xenapp. Alternatively, if the Turn Management Software is running natively on a caregiver's computer, then patient specific data will be transferred between the SQL database and the caregiver's computer and appropriate measures should be taken by the hospital's IT staff to ensure security of patient information.

Tools provided by Citrix enable the facility to configure Xenapp with the appropriate level of computing resources necessary to achieve the level of reliability and redundancy desired by the healthcare facility.

The high degree of configurability of the Patient Monitoring System gives the IT and nursing staff of the facility in which it is used the flexibility to decide how best to implement the system. A status board and/or computing device may be positioned at the central nursing station to give caregivers access to the Leaf User Interface. Additionally, a display device providing caregiver access to the Leaf User Interface can be positioned in each patient's room. The use of mobile computing devices such as laptops or tablet computers can enable dedicated turning teams to easily check which patients are due or soon due for an assisted turn.

The following section describes the specific elements of the Patient Monitoring System:

Patient Data

The system stores, in one or more data structures, data associated with the a patient taken from a list including: first name, last name, full name, date of birth, year of birth, month of birth, day of birth, medical record number, patient identifier, date of admission, time of admission, date of discharge, time of discharge, indicator of whether patient is actively monitored, indicators of pressure ulcer risk, Braden score, Norton score, patient's turn period, areas to avoid pressure, locations of pressure ulcer(s), locations of wounds, age, weight, ambulatory status, fall risk, indicator of whether patient has one or more pressure ulcers.

Facility Data

The system stores, in one or more data structures, data associated with the facility taken from a list including: number of wards, number of rooms, names of wars, names of rooms, types of wards, types of rooms, number of beds, types or beds, names of beds, room identifiers, ward identifiers, bed identifiers, indicators of whether a room, ward, or bed are active or occupied.

Settings Data

The system stores, in one or more data structures, data associated with settings for a system implementation taken from a list including: turn period, default turn period, available turn periods, selected turn periods, pause interval, default pause interval, available pause intervals, selected pause intervals, decompression interval, default decompression interval, available decompression intervals, selected decompression intervals, turn angle, default turn angle, available turn angles, selected turn angles, upright angle, default upright angle, available upright angles, selected upright angles, grace period, default grace period, available grade periods, selected grace periods, capacitive threshold, default capacitive threshold, available capacitive thresholds, selected capacitive thresholds, a threshold for the number of consecutive attached entries for a sensor to be considered attached, a threshold for a the number of consecutive unattached entries for a sensor to be considered unattached, a time indicator for the amount of time that the home screen has not been updated before informing a user that the home screen has not been updated.

Turn Angle

Figure 9:
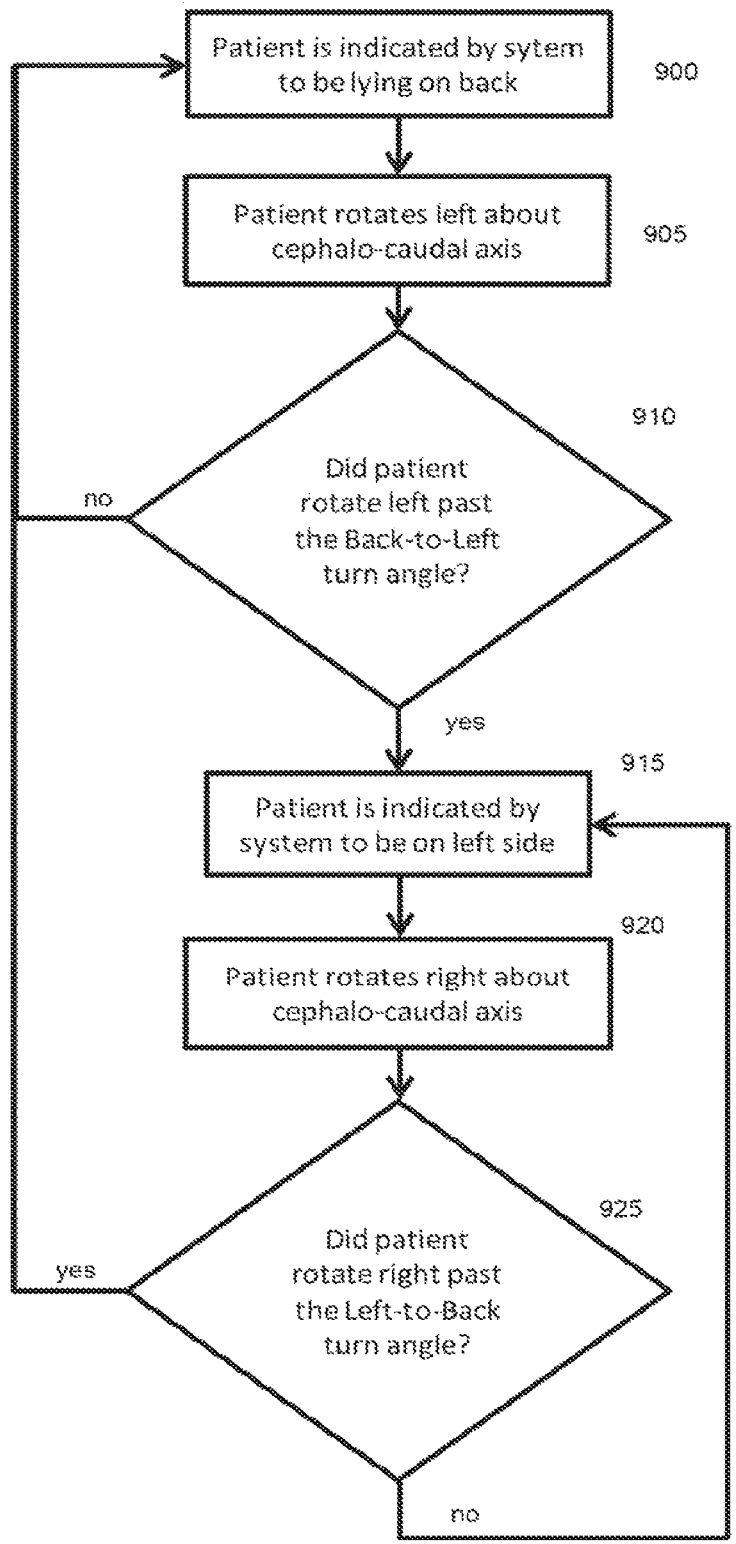
FIG. 9 illustrates a system flow for detecting and recording a patient's rotation about the cephalo-caudal axis.

In at least some embodiments, the system has threshold settings at which the patient is considered to be in certain orientations. FIG. 9 illustrates the manner in which left-right turns about the cephalo-caudal axis are assessed. For example, FIG. 9 starts at step 900 with a patient determined by the system to be laying on their back. As indicated at 905, the patient rotates, either on their own or with the aid of a caregiver, left about his/her cephalo-caudal axis. A determination is made at step 910 as to whether the patient rotated far enough left to go past the predetermined "Back-to-Left-Turn" threshold angle. This angle threshold is the back-to-left turn angle. If so, the patient has moved from lying on his/her back toward the left side and is now considered to be on his/her left side, as indicated at 915. Similarly, the back-to-right turn angle is the threshold angle at which the patient is considered to be on his/her right side. The back-to-right and back-to-left threshold angles are clinically independent, and may be the same or different. Similarly, if the patient is on his/her left side and turns towards the back side, as indicated at 920, the angle threshold at which the patient is considered to be on his/her back side is the left-to-back turn angle. As before, a determination is made, for example based on sensor data, that the left-to-back threshold angle was exceeded, and so the patient is now identified as being on his/her back, as shown at 925.

Note that the left-to-back turn angle does not need to be the same as the back-to-left turn angle. Some embodiments of the system can include hysteresis by allowing for different angles for the left-to-back and back-to-left turn angle thresholds. For example, in the case where the left-to-back turn angle is closer to the patient being on the back and the back-to-left turn angle is closer to the patient being on the right, the system may avoid rapidly switching characterizing the patient as being on the back and left side. The difference between the left-to-back and back-to-left turn angles may be set as a constant difference, a ratio, a function, and it may depend on the patient, patient characteristics, patient turn characteristics, or facility characteristics.

A similar relationship exists between the right-to-back and back-to-right turn angles and the right-to-prone, prone-to-right, left-to-prone, prone-to-left turn angels. Depending upon the embodiment, the system can set these threshold turn angles, or they may be set by a facility or by a caregiver or other user. The settings can be simplified in some embodiments such that some or all of the turn angles are symmetric and as few as one angle is needed to be selected. Alternatively, as noted above, each the angles can be selected independently. The settings may be for a facility, a ward, a room, a bed, a patient. The settings can also vary based on past, present, or future data from the facility, caregiver or other user, system, or patient.

Upright Angle

Figure 10:
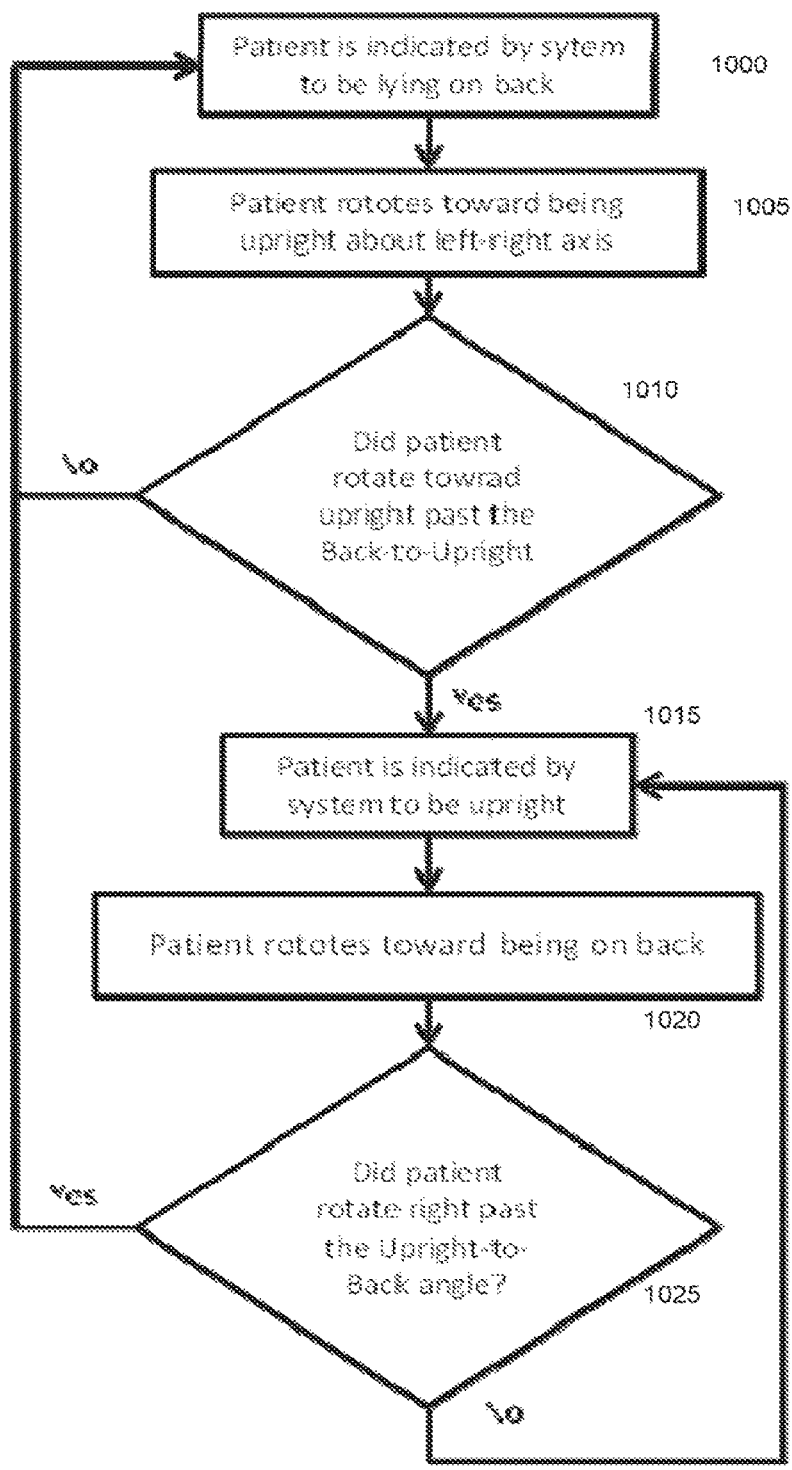
FIG. 10 illustrates a system flow for detecting and recording a patient rotating while also sitting up partially or entirely.

Referring next to FIG. 10, at least some embodiments of the present invention detect, through signals from one or more sensors affixed to or associated with the patient, when the patient experiences rotation about his/her left-right axis as shown at 1005. When rotating about this axis from lying on the back to being upright, the patient may pass an upright threshold angle, detected at 1010, at which point the patient is considered to be upright, shown at 1015. This angle can be set by being manually entered by the caregiver or the facility, or can be set or adjusted by the system depending on patient-specific factors or other suitable treatment protocols. The back-to-upright angle defines the angle at which the patient goes from being characterized as lying on his/her back to being characterized as upright. This upright-to-back angle, see 1020, 1025, defines the angle at which the patient goes from being characterized as upright to being characterized as lying on his/her back. The back-to-upright angle may be different from the upright-to-back angle. This hysteresis may be useful to avoid rapidly switching characterizing the patient as being on his/her back to being upright. In one implementation of the system, the back-to-upright angle is more upright than the upright-to-back angle.

Grace Period

In one embodiment, the system allows a facility to set a grace period, which defines within the system a period of time after a turn is due for a patient within which the patient can be turned and no non-compliance event is registered. Stated another way, once the turn period is reached and the patient is to be turned in accordance with a turn protocol, there may be a grace period in which the turn is considered to be compliant with the turn protocol as long as the turn occurs within an amount of time defined by the grace period after the turn period is over. This can be defined by the user or facility and it can be defined for all patients or set differently for individual patients based on their needs and turning characteristics. The grace period can also be set individually for a given facility, unit, ward, subset of a facility, hospital system, caregiver, user, or type of patient.

Capacitive Threshold

A capacitive sensor is one of the sensors the system can use on a patient sensor. Among other things the capacitive sensor can be used to detect if the patient sensor is attached to the patient. The capacitive threshold is the capacitance reading at which the sensor is becomes attached or unattached. The capacitive threshold can be set by the system, by the user, or by the facility. The unattached-to-attached capacitive reading threshold can be different from the attached-to-unattached reading threshold. This reduces the rapid switching between unattached an attached near the threshold. In one embodiment, the unattached-to-attached capacitive reading threshold is greater than the attached-to-unattached capacitive reading threshold. The capacitive reading thresholds can also be set individually for a given facility, unit, ward, subset of a facility, hospital system, caregiver, user, or type of patient.

Attached and Unattached Count Threshold

Figure 11:
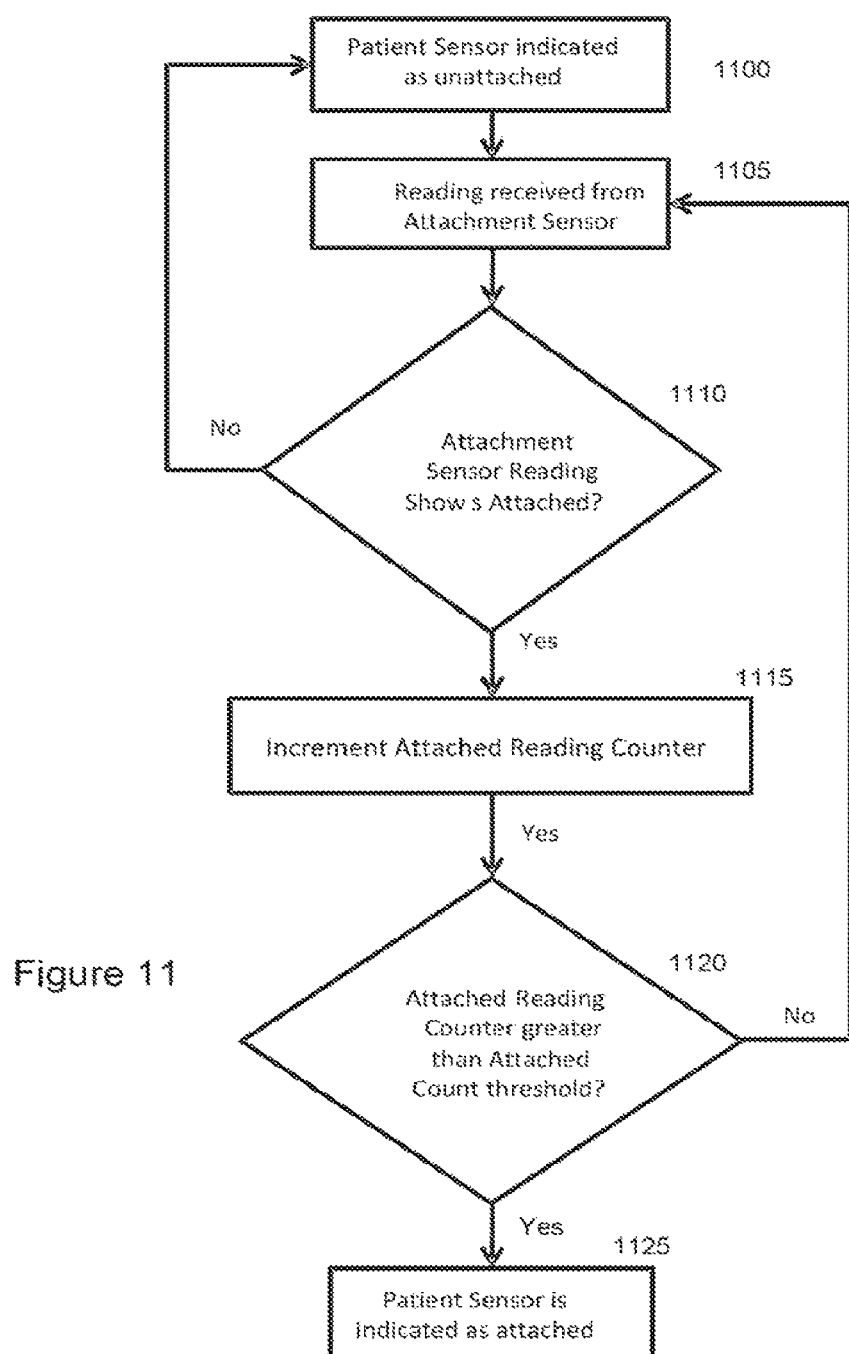
FIG. 11 illustrates a system flow for detecting whether a sensor is properly affixed to a patient.

The system may sense whether or not the patient sensor is attached to the patient. In one implementation, the system may use a capacitive sensor to determine attachment, though other sensing methods can be used. As shown in FIG. 11, the system may choose to only determine that the patient sensor is attached to the patient after one or more consecutive attached readings from the attachment sensing, after a certain amount time has passed in which the attachment sensing reports that the sensor is attached, or some combination of a number of readings and time. Similarly, the system may choose to only determine that the patient sensor is unattached from the patient after one or more consecutive unattached readings from the attachment sensing, after a certain amount time has passed in which the attachment sensing reports that the sensor is unattached, or some combination of a number of readings and time. One potential benefit of requiring multiple consecutive readings or period of time in which the sensor showing consistent attachment or detachment is that false attachment reports and transient attachment readings are reduced.

FIG. 11 shows a flowchart for an embodiment of an aspect of the system wherein the patient sensor starts as unattached, at 1100. The system thereafter receives multiple readings from the capacitive sensor and associated attachment logic, which together operate as an attachment sensor within the patient sensor, as shown at 1105 and 1110. The "attached reading" counter in the server increments for each reading, as at 1115. Upon receiving a threshold number of readings indicating that the sensor is attached, see 1120, the system identifies the patient sensor as attached, 1125, and monitors the associated patient.

Warning Time

In the event that one process or thread in the system software fails or stalls, another process or thread that is monitoring it can issue a warning to a user. The system may determine that the process or thread being monitored has failed by periodically checking that the process or thread is working or periodically receiving messages from it. The system may determine that the process or thread being monitored failed or stalled by seeing that there were not messages or that the process or thread has not been running for a certain amount of time and the system may warn the user after this time has passed.

User Group Data

Different user groups may exist that allow access to different sets of data. This separation of user groups allows for simplified management of protected health information and workflow information. Some users may only be allowed to view data that does not contain protected health information. Some users may only be allowed to view data certain patients. Some users may only be allowed to view information in a particular subset of a facility, such as a ward, or in a particular facility or set of facilities. Some users may not be allowed to view certain sections of the system such as the reports, home page, or settings. Some user may be able to view everything. The system may have preset user groups, and user groups and privileges may be defined by the facility.

Sensor Data

Data that is sent from the patient sensor will, in at least some embodiments, contain no protected health information. Instead, in such embodiments the data contains an identifier that can be associated with the patient to which the sensor is paired. Data associated with the patient sensor can be taken from a list including: time stamp for when the data was received, identifier of the process or user that generated the data entry, time stamp for when the data was generated, the patient sensor identifier, the sensor data including accelerometer data, capacitance sensor data, or attachment sensor data.

Referring next to FIGS. 12-17, various algorithms which can configure the operation of the host system 393 and which enable prediction and detection of bed exits and/or falls can be better appreciated. Not all of such algorithms need to be used in a single embodiment, and not all of even a single flowchart is required in all instances. In general, there is a characteristic pattern of movement that precedes a bed-exit. Prior to exiting a bed, a patient will typically turn towards the edge of the bed. Patients will also generally sit at the edge of the bed before exiting, unless they exit via a roll maneuver. Upon exiting the bed, there will be characteristic acceleration and altitude changes that occur as the patient moves away from the bed, which can occur in a controlled or uncontrolled fashion. In some embodiments, the pattern of movement that precedes, coincides, or follows a bed-exit can be detected via one or more sensors, including accelerometers, magnetometers, gyroscopes, or altimeters. In some implementations, a characteristic reading from a magnetometer can be used to indicate if a patient is in a position or orientation that is likely to precede a bed-exit. As mentioned, prior to exiting a bed, a patient's torso will generally be substantially parallel to the long-axis of the bed. Stated differently, the patient's anterior torso will be oriented towards the edge of the bed, perhaps in a sitting or upright position. Characteristic magnetometer readings, which may be combined with other sensor data, can be used to indicate that a bed-exit may be pending.

For each bed, the compass heading of the bed needs to be known or determined. The compass heading of the bed can be determined in relation to the long-axis of the bed, or in relation to any other defined axis. Once the compass heading of the bed is defined, it is then possible to know how the patient is oriented with respect to the bed. For example, if the patient's compass heading is orthogonal to the long-axis of the bed, this may indicate that the patient is positioned in a direction that typically precedes a bed-exit. If the patient's compass heading is further combined with orientation data (as determined by an accelerometer), it is then possible to know if the patient is sitting in an upright position at the edge of their bed, which may further increase the probability of a pending bed-exit.

In some implementations, the compass heading of every bed, chair, or other physical support apparatus is defined in the system. In terms of defining compass headings, each bed may be able to provide magnetometer data directly or a magnetometer may be associated with each bed. Although the physical location of specific beds may change, the compass heading of any given bed will generally be the same at any given location. Patient rooms are typically designed such that the bed is oriented in a particular fashion within the room. The process of defining compass headings for each bed can also be done manually. In order to improve the sensitivity of the bed-exit monitoring system, the patient acceleration and magnetometer data can be combined with real-time location sensing. The location of the patient can be determined via triangulation within the system's mesh network of wireless relay antennas, which are placed at defined locations. The direction that the sensor (and thus the patient) is facing can be determined by analyzing the perceived signal strength within the network of relay antennae.

Sensors applied to the patient's anterior torso can have a substantially directional transmission profile. Body tissues, radiopaque coatings, or other factors can attenuate the transmitted signal. As a result, the perceived signal strength varies with the direction of the sensor relative to the receiver (i.e. relay antenna). For example, consider two wireless sensors that are placed equidistant from a relay antenna, where each sensor has a directional transmission profile. Although the sensors are at the same distance from the relay antenna, the sensor that is oriented towards the relay antenna will be provide a higher perceived signal strength.

In order to know how the orientation of a given sensor affects the communication to a relay antenna in terms of perceived signal strength or time of flight, a system calibration step can be performed. When the system is initially installed and the relay antennas are placed in relatively known locations, a calibration step can be completed to determine the communication readings (signal strength, time of flight, etc) from a sensor at a given location for all possible sensor orientations, or a subset of common orientations. This calibration step can be done with a calibrating unit that simulates the patient (at least in terms of RF or wireless transmission) and rotates through various different orientations. Once an initial calibration step is done, the location of each patient can be determined. Given that the location of each bed can be provided, it is possible to know if a patient's location is coincident with the location of their bed. If the patient's determined location differs from the location of their bed, it can be assumed that a bed-exit has occurred. Furthermore, the direction that each patient is facing can be determined via perceived signal strength or time-of-flight analysis. This information can be combined with magnetometer data from the patient sensor to further define which direction a patient is facing. In general, patients will face in a characteristic direction prior to exiting a bed. Taken together, the teachings described herein can be used to determine if a patient bed-exit has happened, or is likely to happen.

In some implementations, the compass heading of every physical support apparatus is not initially defined, but is rather determined over time. When patients lie in bed, they typically lie parallel with the long-axis of the bed. If the patient is associated with a sensor that contains both a magnetometer and an accelerometer, and the patient is generally oriented parallel to the long-axis of the respective physical support apparatus, then the compass heading of the physical support apparatus can be inferred. As more data is provided at a particular location (even across multiple patients), the estimation of the compass heading for the physical support apparatus can be further refined. It is also possible that the compass heading for the physical support apparatus is initially provided manually or automatically, but then the compass heading is further refined based on patient data.

The present invention overcomes some of the limitations of the prior art by providing an improved means for activating and deactivating the bed-exit alarm mechanism. First, the system can be designed such that whenever a patient enters their bed, the bed-exit alarm mechanism is automatically set without requiring any caregiver input. Any subsequent bed exits, or attempted bed-exits, will then trigger the alarm. If a patient exits a bed with caregiver assistance, the bed-exit alarm can be disabled manually or automatically. With a manual means, the caregiver can disable the alarm by indicating in the system that the bed-exit is allowed. This "ignore bed-exit" indication can be provided via the user-interface or by interacting with the patient sensor, such as by tapping the sensor in a characteristic fashion. In some implementations, the "ignore bed-exit" indication is provided automatically by recognizing that a patient is in close proximity to a caregiver during a bed-exit. For example, if the caregiver is associated with a sensor and the relative distance between the caregiver's sensor and the patient's sensor can be resolved, then bed-exit alerts can automatically be disabled when the caregiver comes within a certain proximity to the patient. When the caregiver is no longer in close proximity to a given patient, the bed-exit alerts can automatically be re-enabled.

Figure 12:
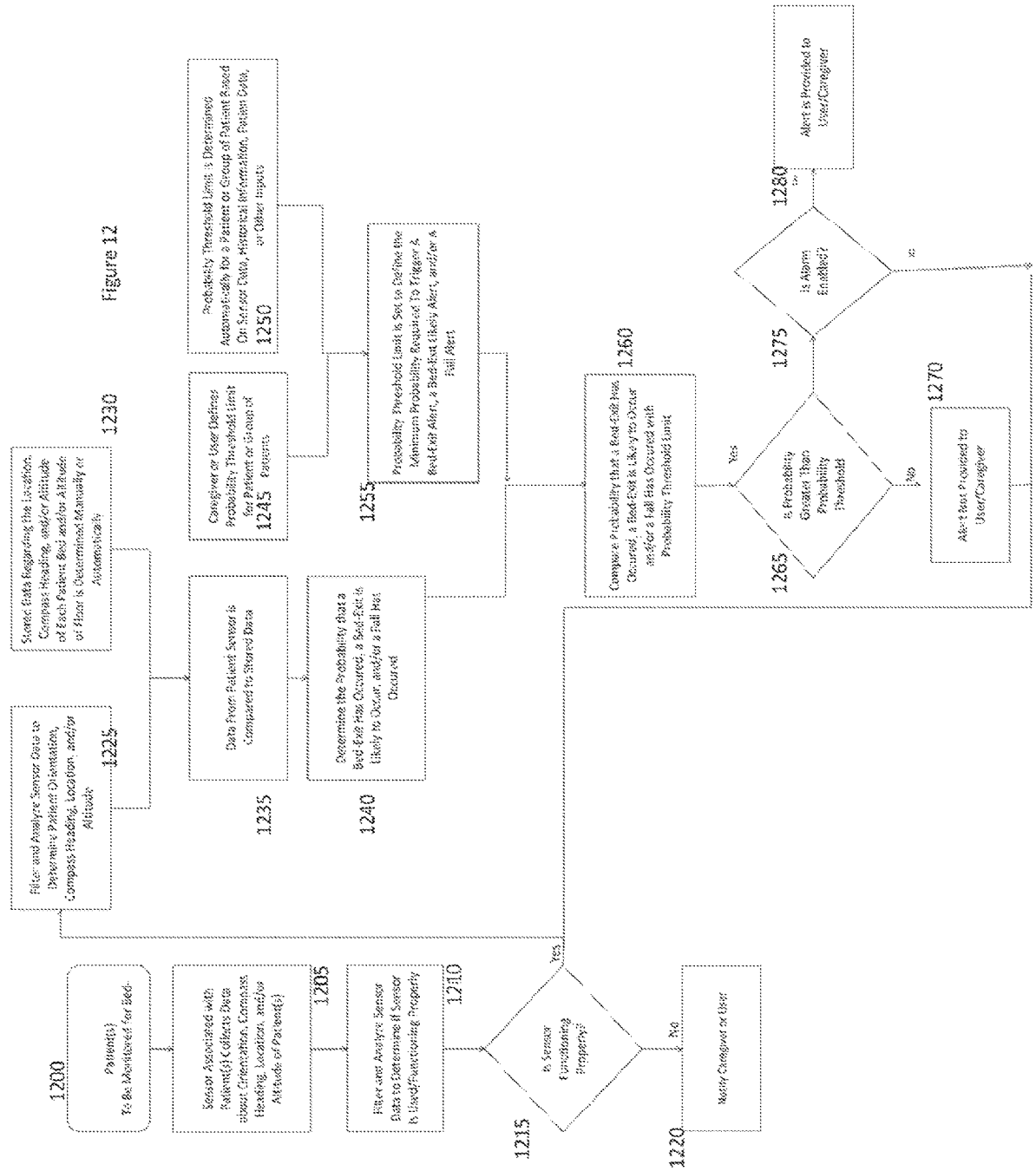
FIG. 12 illustrates in flow diagram form an embodiment of the process flow for determining if a patient bed-exit is likely to occur, a bed-exit has occurred, and/or a fall has occurred.

In particular, FIG. 12 illustrates in flow diagram form an embodiment of the process flow for determining if a patient bed-exit is likely to occur, a bed-exit has occurred, and/or a fall has occurred. Beginning at step 1200, a patient to be monitored for bed exits and/or falls is identified in the system, either by analysis of patient characteristics, patient health, patient history, manual entry, or other means. Data is collected from the sensor at 1205 and analyzed at 1210, to determine whether the sensor is operating properly. At 1215 a check is made to ensure that the sensor is functioning properly. If not, a caregiver is notified.

If the sensor is functioning properly, for the embodiment illustrated the process advances to step 1225, the sensor data is analyzed to determine patient orientation, compass heading, location and altitude. Stored data from 1230 is compared to sensor data at 1235, and at 1240 a determination is made as to whether a bed exit has occurred or is likely to occur, or a fall has occurred or is likely to occur. Probability thresholds derived from caregiver input 1245 or algorithmically 1250 are set at 1255 and then compared to the sensor data at 1260, leading to a yes or no conclusion at 1265 as the result of the threshold comparison. If the resulting probability is not greater than the threshold, the system loops via 1270 back to 1225. If the probability is greater than the threshold, a caregiver or automated system is notified directly or via an alarm 1275, 1280, or other means.

FIG. 13 illustrates in flow diagram form an embodiment of the process flow for determining if a patient bed-exit is likely to occur. At Step 1300, the compass heading for each patient bed is entered into the system. The process of entering the compass heading for each patient bed can occur manually or automatically. In some implementations, users define the compass heading for each bed during a system configuration setup process. In some implementations, the compass heading of the bed is automatically recorded by the bed and communicated to the system. In some implementations, a sensor is applied to the bed such that the compass heading of the bed can be measured and communicated to the system.

In some implementations, the compass heading of each bed is not initially defined, but is rather determined over time. When patients lie in bed, they typically lie parallel with the long-axis of the bed. If the patient is associated with a sensor that contains both a magnetometer and an accelerometer, and the patient is generally oriented parallel to the long-axis of the respective physical support apparatus, then the compass heading of the physical support apparatus can be inferred. As more data is provided at a particular location (even across multiple patients), the estimation of the compass heading for the bed can be further refined. It is also possible that the compass heading for the physical support apparatus is initially provided manually or automatically, but then the compass heading is further refined based on patient data.

At Step 1310, a sensor is applied to a patient's body in a known orientation with respect to their body, where said sensor contains at least a 1-axis accelerometer and a 2-axis magnetometer. At Step 1320, the accelerometer is at least a 1-axis accelerometer, where the longitudinal axis of the patient's body is parallel to the axis of sensitivity of the accelerometer. In some implementations, a 2 or 3-axis accelerometer may also be used, but this is not required in all embodiments.

At Step 1330, a determination is made as to whether the patient is sufficiently upright to be consistent with a bed-exit maneuver. The upright angle threshold can be set at any angle, such as >80 degrees. As the upright threshold angle is decreased, the sensitivity of bed-exit detection may increase but the specificity may decrease (more false positives). At Step 1340, the magnetometer is at least a 2-axis accelerometer, where the longitudinal axis of the patient's body is perpendicular to the plane of sensitivity of the magnetometer. In some implementations, a 3-axis magnetometer may also be used, but this is not required.

At Step 1350, a determination is made as to whether the patient's left-right body axis is sufficiently parallel to the long-axis of the patient's bed. The left-right body axis angle threshold can be set at any angle, such as <10 degrees from parallel. As the body axis angle gets further from parallel with the angle of the bed's long-axis, the sensitivity of bed-exit detection may increase but the specificity may decrease (more false positives). Depending upon the result at step 1350, a caregiver is alerted if a bed exit is predicted with sufficient probability, 1370, or the system loops for another time interval, 1380.

FIG. 14 illustrates in flow diagram form an embodiment of the process flow for determining if a patient bed-exit has occurred using accelerometer and altimeter information. At Step 1400, the altitude of the floor is entered in the system. The process of entering the floor altitude can occur manually or automatically. In some implementations, users define the floor altitude in each patient room or patient care location during a system configuration setup process. In some implementations, the floor altitude is automatically measured by altimeters that are at a known height above the floor and this information is communicated to the system.

At step 1410, the sensor is applied to the patient and activated as before. At steps 1420-1430, a determination is made from accelerometer data whether the patient is in a recumbent position. Next, at steps 1440-1450, an altimeter measurement is taken from the sensor and a determination is made as to whether the patient's altitude is sufficiently close to the altitude of the floor, using the altitude of the relay antennae as a reference. The altitude differential that is required to consider the patient altitude and floor altitude sufficiently close can be defined in the system. As the altitude differential is increased, the sensitivity of bed exit detection may increase but the specificity may decrease, such that more false positives occur. If the altitude differential indicates a bed exit, an alarm is activated and the caregiver is alerted, steps 1460-1470. If no indication of a bed exit, the system loops to step 1480 and tests again at the next time interval.

FIG. 15 illustrates in flow diagram form an embodiment of the process flow for determining if a patient bed-exit has occurred using location information. At Step 1500, the location for each patient bed is entered into the system. The process of entering the location for each patient bed can occur manually or automatically. In some implementations, users define the location for each bed during a system configuration setup process. In some implementations, the location of the bed is automatically recorded by the bed and communicated to the system. In some implementations, a bed sensor is applied to the bed such that the location of the bed can be measured and communicated to the system; such a sensor can be the same as or different from the sensor worn by the patient, although attaching a sensor 325 to a bed will cause only a portion of the functionality of the sensor 325 to be used. In any event, a sensor 325 is applied to the patient and activated, as before, and a location measurement is made, steps 1510-1520. At Step 1530, a determination is made as to whether the patient's location is sufficiently close to the patient's bed location to be inconsistent with a bed-exit. The minimum distance required to consider the patient and the patient's bed to be co-located can be set in the system, such as less than two meters. As the minimum distance angle is decreased, the sensitivity of bed-exit detection may increase but the specificity may decrease (more false positives). As with FIGS. 13 and 14, if the measurements indicate a bed exit, a caregiver is notified via a suitable alarm or indicator.

FIG. 16 illustrates in flow diagram form an embodiment of the process flow for determining if a patient fall has occurred using altimeter information. At Step 1600, the altitude of the floor is entered in the system. The process of entering the floor altitude can occur manually or automatically. In some implementations, users define the floor altitude in each patient room or patient care location during a system configuration setup process. In some implementations, the floor altitude is automatically measured by altimeters that are at a known height above the floor and this information is communicated to the system. The patient sensor is applied and activated, step 1610, and an altimeter measurement is made, 1620. At Step 1630, a determination is made as to whether the patient's altitude is sufficiently close to the altitude of the floor. The altitude differential that is required to consider the patient altitude and floor altitude sufficiently close can be defined in the system. As the altitude differential is increased, the sensitivity of fall detection may increase but the specificity may decrease (more false positives). If the sensor altitude is closer to the floor than a permissible differential, an alarm is sent to the caregiver as discussed above, or a loop occurs, steps 1640-1660.

FIG. 17 illustrates in flow diagram form an embodiment of the process flow for determining if a patient fall has occurred using altimeter and accelerometer information. Steps similar to those of FIGS. 12-16 are omitted for simplicity. At Step 1700, the altitude of the floor is entered in the system. The process of entering the floor altitude can occur manually or automatically. In some implementations, users define the floor altitude in each patient room or patient care location during a system configuration setup process. In some implementations, the floor altitude is automatically measured by altimeters that are at a known height above the floor and this information is communicated to the system. At Step 1730, a determination is made as to whether the patient's acceleration is consistent with a fall. The acceleration changes that are required to consider the patient to have fallen can be defined in the system. As the magnitude of acceleration changes is decreased, the sensitivity of fall detection may increase but the specificity may decrease (more false positives). At Step 1750, a determination is made as to whether the patient's altitude is sufficiently close to the altitude of the floor. The altitude differential that is required to consider the patient altitude and floor altitude sufficiently close can be defined in the system. As the altitude differential is increased, the sensitivity of fall detection may increase but the specificity may decrease (more false positives).

In some implementations, the magnetometer is a small, low-power, digital, 3-dimensional magnetic sensor that is responsive to magnetic fields, such as the earth's geomagnetic field. The magnetometer provides a means for determining the direction a patient is facing. When used in conjunction with a 3-axis accelerometer, orientation-independent compass information can be provided. It should be noted that combining a 3-axis accelerometer and a 3-axis magnetometer could simulate the data provided by a gyroscope. In some implementations, the sensor may incorporate a gyroscope, although it would need to be substantially miniaturized in order to be suitable for the intended application.

In addition to the foregoing features and aspects of the system, various user interface features assist in providing an efficient, easy to use, reliable patient management system. Some of these features are discussed below.

Splash Screen

In one embodiment of the system, shown in FIG. 18, a screen appears after the software is started or logged into showing information taken from a list including: Date, Company Logo, Product Name, Client Version, Network Version, Database Version and User Access Level. This screen can appear other times as well or be displayed upon request by the user.

Side Panel

In one embodiment of the system, a side panel is present in the user interface to facilitate navigation. Navigation buttons on the side panel can exist to allow access to different components of the user interface. These buttons along with other features, such as the exit button, help button, user ID, time, date, default turn period, default turn angle, decompression interval, facility name, and unit name, may be present on the side panel to by accessible by the user while accessing one or more or all sections of the user interface.

System Update Clock

In one embodiment of the system, a process or thread within the software is used to update a system update clock. The system update clock is used to show the time to the user in the user interface. The system can use this clock as an indicator to the user that the system is not working correctly if the clock is frozen, shows an incorrect time, or if the time increments at an incorrect pace.

Select Unit Screen

In one embodiment of the system, a section of the user interface exists where the user can select on which facility, unit, ward, or set of patients they wish to view data, as shown in FIG. 19.

Home Screen

In one embodiment of the system, a section of the user interface exists where the user can view data from one or more patients. The home screen can be set up to show all patient within a ward or unit or other subsection of a facility. The home screen can be set up to show one or more selected patients, or a group or type of patients. The patients can be sorted by room or bed or location. All rooms or beds can be shown regardless of whether the room or bed is occupied by a patient or a patient being monitored by the system. One potential benefit of this type of display is that a user can look to a constant location on the display for data on a specific room or bed. The patients can also be sorted by other data including: name, patient sensor identifier, caretaker, risk level, Braden score, time until next turn, turn period. The home screen can display information taken from a list including: room, bed, patient initials, patient name, time until next turn, time on current side, position or orientation, alerts. Graphical representations of the time until next turn, side, room, position or orientation may be used for quick viewing and to meet space constraints. The time until next turn can be displayed as a progress bar, clock, pie chart, or other graph. Different colors in the text, background, or graphics may also be used. The text, background, or graphic may be green when no turn is needed soon, yellow when a turn is close to due, and red when a turn is close to due or due. The home screen can also show how much time has elapsed since the turn was due. The home screen can also have a tag with a certain color with which the user can mark certain attributes associated with one or more patients. The patients can be displayed in one or more tables and in one or more columns. The tables may be scrollable. In one embodiment of the system, the system allows users to interact with the home screen by clicking on the patient or information associated with the patient and entering information or opening a patient information window.

Unassigned Sensor Table

In one embodiment of the system, and shown in Figure a table or list of the unassigned sensors is shown in the user interface, either in part of the home screen or in a different part of the user interface. The unassigned sensor table can display information taken from a list including: room, bed, patient sensor identifier, time until next turn, time on current side, position or orientation, alerts. Graphical representations of the time until next turn, side, room, position or orientation may be used for quick viewing and to meet space constraints. The time until next turn can be displayed as a progress bar, clock, pie chart, or other graph. Different colors in the text, background, or graphics may also be used. The text, background, or graphic may be green when no turn is needed soon, yellow when a turn is close to due, and red when a turn is close to due or due. The unassigned sensor display can also show how much time has elapsed since the turn was due. The patients can be displayed in one or more tables and in one or more columns. The table may be scrollable. In one embodiment of the system, the system allows users to interact with the unassigned sensor table by clicking on the sensor or information associated with the sensor and entering information or opening an unassigned sensor window.

Patient Information Window

In one embodiment of the system, the system allows the user to click on a patient entry within the home screen to access and edit information about the patient by opening a patient information window, such as shown in FIG. 21. The patient information window can display information taken from a list including: patient sensor identifier, unit, ward, room, bed, tag, patient name, patient first name, patient last name, medical record number, patient identifier, date of birth, restricted areas, areas to avoid, pressure ulcer data, turn period, time until next turn, turn alert pause status. One or more elements of this information can be edited by the user.

In one embodiment of the system, the system allows the user to click on a patient sensor entry within the unassigned sensor table to access and edit information about the patient by opening a patient information window, such as shown in FIG. 22. Editing this information allows the sensor to be associated with a patient or room or bed. The unassigned sensor window can display information taken from a list including: patient sensor identifier, unit, ward, room, bed, tag, patient name, patient first name, patient last name, medical record number, patient identifier, date of birth, restricted areas, areas to avoid, pressure ulcer data, turn period, time until next turn, turn alert pause status. One or more elements of this information can be edited by the user.

Discharging Patient or Deactivating Sensor

In one embodiment of the system, a window such as FIG. 23 can be displayed when the user requests to discharge a patient. The window can display information about the patient or sensor such that the user can easily verify that the correct patient or sensor has been selected.

Assigning Sensor to Existing Patient

In one embodiment of the system, if a user desires to assign a sensor to a patient who is already being monitored, the system can allow the user to select the patient form the home screen and assign the sensor to that patient, reducing the amount of data entry needed to assign the sensor to the patient. This can be useful when switching sensors on a patient or adding additional sensors to a patient.

Pausing Turn Alerts

In some embodiments of the system, if the patient has a medical procedure scheduled, the patient has an exam in progress, the patient is out of the bed, or is otherwise unavailable to be re-oriented, the system allows the user to pause the turn alerts and note the reason. A user interface screen for this function is shown in FIG. 24, and the associated system flow is shown in FIGS. 25A-25B.

In one embodiment, the system allows for a user to pause turn alerts and provide a reason why one or more patients cannot be turned during a certain time period. The user may pause a turn alert in the user interface of the system, as shown in FIG. 24. In one embodiment of the user interface, the selects one or more patients or rooms for which to pause turns. The user may select from a list of reasons including: patient refuses, patient not in room, patient not in bed, patient undergoing a procedure, patient busy, patient being examined or interviewed, patient is sleeping, equipment interferes with turn, or patient in unstable. The user may also enter a different reason or give no reason. The user may also select the time that the pause is effective for. The user may specify one or more of the following: pause period, pause interval, pause start, pause end, pause start trigger(s), pause end trigger(s). The system can record one or more of the following: the patient, the user, the pause time, pause interval, pause start, pause end, pause triggers, reason(s) for pause. The system may use the pause information to generate data about pause characteristics, users, or patients. In one embodiment, the system may use the pause information to inform compliance. For example, if the patient was planned to be turned but was not, and a legitimate pause reason was set, then the lack of turn may not be counted as a missed turn or a non-compliance event. The system may end the pause at the time specified by the user, at the end pause interval, when the patient is next turned, or upon certain triggers.

Manually Enter Turn

In one embodiment, as shown in the user screen of FIG. 26, the system allows the caregiver or other user to manually enter a turn for a patient, specifying which orientation/position the patient is turned. The system may log the turn as having happened when the manual turn was entered or the user may enter the time of the turn. One instance in which the can be used is when one or more patient sensors or the network is not communicating correctly.

Verify Sensor Attachment

In one embodiment, if the system indicates a patient sensor as unattached, the user can check to see if the sensor is actually attached. A user interface screen depicting such function is shown in FIG. 27. If the sensor is correctly attached and the patient sensor is oriented correctly with respect to the patient, the system allows the user can verify the attachment within the user interface. The user interface show a display of how the sensor should be attached and oriented relative to the patient for reference. The system allows the user to verify that the sensor is attached to the patient and that the sensor is oriented correctly relative to the patient. Once attachment is verified by the user the system records that the sensor is indicated to be attached. If subsequent readings from the attachment sensor show that the sensor is attached or if there are not additional attachment sensor readings from the sensor, the system continues to indicate that the sensor is attached. If the attachment sensor indicates that the sensor is unattached, the system may indicate that the sensor is unattached again. In one embodiment, the system allows the user to ignore future attachment readings from the sensor.

Administrative Settings

The system allows for users to enter settings for a particular facility, unit, ward, subsection of a facility, group of facility, or group of patients. Settings include the turn period default and options, turn alert pause interval default and options, the turn angle, upright angle, and the decompression default and options, as shown in FIGS. 28A-28B.

Alerts

The system may issue a number of alerts to the user or facility or for storage in its records.

Database Warning

In one embodiment, the system issues a warning when there is difficulty accessing a database. The system may have a certain threshold of time or attempts to access the database before issuing the warning. The system may also warn when an action cannot be performed due to difficulty accessing a database.

Turn Due Alert

In one embodiment, the system triggers the turn due alert if the accumulated time that the patient has been in a given position exceeds the threshold set by the user or facility. The time that the patient has been overdue for a repositioning may also be displayed. Repositioning the patient can lead to automatic resolution of this alert trigger once the Patient Sensor updates its status.

Upright Alert

In one embodiment, the system triggers the upright alert if the angle at which the Patient Sensor on the patient's torso is tilted is greater than the threshold Upright Angle. This is not an Alert that inherently requires action. However, repositioning the patient can lead to resolution of this alert trigger.

Prone Alert

In one embodiment, the system triggers the prone alert if the acceleration detected along the patient's anterior-posterior axis by the Patient Sensor is negative. This is not an Alert that inherently requires action. However, repositioning the patient can lead to resolution of this alert trigger.

No Signal

In one embodiment, the system triggers the no signal alert if data from the Patient Sensor has not been detected by the User Interface to have been updated within a time threshold. The user may be instructed to determine if the Patient Sensor is too far from any Relay Antennas or if something may be blocking the signal. Alternatively, the user may replace the sensor or contact Centauri Medical Customer Service Unattached In one embodiment, the system triggers the unattached alert if the attachment sensor, which can be but is not limited to a capacitance sensor, reports a reading beyond the threshold for human attachment.

Pause Alert

In one embodiment, the system triggers the pause alert when the user sets a Pause Turn Alert for a patient. This alert can last for a duration equal to the duration of the pause. This is not an Alert that inherently requires action. The alert may disappear when the pause has expired.

Patient Information Not Updating Warning

In one embodiment, the system triggers the patient information not updating alert if the database has not been accessible for greater than or equal to a preset threshold, and the time elapsed since the database had last been accessible can be displayed. The user should be aware that the data displayed may be out of date.

Home Screen Warning

In one embodiment, the system triggers the home screen alert if every patient and Patient Sensor displayed on the Home screen has not been updated over a period equal to a preset threshold, and the database is accessible, and the duration since the last complete update can be displayed. This can tell the user that the data displayed may be out of date by the amount of time in the preset threshold.

Components Embodied in Any Suitable Computer Device, e.g., Smartphones

It should be understood that each component of any of the networks or systems disclosed herein, e.g., each component of the example networks shown in FIGS. 3A-3B and FIGS. 4A-4D (including, for example, each relay antenna, host system, server (e.g., base station host, back-end server, etc.), database, terminal, and/or caregiver display) may comprise or be embodied in any suitable computer device, e.g., a server, desktop computer, laptop computer, tablet computer, smart phone, smart watch.

For example, in some embodiments, a caregiver display may be embodied in a smartphone comprising a suitable display device and software for displaying any of relevant information as disclosed herein. As another example, in some embodiments, one or more relay antenna may be embodied in one or more smartphones comprising any suitable sensor(s) and/or other hardware and software for providing any of the relay antenna functionality disclosed herein.

As yet another example, one or more smartphones, laptop computers, or tablet computers may provide reference altitude data (e.g., for detecting a patient fall or bed exit as disclosed herein). For example, a smartphone, laptop, or tablet may include an integrated barometer or other sensor(s) or device(s) configured to detect an altitude of the smartphone, laptop, or tablet or information from which an altitude of the smartphone, laptop, or tablet can be determined by a processor of the relevant patient monitoring system.

In some embodiments configured to monitor for a patient bed exit and/or patient fall, a smartphone, laptop computer, tablet computer, desktop computer, or other computer device may host, store, or have access to (e.g., via the internet) a software application executable by a processor of the respective computer device to receive data from one or more patient-worn sensor devices and analyze such data (and/or other data) to determine a patient orientation (e.g., relative to a physical support apparatus) and identify a patient bed exit condition and/or patient fall condition, and/or to display information indicating the patient orientation, an alert or other indication of a detected patient bed exit condition and/or patient fall condition, and/or any other relevant information to a user.

For example, an application loaded on a smartphone, laptop computer, tablet computer, or desktop computer, or a web-based application accessible to any of such computers, may be executable by a processor of the respective computer to (a) receive sensor data from a patient-worn sensor device (e.g., via a wireless link); (b) determine or access an orientation of a bed, chair, or other physical support apparatus; (c) calculate an orientation of the patient relative to the physical support apparatus based on (i) the orientation of the physical support apparatus and (ii) the sensor data received from the patient-worn sensor device; (d) identify a bed exit (e.g., an occurrence or anticipated occurrence of the patient exiting the physical support apparatus) based at least on the determined orientation of the patient relative to the physical support apparatus; and (e) display an alert or indication of the patient orientation and/or identified bed exit via a display device of the respective computer.

As another example, an application loaded on a smartphone, laptop computer, tablet computer, or desktop computer, or a web-based application accessible to any of such computers, may be executable by a processor of the respective computer to (a) receive sensor data from a patient-worn sensor device (e.g., via a wireless link), which may include (i) patient altitude data indicating an altitude or changes in altitude of the patient and (ii) patient acceleration data including at least one of a static acceleration or a dynamic acceleration of the patient; (b) determine a relative altitude of the patient based on (a) the collected patient altitude data and (b) a reference altitude; (c) identify a patient fall or a bed exit (e.g., an occurrence or anticipated occurrence of the patient exiting a physical support apparatus) based at least on (i) the determined relative altitude of the patient, as determined based on the collected patient altitude data and the reference altitude, and (ii) the collected patient acceleration data; and (d) display an alert or indication of the patient altitude and/or an identified fall or bed exit via a display device of the respective computer.

The invention claimed is:

1. A method for automated monitoring of a person's position, comprising:
receiving, at a processor, sensor data regarding an orientation of the person;
monitoring, by the processor, the orientation of the person over time based on the received sensor data;
managing an accumulated time counter associated with a particular orientation of the person based on the monitored orientation of the person, including:
increasing the accumulated time counter while the person is positioned in the particular orientation; and decreasing the accumulated time counter while the person is not positioned in the particular orientation; and generating, by the processor, a notification based on a state of the accumulated time counter.

2. The method of claim 1, wherein decreasing the accumulated time counter while the person is not positioned in the particular orientation comprises gradually decreasing the accumulated time counter at a defined depressurization rate.

3. The method of claim 1, comprising increasing the accumulated time counter at a pressurization rate and decreasing the accumulated time counter at a depressurization rate different than the pressurization rate.

4. The method of claim 3, wherein the depressurization rate for decreasing the accumulated time counter is greater than the pressurization rate for increasing the accumulated time counter.

5. The method of claim 1, comprising:
comparing, by the processor, the accumulated time counter to a pressurization threshold defined by a turn protocol for the person; and
generating, by the processor, a notification if the accumulated time counter exceeds the pressurization threshold.

6. The method of claim 1, comprising dynamically adjusting, by the processor, at least one of a pressurization rate for increasing the accumulated time counter and a depressurization rate for decreasing the accumulated time counter.

7. The method of claim 1, comprising outputting the notification via an audible or visual output device.

8. The method of claim 1, wherein the processor is provided in a wearable sensor device.

9. The method of claim 1, wherein:
the sensor data is generated by at least one sensor provided in a wearable sensor device; and
the processor is provided in a computer system or device distinct from the wearable sensor device.

10. The method of claim 1, comprising controlling a display device to display a current orientation and a recorded turn history of the person.

11. The method of claim 1, comprising controlling a display device to display a current status of the accumulated time counter.

12. The method of claim 1, comprising:
comparing, by the processor, the accumulated time counter with a predetermined accumulated time threshold; and
controlling a display device to indicate the accumulated time counter exceeding the predetermined accumulated time threshold.

13. The method of claim 1, comprising:
comparing, by the processor, the accumulated time counter to a pressurization threshold to determine a remaining time until a next turn, as defined by a turn protocol for the person; and
controlling a display device to visually indicate the remaining time until the next turn.

14. The method of claim 13, wherein controlling the display device to visually indicate the remaining time until the next turn comprises dynamically changing a displayed color as a function of the remaining time until the next turn.

15. The method of claim 13, comprising displaying, by a display device, a progress bar, clock, or pie chart to visually indicate the remaining time until the next turn.

16. The method of claim 1, comprising:
comparing, by the processor, the accumulated time counter to a pressurization threshold to determine a time the person has been overdue for a turn, as defined by a turn protocol for the person; and
controlling a display device to visually indicate the time the person has been overdue for a turn.

17. A method for automated monitoring of a person's position, comprising:
receiving, at a processor, sensor data regarding an orientation of the person,
monitoring, by the processor, the orientation of the person over time based on the received sensor data;
determining, by the processor, whether the person is in a particular orientation based on the monitored sensor data;
controlling, by the processor, a time counter associated with the particular orientation, including at least one of (a) increasing the time counter at a rate of increase while the person is positioned in the particular orientation or (b) decreasing the time counter at a rate of decrease while the person is not positioned in the particular orientation;
dynamically adjusting, by the processor, at least one of the rate of increase or the rate of decrease of the time counter as a function of at least one factor selected from the group consisting of (a) a time of day, (b) a type of support surface on which the person is supported, (c) a defined risk level for the person, (d) a health status of the person, (e) a presence of a pressure ulcer on the person, (f) caregiver availability information, (g) a parameter of at least one orientation change of the person, and (h) an orientation history of the person based on the monitored sensor data;
controlling the time counter, by the processor, using the dynamically adjusted the rate of increase or rate of decrease; and
generating a visual or audible notification based on the time counter.

18. The method of claim 17, comprising:
determining a magnitude of an orientation change of the person; and
dynamically adjusting at least one of the rate of increase or the rate of decrease of the time counter as a function of the determined magnitude of the orientation change.

19. The method of claim 17, wherein determining a magnitude of an orientation change of the person comprises determining a degree of rotation of the person around at least one axis.

20. The method of claim 18, comprising increasing the rate of decrease of the time counter as a function of an increased degree of rotation of the person.

21. The method of claim 17, comprising:
determining a frequency of orientation changes of the person; and
dynamically adjusting at least one of the rate of increase or the rate of decrease of the time counter as a function of the determined frequency of orientation changes.

22. A method for automated monitoring of a person's position, comprising:
receiving, at a processor, sensor data regarding an orientation of the person,
monitoring, by the processor, the orientation of the person over time based on the received sensor data;
managing, by the processor, a plurality of accumulated time counters, each corresponding with one of a plurality of different orientations of the person, wherein managing each accumulated time counter corresponding with one of the plurality of different orientations comprises:

increasing the accumulated time counter while the person is positioned in the corresponding orientation of the person; and decreasing the accumulated time counter while the person is not positioned in the corresponding orientation of the person; and generating, by the processor, a visual or audible notification based on a state of at least one of the plurality of accumulated time counters.

23. The method of claim 22, comprising, for each accumulated time counter:

increasing the accumulated time counter at a defined rate of increase while the person is positioned in the corresponding orientation of the person; and decreasing the accumulated time counter at a defined rate of decrease while the person is not positioned in the corresponding orientation of the person; and wherein for a first and a second accumulated time counter of the plurality of accumulated time counters corresponding with a first and a second orientation of the plurality of different orientations:

the defined rate of increase of the first accumulated time counter differs from the defined rate of increase of the second accumulated time counter; and/or the defined rate of decrease of the first accumulated time counter differs from the defined rate of decrease of the second accumulated time counter.

24. The method of claim 22, wherein, for a respective accumulated time counter corresponding with a respective orientation of the person, decreasing the accumulated time counter while the person is not positioned in the corresponding respective orientation of the person comprises gradually decreasing the respective accumulated time counter at a defined depressurization rate.

25. The method of claim 22, wherein for a particular accumulated time counter of the plurality of accumulated time counters, the accumulated time counter is increased at a pressurization rate and decreased at a depressurization rate different than the defined pressurization rate.

26. The method of claim 25, wherein the depressurization rate is greater than the pressurization rate.

27. The method of claim 22, comprising:

comparing the respective accumulated time counter to a pressurization threshold defined by a turn protocol for the person; and causing a display device to display a notification if the respective accumulated time counter exceeds the pressurization threshold.

28. The method of claim 22, comprising causing a display device to display a status of each of the plurality of accumulated time counters.

* * * * *